(12) United States Patent
Koide et al.

(10) Patent No.: US 10,041,937 B2
(45) Date of Patent: Aug. 7, 2018

(54) MACROPHAGE IDENTIFICATION AGENT, AND IDENTIFICATION METHOD, SORTING METHOD, EVALUATION METHOD, SCREENING METHOD AND KIT USING THE MACROPHAGE IDENTIFIER AGENT

(71) Applicant: CANON KABUSHIKI KAISHA, Tokyo (JP)

(72) Inventors: Fumiyo Koide, Yokohama (JP); Tsuyoshi Nomoto, Tokyo (JP); Sachiko Yamauchi, Yokohama (JP); Kohei Watanabe, Brookline, MA (US); Taichi Shintou, Saitama (JP); Takeshi Miyazaki, Ebina (JP); Yasuhiko Tabata, Kyoto (JP); Eri Sanda, Kyoto (JP)

(73) Assignee: CANON KABUSHIKI KAISHA, Tokyo (JP)

(*) Notice: Subject to any disclaimer, the term of this patent is extended or adjusted under 35 U.S.C. 154(b) by 0 days.

(21) Appl. No.: 14/766,386

(22) PCT Filed: May 29, 2014

(86) PCT No.: PCT/JP2014/064900
§ 371 (c)(1),
(2) Date: Aug. 6, 2015

(87) PCT Pub. No.: WO2014/192972
PCT Pub. Date: Dec. 4, 2014

(65) Prior Publication Data
US 2016/0018389 A1 Jan. 21, 2016

(30) Foreign Application Priority Data
May 30, 2013 (JP) .................. 2013-114578

(51) Int. Cl.
| | |
|---|---|
| G01N 33/52 | (2006.01) |
| C07D 209/14 | (2006.01) |
| G01N 33/50 | (2006.01) |
| C12N 5/0786 | (2010.01) |
| C07D 401/06 | (2006.01) |
| C07D 403/06 | (2006.01) |
| C07D 403/08 | (2006.01) |
| C07D 413/06 | (2006.01) |
| C07D 413/08 | (2006.01) |
| C07D 417/06 | (2006.01) |
| C07D 417/08 | (2006.01) |
| C07D 417/14 | (2006.01) |
| C07D 209/80 | (2006.01) |
| C07D 277/64 | (2006.01) |
| C07D 413/04 | (2006.01) |
| C07D 498/04 | (2006.01) |
| C07F 5/02 | (2006.01) |

(52) U.S. Cl.
CPC ....... *G01N 33/5094* (2013.01); *C07D 209/14* (2013.01); *C07D 209/80* (2013.01); *C07D 277/64* (2013.01); *C07D 401/06* (2013.01); *C07D 403/06* (2013.01); *C07D 403/08* (2013.01); *C07D 413/04* (2013.01); *C07D 413/06* (2013.01); *C07D 413/08* (2013.01); *C07D 417/06* (2013.01); *C07D 417/08* (2013.01); *C07D 417/14* (2013.01); *C07D 498/04* (2013.01); *C07F 5/022* (2013.01); *C07F 5/027* (2013.01); *C12N 5/0645* (2013.01); *G01N 33/5005* (2013.01); *G01N 33/52* (2013.01)

(58) Field of Classification Search
CPC .................. G01N 33/5094; C07D 209/14
See application file for complete search history.

(56) References Cited

U.S. PATENT DOCUMENTS

| | | |
|---|---|---|
| 4,803,161 A | 2/1989 | Babb et al. |
| 8,652,438 B2 | 2/2014 | Nomoto et al. |
| 8,753,608 B2 | 6/2014 | Tabata et al. |

(Continued)

FOREIGN PATENT DOCUMENTS

| | | |
|---|---|---|
| EP | 2 685 261 A1 | 1/2014 |
| JP | 2003-012547 A | 1/2003 |

(Continued)

OTHER PUBLICATIONS

Vogel, et al. Journal of Neuroinflammation 2013, 10, pp. 1-12.*

(Continued)

*Primary Examiner* — Shawquia Jackson
(74) *Attorney, Agent, or Firm* — Fitzpatrick, Cella, Harper & Scinto

(57) ABSTRACT

An object of the present invention is to provide an identification method for a macrophage subtype using an organic compound. Another object of the present invention is to provide a macrophage identification agent containing an organic compound in which a spectral characteristic obtained when the organic compound is added is different depending on a macrophage subtype. Still another object of the present invention is to provide an evaluation method for a macrophage subtype using a macrophage identification agent, an analysis method for correlation between a macrophage subtype and a test substance, a screening method for correlation between a macrophage subtype and a test substance, and a kit. An identification method for a macrophage subtype utilizing that a spectral characteristic obtained with an organic compound added is different depending on a macrophage subtype is provided.

31 Claims, 25 Drawing Sheets

(56) References Cited

U.S. PATENT DOCUMENTS

| | | | |
|---|---|---|---|
| 9,132,203 | B2 | 9/2015 | Tabata et al. |
| 9,228,952 | B2 | 1/2016 | Watanabe et al. |
| 2003/0157026 | A1 | 8/2003 | Aizawa et al. |
| 2011/0189096 | A1 | 8/2011 | Watanabe et al. |
| 2011/0236310 | A1 | 9/2011 | Watanabe et al. |
| 2011/0306072 | A1 | 12/2011 | Nicholls et al. |
| 2011/0306120 | A1 | 12/2011 | Nicholls et al. |
| 2012/0207683 | A1 | 8/2012 | Tanaka et al. |
| 2013/0280169 | A1 | 10/2013 | Watanabe et al. |
| 2013/0323764 | A1 | 12/2013 | Nicholls et al. |
| 2013/0344581 | A1 | 12/2013 | Nicholls et al. |
| 2014/0017722 | A1 | 1/2014 | Watanabe et al. |
| 2014/0112869 | A1 | 4/2014 | Nomoto et al. |
| 2015/0139908 | A1 | 5/2015 | Watanabe et al. |
| 2015/0182518 | A1 | 7/2015 | Shintou et al. |
| 2015/0274715 | A1 | 10/2015 | Shintou et al. |

FOREIGN PATENT DOCUMENTS

| | | |
|---|---|---|
| JP | 2010-148447 A | 7/2010 |
| WO | 85/05179 A1 | 11/1985 |
| WO | 03/104210 A1 | 12/2003 |
| WO | 2007/102146 A2 | 9/2007 |
| WO | 2009/012156 A2 | 1/2009 |
| WO | 2010/007432 A2 | 1/2010 |

OTHER PUBLICATIONS

Fernando O. Martinez et al., "Transcriptional Profiling of the Human Monocyte-to-Macrophage Differentiation and Polarization: New Molecules and Patterns of Gene Expression," 177(10) J. Immunol. 7303-7311 (Nov. 2006) (XP009160929).

Kristina A. Kigerl et al., "Identification of Two Distinct Macrophage Subsets with Divergent Effects Causing either Neurotoxicity or Regeneration in the Injured Mouse Spinal Cord," 29(43) J. Neurosci. 13435-13444 (Oct. 2009) (XP055271828).

Extended European Search Report in European Application No. 14804756.6 (dated May 30, 2016).

Karine Lolmede et al., "Inflammatory and Alternatively Activated Human Macrophages Attract Vessel-Associated Stem Cells, Relying on Separate HMGB1- and MMP-9-Dependent Pathways," 85 J. Leukoc. Biol. 779-787 (May 2009).

Masujiro Katayanagi, "Preparation of Styryl Dyes from Aramatic Heterocyclic Ammonium Salts. X," 69(5) Yakugaku Zasshi 237-240 (1949).

Liang Han et al., "One-Pot Synthesis of 3-(2'-Benzoxazole)-2H-1-Benzopyran-2-one Derivatives with Benzoic Acid Catalysis," 15(4) Heterocyclic Comm. 245-250 (2009).

Mayur Shah et al., "Pyrromethene-BF2 Complexes as Laser Dyes:1.," 1(5) Heteroatom Chem. 389-399 (1990).

Gilles Ulrich et al., "Pyrromethene Dialkynyl Borane Complexes for "Cascatelle" Energy Transfer and Protein Labeling," 44 Angew. Chem. 3694-3698 (Int. Ed. Engl., 2005).

Matthias Kollmannsberger et al., "Electrogenerated Chemiluminescence and Proton-Dependent Switching of Fluorescence: Functionalized Difluoroboradiaza-s-indacenes," 36(12) Angew. Chem. 1333-1335 (Int. Ed. Engl., 1997).

Elly JF Vereyken et al., "Classically and Alternatively Activated Bone Marrow Derived Macrophages Differ in Cytoskeletal Functions and Migration Towards Specific CNS Cell Types," 8 J. Neuroinflam. 58: 1-16 (May 2011) (URL: http://www.ncbi.nlm.nih.gov/pmc/articles/PMC3123187).

S. Mohanty et al., "Effect of Structural Changes in the Chromophoric Chain on Absorption of Dyes Derived from Benzthiazoles," 6(3) Indian J. Chem. 136-139 (1968).

Lunxu Liu et al., "Interleukin-17 and Prostaglandin E2 are Involved in Formation of an M2 Macrophage-Dominant Microenvironment in Lung Cancer," 7(7) J. Thorac. Oncol. 1091-1100 (Jul. 2012).

Delisha A. Stewart et al., "Basal-like Breast Cancer Cells Induce Phenotypic and Genomic Changes in Macrophages," 10(6) Mol. Cancer Res. 727-738 (Jun. 2012).

Communication pursuant to Article 94(3) EPC in European Application No. 14804756.6 (dated Jun. 14, 2017).

Communication pursuant to Article 94(3) EPC in European Application No. 14804756.6 (dated Mar. 20, 2018).

Notification of Reasons for Refusal in Japanese Application No. 2014-111593 (dated May 8, 2018).

* cited by examiner

US 10,041,937 B2

MACROPHAGE IDENTIFICATION AGENT, AND IDENTIFICATION METHOD, SORTING METHOD, EVALUATION METHOD, SCREENING METHOD AND KIT USING THE MACROPHAGE IDENTIFIER AGENT

TECHNICAL FIELD

The present invention relates to a macrophage identification agent that shows different staining properties depending on a macrophage subtype, and an identification method, a sorting method, an evaluation method, a screening method and a kit for a macrophage subtype by using the macrophage identification agent.

BACKGROUND ART

As the advancement of the aging society in recent years, the number of patients suffering from inflammatory diseases such as cancers, lifestyle related diseases and circulatory diseases is increasing, and as a result, there arises a social problem of, for example, the increase of medical expenses. In order to solve the problem, there is a demand for a diagnostic method with which an inflammatory disease can be detected at an early stage or an effective treatment method with which an inflammatory disease can be cured before becoming severe. An inflammatory disease is considered to be caused and become serious when inflammation becomes chronic. There are, however, many unknown parts in the chronic inflammation, and the mechanism has not been clarified yet. Therefore, studies for purpose of clarifying the mechanism of the chronic inflammation are being earnestly prosecuted inside and outside Japan.

As one of cell types playing a significant role in the chronic inflammation, attention is recently paid to macrophage, that is, a type of leucocytes. It is currently known that there are at least two subtypes of macrophage, that is, one having a function to accelerate inflammation (M1 macrophage) and one having a function to inhibit inflammation (M2 macrophage).

It has been revealed that the macrophage subtypes (hereinafter referred to merely as the subtypes; herein, the term "subtype" refers to the macrophage subtype) are significantly related to pathologic change in inflammatory diseases such as cancer, type II diabetes mellitus related to fatness, arterial sclerosis, and nephritis. There are a large number of reports on the relation between the subtype and the pathology. For example, it is known that the number, the density, the balance or the like of the subtypes reflects the pathology. Accordingly, identification of a subtype is expected to be applied to diagnosis and treatment.

As a method for identifying a subtype, a method in which a fluorescent dye-labeled antibody is used for identifying a protein marker specifically expressed on cell surfaces of each subtype (hereinafter referred to as the fluorescent antibody method) is known (NPL 1).

On the other hand, an exemplified method in which a porphyrin compound is used to be specifically incorporated into macrophages infiltrated into an inflammatory site in a pancreatic island is disclosed (PTL 1).

If identification and evaluation of a subtype, and evaluation, analysis and screening of influence of a substance on the subtype can be simply performed, the roles of the subtype played in an inflammatory disease will be understood in more detail. An effective diagnostic method for an inflammatory disease can be expected to be developed based on the identification and evaluation of the subtype. Besides, if the subtype is controlled in a disease site or a specific subtype having been adjusted in vitro is administered based on the identification, evaluation, analysis and screening of the subtype, an early treatment method for the inflammatory disease can be developed.

CITATION LIST

Patent Literature

PTL 1: Japanese Patent Application Laid-Open No. 2003-12547
PTL 2: WO 2010/07432

Non Patent Literature

NPL 1: Angelo A Manfredi et al., Journal of Leukocyte Biology, pp. 779-787 (2009)
NPL 2: Yakugaku Zasshi, Vol., 69, pp. 237-239, 1949
NPL 3: Heterocyclic Communications, 15(4), 2009, pp. 245-250
NPL 4: Heteroatom Chemistry, Volume 1, Number 5, 1990, pp. 389-399
NPL 5: Angew. Chem., Int. Ed. Engl., 2005, 44, pp. 3694-3698
NPL 6: Angew. Chem., Int. Ed. Engl., 1997, 36, pp. 1333-1335
NPL 7: J. Neuroinflam., vol. 8, 2011, 58 (URL: http://www.ncbi.nlm.nih.gov/pmc/articles/PMC3123187)
NPL 8: Indian Journal of Chemistry, Vol. 6, pp. 136-139, 1968
NPL 9: J. Thorac. Oncol., Vol. 7, pp. 1091-1100, 2012
NPL 10: Mol. Cancer Res., Vol. 10, p. p. 727-738, 2012

SUMMARY OF INVENTION

Technical Problem

The fluorescent antibody method disclosed in NPL 1 includes a large number of treatments for preventing a fluorescent antibody from non-specifically binding to a biological tissue sample, and a long time is necessary for staining. This method further has a problem of, for example, expensiveness because storage stability of the antibody is poor and a difference between lots largely affects.

On the other hand, if the porphyrin dye compound as disclosed in PTL 1 is used, there arises a problem in which M1 macrophage and M2 macrophage cannot be identified each other.

Solution to Problem

The present inventors made earnest studies for solving the aforementioned problems, resulting in finding a method for identifying the macrophage subtypes M1 and M2 by using an organic compound.

Specifically, the present invention provides a method for identifying macrophage subtypes M1 and M2, in which the macrophages M1 and M2 are identified based on spectral characteristics obtained with an organic compound added thereto.

Besides, a macrophage identification agent of the present invention is a macrophage identification agent for identifying the macrophage subtypes M1 and M2, and contains one or more organic compounds, and a spectral characteristic obtained when added is different between the macrophage M1 and the macrophage M2.

Moreover, the present inventors have developed, by using the macrophage identification agent, a sorting method for a subtype, an analysis method for correlation between a subtype and a substance, a screening method and a kit, and thus, the present invention has been accomplished.

Advantageous Effects of Invention

According to the present invention, a subtype can be identified by a simple and inexpensive method. As a result, a subtype can be efficiently identified or separated, the number, density, balance or the like of a subtype can be evaluated, and a substance affecting a subtype can be evaluated or screened.

Further features of the present invention will become apparent from the following description of exemplary embodiments with reference to the attached drawings.

DESCRIPTION OF EMBODIMENTS

Figure 1:
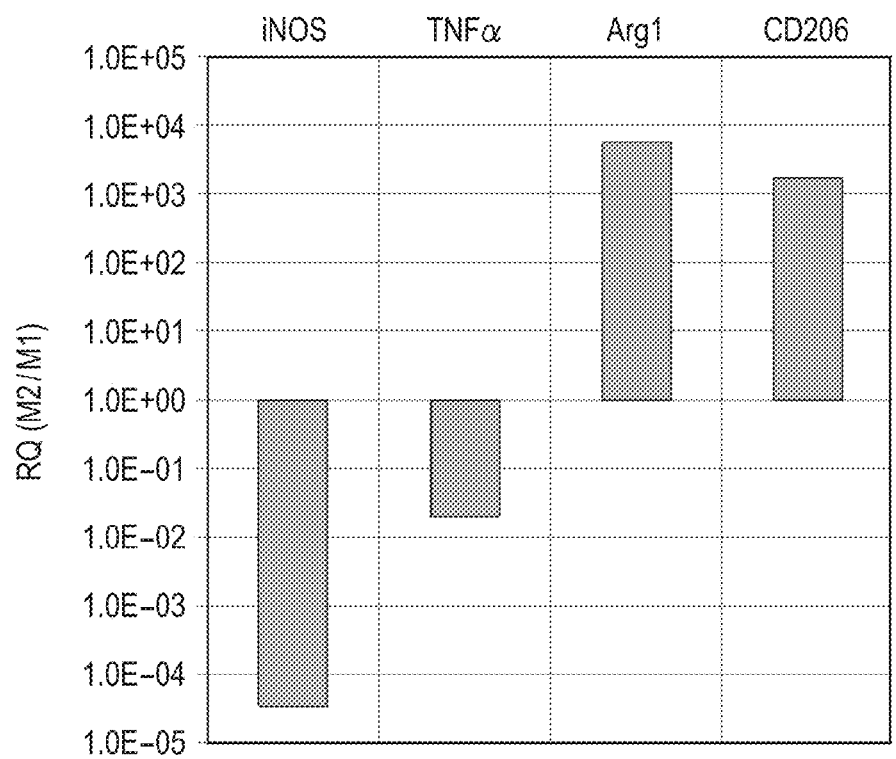
FIG. 1 illustrates a result of gene expression analysis performed on M1 macrophage and M2 macrophage differentiated from mouse bone marrow cells.

Preferred embodiments of the present invention will now be described in detail in accordance with the accompanying drawings.

The present invention provides a macrophage identification agent for identifying macrophage subtypes M1 and M2, containing one or more organic compounds, in which a spectral characteristic obtained when the compound is added is different between the macrophage M1 and the macrophage M2.

Embodiments of the present invention will now be described. It is noted that the individual embodiments exemplarily describe a novel identification method for macrophage subtypes, a macrophage identification agent, a sorting method, an evaluation method, an analysis method for correlation between a subtype and a substance, a screening method and a kit of the present invention, which do not limit the present invention.

Embodiment 1

A macrophage identification agent according to Embodiment 1 of the present invention contains one or more compounds represented by the following general formula (1):

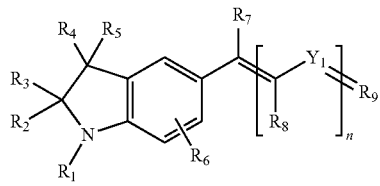

General Formula (1)

In general formula (1), $R_1$ represents a hydrogen atom, an alkyl group, an aralkyl group, an alkenyl group, or an aryl group; and $R_2$ to $R_5$ each independently represent a hydrogen atom, an alkyl group, an aryl group, a carboxyl group, a carboxylalkyl group, or an alkylcarbonyl group, wherein $R_2$ and $R_4$ may be bound to each other to form an aliphatic ring. $R_6$ represents a hydrogen atom, an alkyl group, an alkoxy group, or a halogen atom; $R_7$ and $R_8$ each independently represent a hydrogen atom, an alkyl group, or an aryl group; $R_9$ represents a dicyanomethylene group, a cyanocarboxymethylene group, or any one of the following general formulas (2) to (4); $Y_1$ represents a carbon atom having aryl group, a cyclopentene ring, a cyclohexene ring or a carbon atom (—C═); and n represents an integer of 0 to 1.

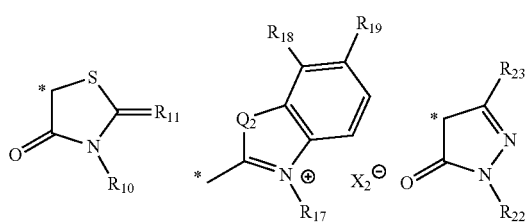

General Formula (2) General Formula (3) General Formula (4)

In general formula (2), $R_{10}$ represents an alkyl group, a carboxylalkyl group, an alkoxycarbonylalkyl group, or an alkylcarbonyloxyalkyl group; and $R_{11}$ represents a sulfur atom, a 2-thioxothiazolidin-4-one group, a thiazoline-2,4-one group, or the following general formula (5). A sign "*" represents a binding site.

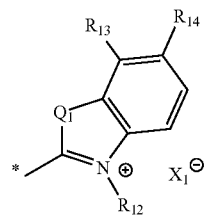

General Formula (5)

In general formula (5), $R_{12}$ represents an alkyl group, a carboxylalkyl group, an alkoxycarbonylalkyl group, or an alkylcarbonyloxyalkyl group; and $R_{13}$ and $R_{14}$ each represent a hydrogen atom and may be bound to each other to form a benzene ring. $Q_1$ represents an oxygen atom, a sulfur atom, a N-alkyl nitrogen atom, or —C($R_{15}$)($R_{16}$)—, wherein $R_{15}$ and $R_{16}$ each independently represent an alkyl group and may be bound to each other to form a ring; and $X_1^-$ represents an anionic group. A sign "*" represents a binding site.

In general formula (3), $R_{17}$ represents an alkyl group, a carboxylalkyl group, an alkoxycarbonylalkyl group, or an alkylcarbonyloxyalkyl group; and $R_{18}$ and $R_{19}$ each represent a hydrogen atom and may be bound to each other to form a benzene ring. $Q_2$ represents an oxygen atom, a sulfur atom, a N-alkyl nitrogen atom, or —C($R_{20}$)($R_{21}$)—, wherein $R_{20}$ and $R_{21}$ each independently represent an alkyl group and may be bound to each other to form a ring; and $X_2^-$ represents an anionic group. A sign "*" represents a binding site. In general formula (4), $R_{22}$ represents an alkyl group or an aryl group; and $R_{23}$ represents an alkyl group or a carboxyl group. A sign "*" represents a binding site.

In general formula (1), the alkyl group used as $R_1$ is not especially limited, and examples include linear, branched or cyclic alkyl groups having 1 to 20 carbon atoms, such as a methyl group, an ethyl group, a propyl group, a butyl group, an ethylhexyl group, and a cyclohexyl group.

In general formula (1), the aralkyl group used as $R_1$ is not especially limited, and examples include a benzyl group and a phenethyl group.

In general formula (1), the alkenyl group used as $R_1$ is not especially limited, and examples include alkenyl groups having 2 to 20 carbon atoms, such as a vinyl group, a 2,2-diphenylvinyl group, a 3-butenyl group, and a cyclohexenyl group.

In general formula (1), the aryl group used as $R_1$ is not especially limited, and examples include 6- to 14-membered monocyclic or polycyclic aryl groups, such as a phenyl group, a naphthyl group, a phenanthryl group, and an anthracenyl group.

In general formula (1), $R_1$ may further have a substituent and the substituent is not especially limited as long as the storage stability of the dye compound is not largely inhibited, and examples include alkyl groups such as a methyl group, an ethyl group, a n-propyl group, an isopropyl group, a n-butyl group, an isobutyl group, a sec-butyl group and a tert-butyl group; aryl groups such as a phenyl group and a naphthyl group; alkoxy groups such as a methoxy group, an ethoxy group and a butoxy group; aryloxy groups such as a phenoxy group and a naphthyloxy group; alkylsulfanyl groups such as a thiomethyl group, a thioethyl group, a thiopropyl group, a thiobutyl group and a thiophenyl group; di-substituted amino groups such as a dimethylamino group, a N-ethyl-N-phenylamino group, and a diphenylamino group; acyl groups such as an acetyl group and a benzoyl group; a sulfonyl group; a carboxyl group; a carboxyalkyl group; a carbamoyl group; a sulfamoyl group; hetero ring groups such as a pyridyl group, a triazinyl group, and a benzothiazolyl group; a nitro group; and halogen atoms such as a fluorine atom, a chlorine atom, a bromine atom and an iodine atom.

In general formula (1), $R_1$ can be arbitrarily and independently selected from the aforementioned substituents, and in a preferred aspect, $R_1$ represents an alkyl group, an aryl group or the like because a subtype can be easily identified in this case. Specifically, $R_1$ represents preferably a methyl group, an ethyl group, a propyl group, a butyl group, a phenyl group, a bromophenyl group, a benzyl group, a bromobenzyl group, a methylthiophenyl group, a methoxyphenyl group, a methoxynaphthyl group, a benzylphenyl group, a 2,2-diphenylvinyl group or a 2,2-diphenylvinylphenyl group. More preferably, $R_1$ represents a phenyl group, a bromophenyl group, a benzyl group, a methylthiophenyl group, a methoxyphenyl group or a methoxynaphthyl group, and $R_1$ particularly preferably represents a methylthiophenyl group because a subtype can be easily identified based on a large stokes shift in this case.

In general formula (1), the alkyl group used as $R_2$ to $R_5$ is not especially limited, and examples include alkyl groups having 1 to 4 carbon atoms, such as a methyl group, an ethyl group, a propyl group and a butyl group.

In general formula (1), the aryl group used as $R_2$ to $R_5$ is not especially limited, and examples include a phenyl group and a naphthyl group.

In general formula (1), the carboxylalkyl group used as $R_2$ to $R_5$ is not especially limited, and examples include a methyl carboxylate group, an ethyl carboxylate group, a propyl carboxylate group and a butyl carboxylate group.

In general formula (1), the alkylcarbonyl group used as $R_2$ to $R_5$ is not especially limited, and examples include a methylcarbonyl group, an ethylcarbonyl group, a propylcarbonyl group, a butylcarbonyl group, a phenylcarbonyl group, a naphthylcarbonyl group, and a phenanthrylcarbonyl group.

In general formula (1), the aliphatic ring formed when $R_2$ and $R_4$ are bound to each other is not especially limited, and examples include saturated aliphatic rings such as a cyclooctane ring, a cycloheptane ring, a cyclohexane ring, a cyclopentane ring, and a cyclobutane ring; and partially saturated aliphatic rings such as a cyclopentene ring and a cyclohexene ring. The ring may further have a substituent and the substituent is not especially limited as long as the identification of a subtype is not largely inhibited. Examples of such a substituent include alkyl groups such as a methyl group, an ethyl group, a n-propyl group, an isopropyl group and a butyl group; aryl groups such as a phenyl group; alkoxy groups such as a methoxy group, an ethoxy group and a butoxy group; aryloxy groups such as a phenoxy group; di-substituted amino groups such as a dimethylamino group, a N-ethyl-N-phenylamino group, and a diphenylamino group; acyl groups such as an acetyl group and a benzoyl group; a sulfonyl group; a carboxyl group; a carboxylalkyl group; a carbamoyl group; a sulfamoyl group; hetero ring groups such as a pyridyl group, a triazinyl group, and a benzothiazolyl group; a nitro group; and halogen atoms such as a fluorine atom, a chlorine atom, a bromine atom and an iodine atom; a carboxyl group, and a sulfo group.

In general formula (1), in a preferred aspect, $R_2$ to $R_5$ each independently represent a hydrogen atom, an alkyl group or an aryl group and $R_2$ and $R_4$ are bound to each other to form an aliphatic ring, and in a more preferred aspect, $R_2$ and $R_4$ are bound to each other to form an aliphatic ring, because a subtype can be easily identified in such a case. Specifically, the aliphatic ring can be a cyclooctane ring, a cycloheptane ring, a cyclohexane ring, a cyclopentane ring or a cyclobutane ring. More preferably, the aliphatic ring is a cyclopentane ring.

In general formula (1), the alkyl group used as $R_6$ is not especially limited, and examples include a methyl group, an ethyl group, a propyl group and a butyl group.

In general formula (1), the alkoxy group used as $R_6$ is not especially limited, and examples include a methoxy group, an ethoxy group, a propoxy group and a butoxy group.

In general formula (1), examples of the halogen atom used as $R_6$ include a fluorine atom, a chlorine atom, a bromine atom and an iodine atom.

In general formula (1), $R_6$ preferably represents a hydrogen atom, a halogen atom or an alkoxy group, and more preferably represents a hydrogen atom or a bromine atom.

In general formula (1), the alkyl group used as $R_7$ and $R_8$ is not especially limited, and examples include alkyl groups having 1 to 4 carbon atoms, such as a methyl group, an ethyl group, a propyl group and a butyl group.

In general formula (1), the aryl group used as $R_7$ and $R_8$ is not especially limited, and examples include a phenyl group and a methylphenyl group.

In general formula (1), the carbon atom having aryl group used as $Y_1$ is not especially limited, and examples include phenyl-substituted carbon, methylphenyl-substituted carbon, methoxyphenyl-substituted carbon, and chlorophenyl-substituted carbon.

In general formula (1), $R_9$ represents a dicyanomethylene group, a cyanocarboxymethylene group, or any one of the following general formulas (2) to (4), and the sign "*" represents a binding site.

$R_9$ preferably represents any one of general formulas (2) to (4), and particularly preferably represents general formula (2) because a subtype can be easily identified in this case.

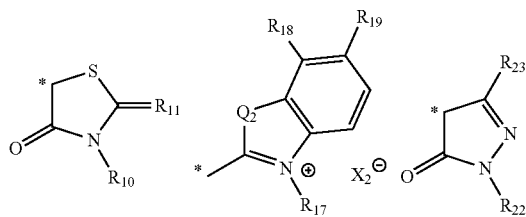

General Formula (2) General Formula (3) General Formula (4)

In general formula (2), the alkyl group used as $R_{10}$ is not especially limited, and examples include linear, branched or cyclic alkyl groups having 1 to 20 carbon atoms, such as a methyl group, an ethyl group, a propyl group, a butyl group, an ethylhexyl group, and a cyclohexyl group.

In general formula (2), the carboxylalkyl group used as $R_{10}$ is not especially limited, and examples include a carboxymethyl group, a carboxyethyl group, a carboxypropyl group, a carboxybutyl group, a carboxypentyl group, a carboxyhexyl group, a carboxyheptyl group and a carboxyoctyl group.

In general formula (2), the alkoxycarbonylalkyl group used as $R_{10}$ is not especially limited, and examples include a methoxycarbonylmethyl group, a methoxycarbonylethyl group, an ethoxycarbonylethyl group, a butoxycarbonylethyl group, a methoxycarbonylpropyl group, and a methoxycarbonylhexyl group.

In general formula (2), the alkylcarbonyloxyalkyl group used as $R_{10}$ is not especially limited, and examples include a methylcarbonyloxymethyl group, an ethylcarbonyloxymethyl group, an ethylcarbonyloxyethyl group, ethylcarbonyloxybutyl, and a proxycarbonyloxymethyl group.

In general formula (2), the 2-thioxothiazolin-4-one group used as $R_{11}$ is not especially limited, and examples include the following compounds.

The sign "*" represents a binding site.

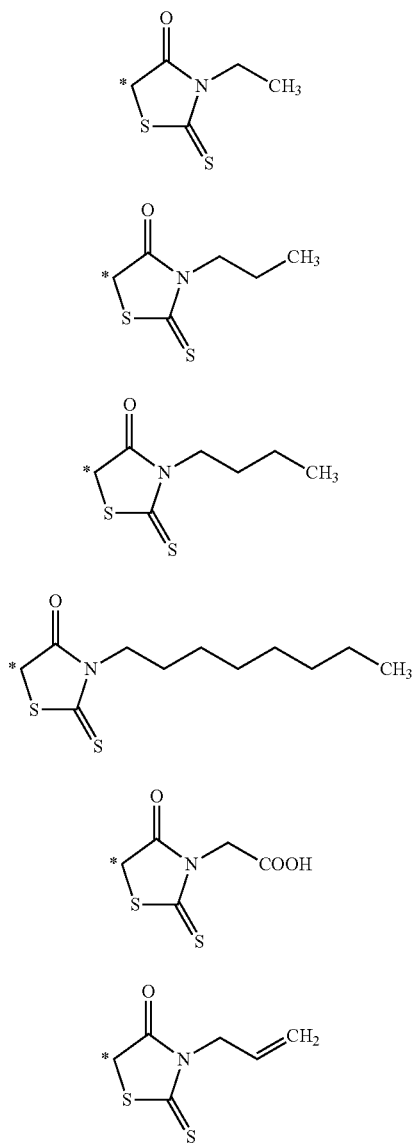

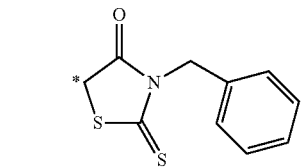

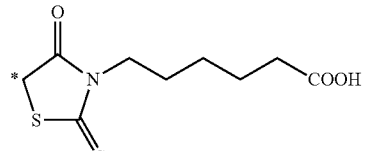

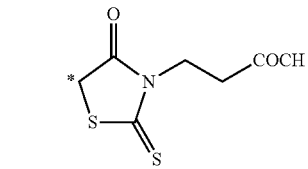

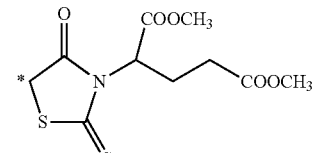

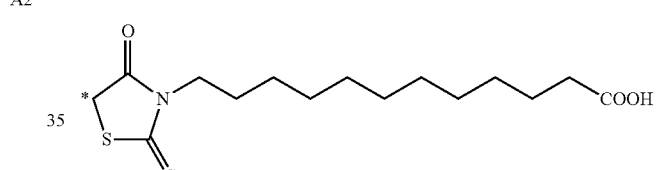

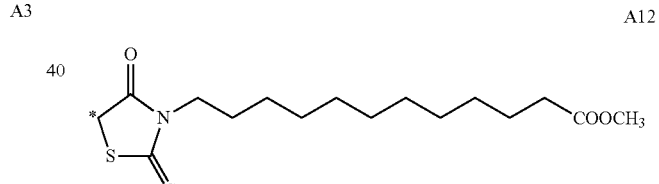

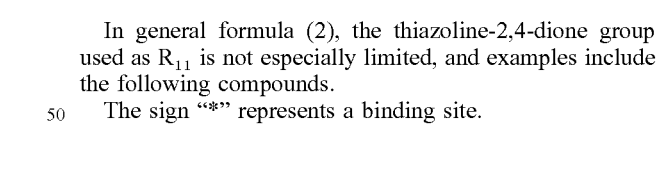

In general formula (2), the thiazoline-2,4-dione group used as $R_{11}$ is not especially limited, and examples include the following compounds.

The sign "*" represents a binding site.

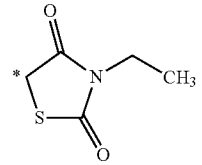

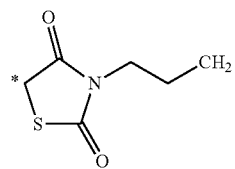

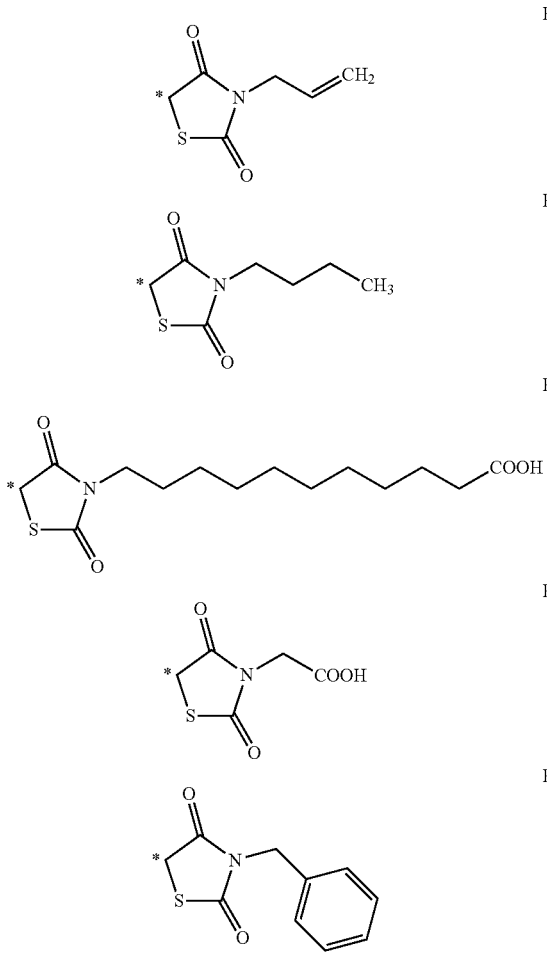

In general formula (2), $R_{11}$ can be represented by the following general formula (5):

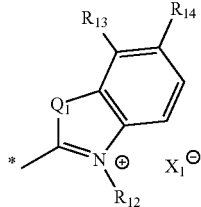

General formula (5)

In general formula (5), the alkyl group used as $R_{12}$ is not especially limited, and examples include linear, branched or cyclic alkyl groups having 1 to 20 carbon atoms, such as a methyl group, an ethyl group, a propyl group, a butyl group, an ethylhexyl group and a cyclohexyl group.

In general formula (5), the carboxylalkyl group used as $R_{12}$ is not especially limited, and examples include a carboxymethyl group, a carboxyethyl group, a carboxypropyl group, a carboxybutyl group, a carboxypentyl group, a carboxyhexyl group, a carboxyheptyl group and a carboxyoctyl group.

In general formula (5), the alkoxycarbonylalkyl group used as $R_{12}$ is not especially limited, and examples include a methoxycarbonylmethyl group, a methoxycarbonylethyl group, an ethoxycarbonylethyl group, a butoxycarbonylethyl group, a methoxycarbonylpropyl group, and a methoxycarbonylhexyl group.

In general formula (5), the alkylcarbonyloxyalkyl group used as $R_{12}$ is not especially limited, and examples include a methylcarbonyloxymethyl group, an ethylcarbonyloxymethyl group, an ethylcarbonyloxyethyl group, ethylcarbonylbutyl, and a proxycarbonyloxymethyl group.

In general formula (5), $R_{13}$ and $R_{14}$ are bound to each other to form a benzene ring, and the ring may further have a substituent.

In general formula (5), the N-alkyl nitrogen atom used as $Q_1$ is not especially limited, and examples include a N-methyl nitrogen atom, a N-ethyl nitrogen atom, a N-propyl nitrogen atom, and a N-butyl nitrogen atom.

In general formula (5), the alkyl group used as $R_{15}$ and $R_{16}$ of $Q_1$ is not especially limited, and examples include alkyl groups having 1 to 4 carbon atoms, such as a methyl group, an ethyl group, a propyl group and a butyl group.

In general formula (5), the ring formed when $R_{15}$ and $R_{16}$ are bound to each other is not especially limited, and examples include a cyclopentane ring and a cyclohexane ring.

In general formula (5), the anionic group represented by $X_1^-$ is not especially limited, and examples include a chloride ion, a bromide ion, an iodide ion, a sulfate ion, a nitrate ion, a methanesulfonate ion, a p-toluenesulfonate ion, a tetrafluoroborate ion, and a hexafluorophosphate ion.

In general formula (3), the alkyl group used as $R_{17}$ is not especially limited, and examples include linear, branched or cyclic alkyl groups having 1 to 20 carbon atoms, such as a methyl group, an ethyl group, a propyl group, a butyl group, an ethylhexyl group and a cyclohexyl group.

In general formula (3), the carboxylalkyl group used as $R_{17}$ is not especially limited, and examples include a carboxymethyl group, a carboxyethyl group, and a carboxypropyl group.

In general formula (3), the alkoxycarbonylalkyl group used as $R_{17}$ is not especially limited, and examples include a methoxycarbonylmethyl group, a methoxycarbonylethyl group, an ethoxycarbonylethyl group, a butoxycarbonylethyl group, and a methoxycarbonylpropyl group.

In general formula (3), the alkylcarbonyloxyalkyl group used as $R_{17}$ is not especially limited, and examples include a methylcarbonyloxymethyl group, an ethylcarbonyloxymethyl group, an ethylcarbonyloxyethyl group, ethylcarbonylbutyl, and a proxycarbonyloxymethyl group.

In general formula (3), $R_{18}$ and $R_{19}$ are bound to each other to form a benzene ring, and the ring may further have a substituent.

In general formula (3), the N-alkyl nitrogen atom used as $Q_2$ is not especially limited, and examples include a N-methyl nitrogen atom, a N-ethyl nitrogen atom, a N-propyl nitrogen atom, and a N-butyl nitrogen atom.

In general formula (3), the alkyl group used as $R_{20}$ and $R_{21}$ of $Q_2$ is not especially limited, and examples include alkyl groups having 1 to 4 carbon atoms, such as a methyl group, an ethyl group, a propyl group and a butyl group.

In general formula (3), the ring formed when $R_{20}$ and $R_{21}$ are bound to each other is not especially limited, and examples include a cyclopentane ring and a cyclohexane ring.

In general formula (3), the anionic group represented by $X_2^-$ is not especially limited, and examples include a chloride ion, a bromide ion, an iodide ion, a sulfate ion, a nitrate ion, a methanesulfonate ion, a p-toluenesulfonate ion, a tetrafluoroborate ion, and a hexafluorophosphate ion.

In general formula (4), the alkyl group used as $R_{22}$ is not especially limited, and examples include linear, branched or cyclic alkyl groups having 1 to 20 carbon atoms, such as a methyl group, an ethyl group, a propyl group, a butyl group, an ethylhexyl group and a cyclohexyl group.

In general formula (4), the aryl group used as $R_{22}$ is not especially limited, and examples include 6- to 14-membered monocyclic or polycyclic aryl groups, such as a phenyl group, a naphthyl group, a phenanthryl group, and an anthracenyl group.

In general formula (4), the aryl group used as $R_{22}$ may further have a substituent, and the substituent is not especially limited as long as the identification of a subtype is not largely inhibited. Examples include alkyl groups such as a methyl group, an ethyl group, a n-propyl group, an isopropyl group, a n-butyl group, an isobutyl group, a sec-butyl group and a tert-butyl group; aryl groups such as a phenyl group and a naphthyl group; alkoxy groups such as a methoxy group, an ethoxy group and a butoxy group; aryloxy groups such as a phenoxy group and a naphthyloxy group; alkylsulfanyl groups such as a thiomethyl group, a thioethyl group, a thiopropyl group, a thiobutyl group and a thiophenyl group; di-substituted amino groups such as a dimethylamino group, a N-ethyl-N-phenylamino group, and a diphenylamino group; acyl groups such as an acetyl group and a benzoyl group; a sulfonyl group; a carboxyl group; a carboxylalkyl group; a carbamoyl group; a sulfamoyl group; hetero ring groups such as a pyridyl group, a triazinyl group, and a benzothiazolyl group; a nitro group; and halogen atoms such as a fluorine atom, a chlorine atom, a bromine atom and an iodine atom.

In general formula (4), the alkyl group used as $R_{23}$ is not especially limited, and examples include linear, branched or cyclic alkyl groups having 1 to 20 carbon atoms, such as a methyl group, an ethyl group, a propyl group, a butyl group, an ethylhexyl group and a cyclohexyl group.

<Regarding Compounds>

The compounds represented by general formula (1) of the present embodiment can be easily synthesized by a method similar to known methods (PTL 2 and the like).

Suitable specific examples of the compounds represented by general formula (1) of the present invention include, but are not limited to, the following compounds (1) to (85):

Compound (1)

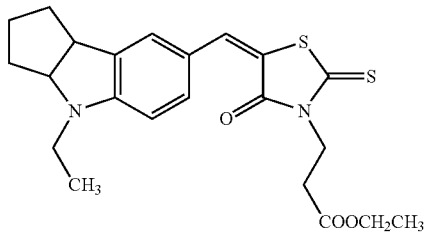

Compound (2)

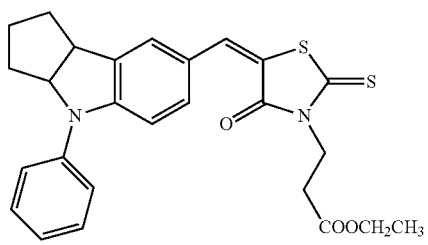

Compound (3)

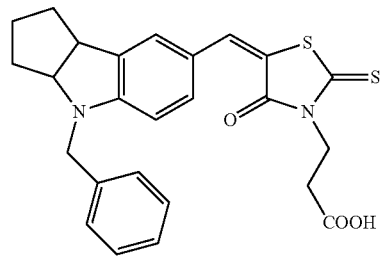

Compound (4)

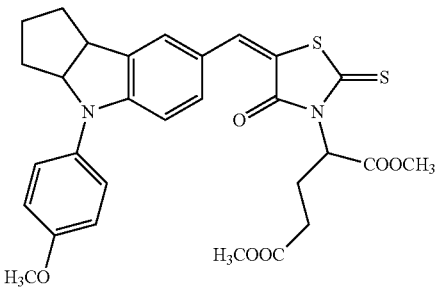

Compound (5)

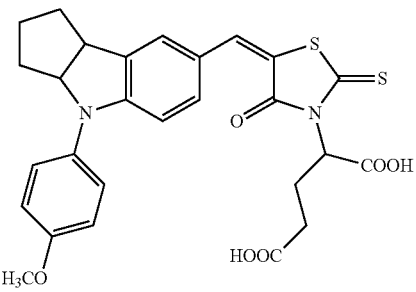

Compound (6)

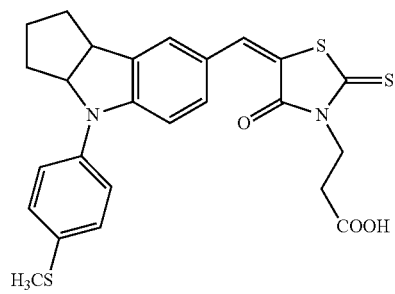

Compound (7)

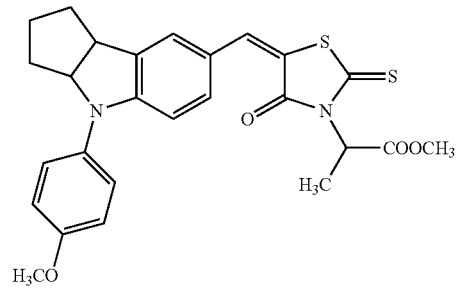

-continued
Compound (8)
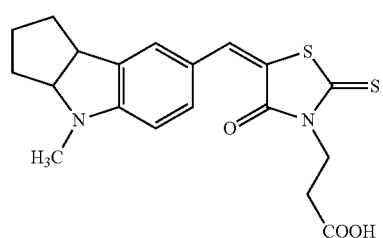
Compound (9)
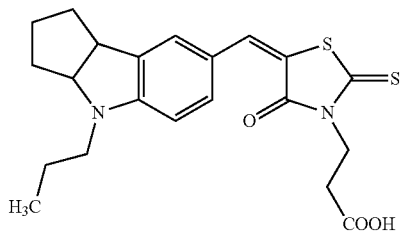
Compound (10)
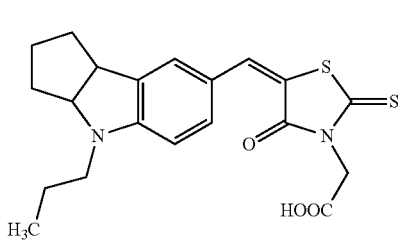
Compound (11)
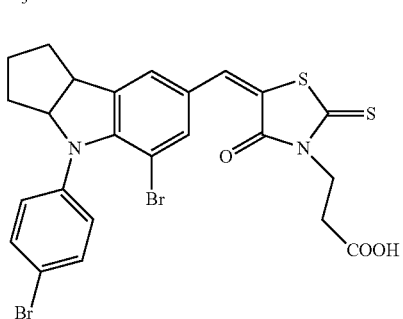
Compound (12)
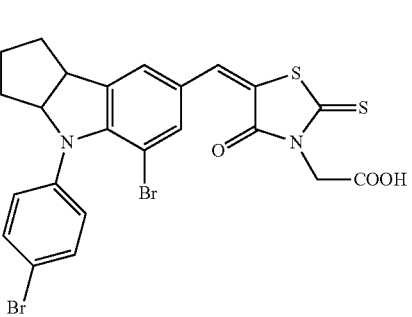
Compound (13)
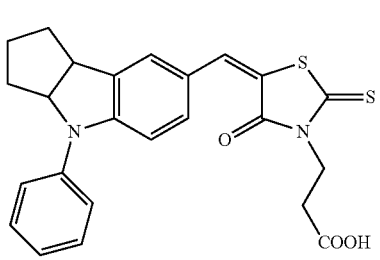
-continued
Compound (14)
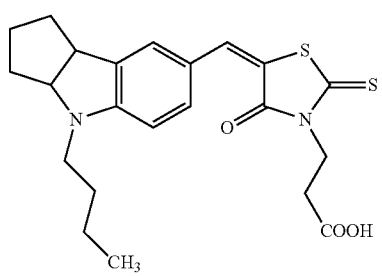
Compound (15)
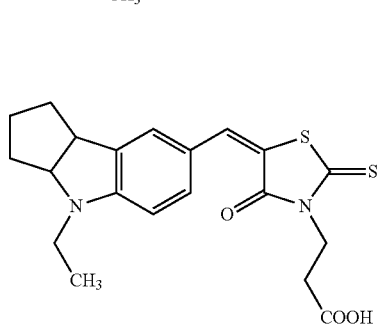
Compound (16)
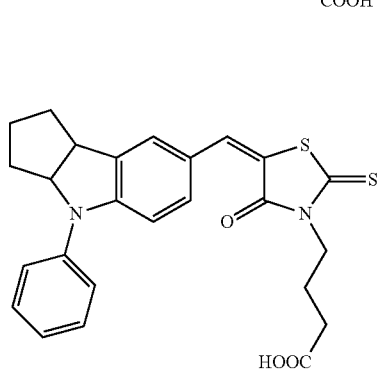
Compound (17)
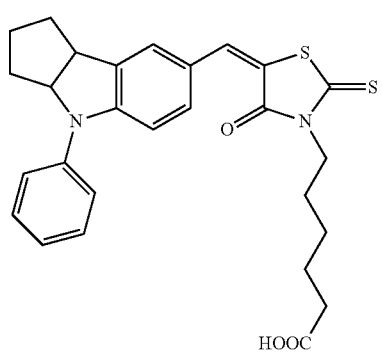
Compound (18)
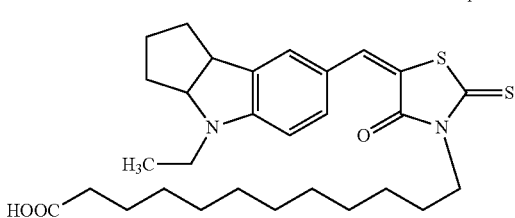

Compound (19)
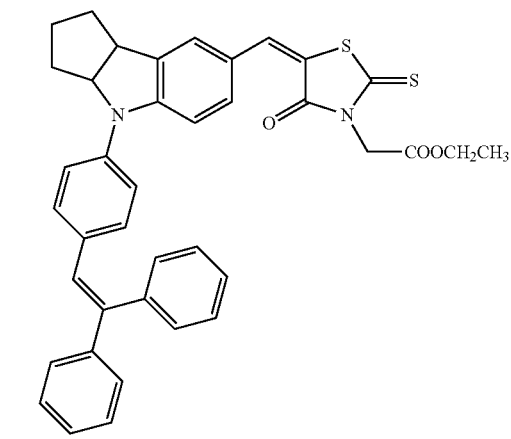
Compound (20)
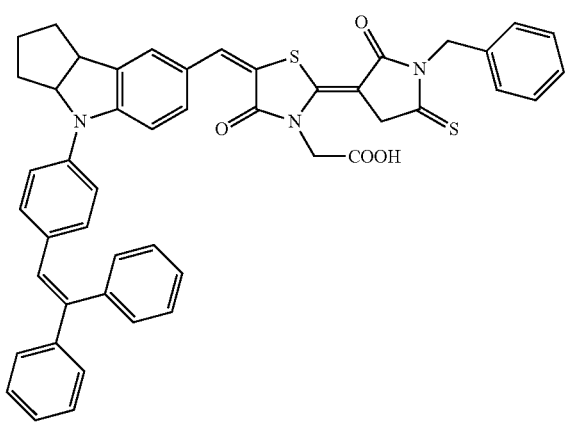
Compound (21)
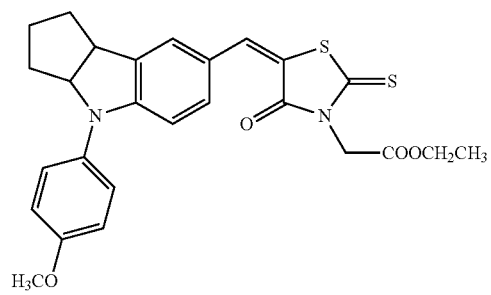
Compound (22)
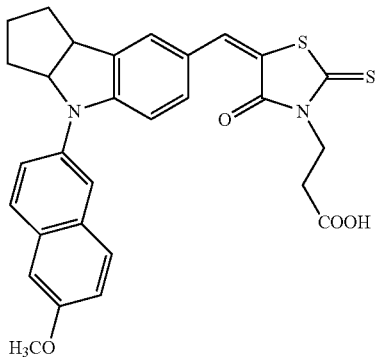
Compound (23)
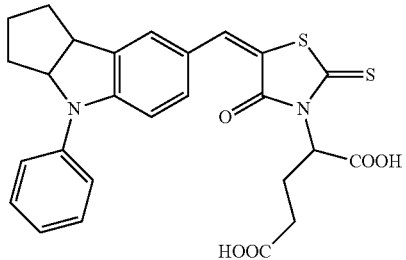
Compound (24)
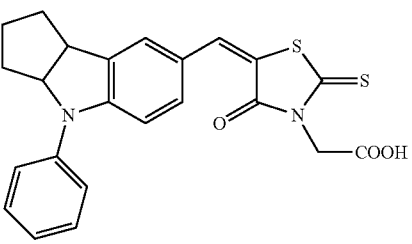
Compound (25)
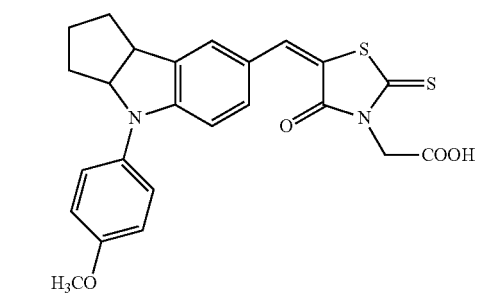
Compound (26)
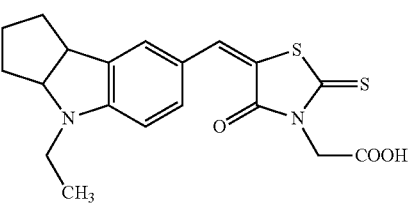
Compound (27)
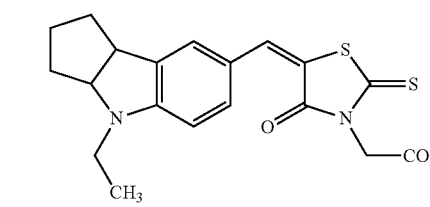
Compound (28)
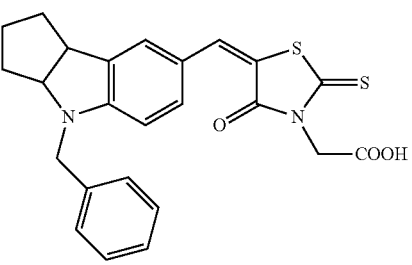

Compound (29)
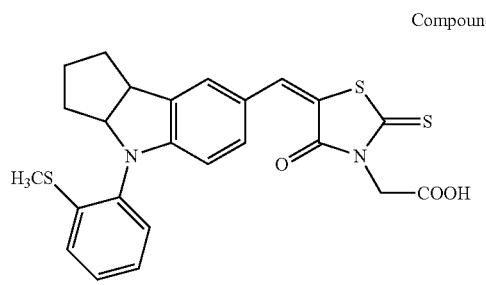
Compound (30)
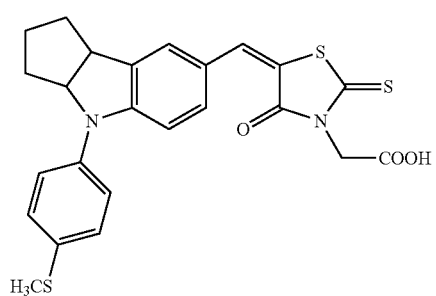
Compound (31)
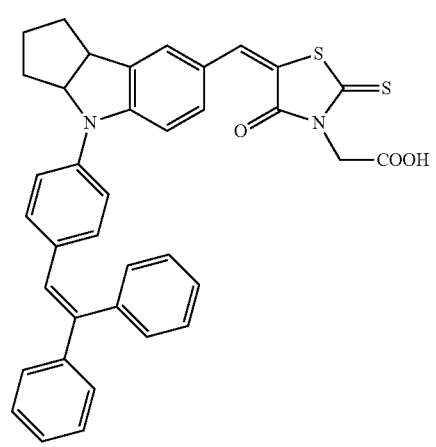
Compound (32)
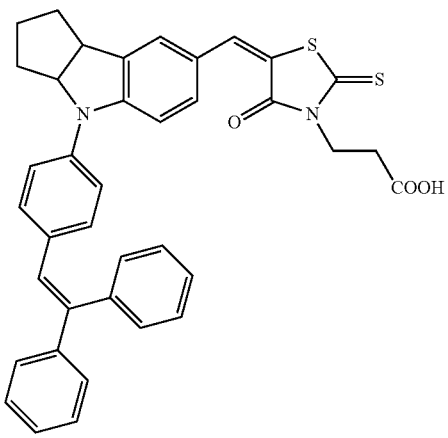
Compound (33)
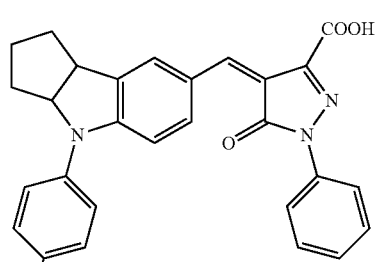
Compound (34)
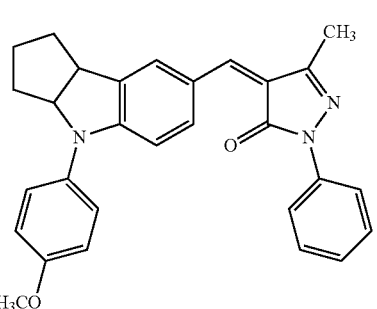
Compound (35)
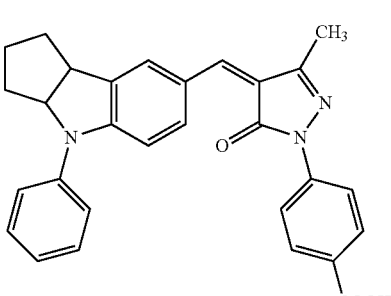
Compound (36)
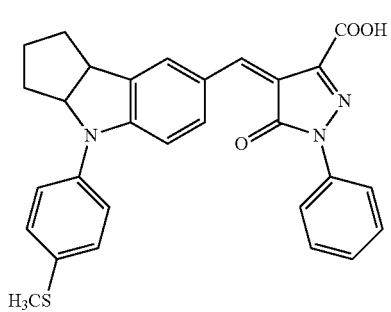
Compound (37)

-continued
Compound (38)
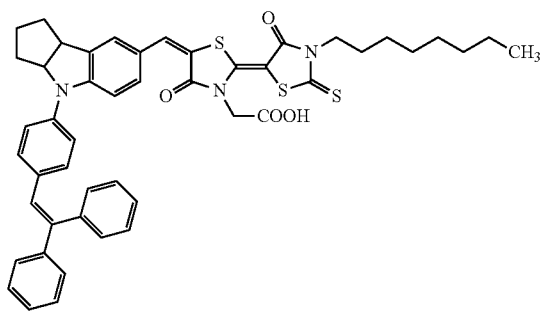
Compound (39)
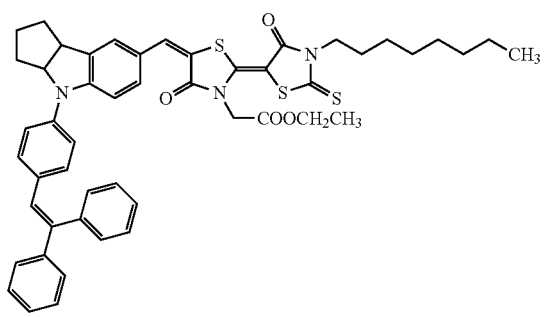
Compound (40)
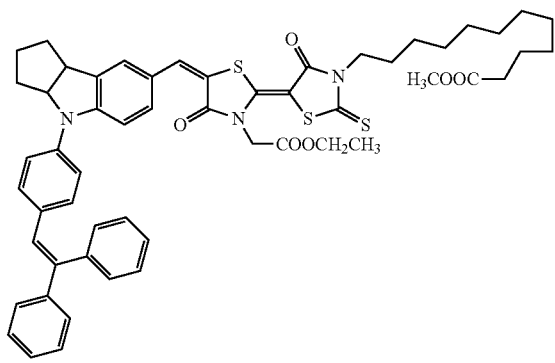
Compound (41)
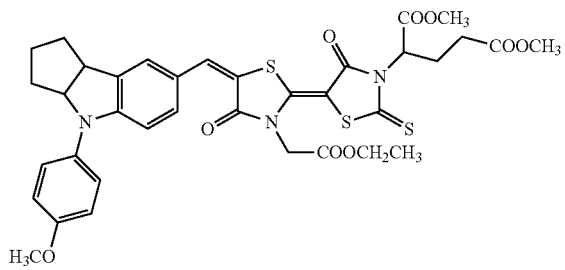
Compound (42)
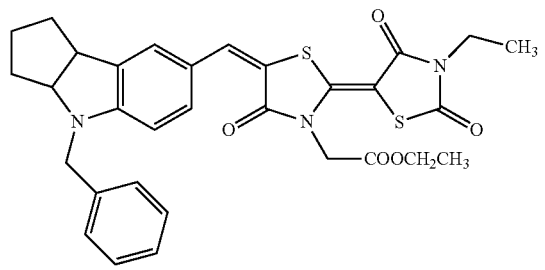
-continued
Compound (43)
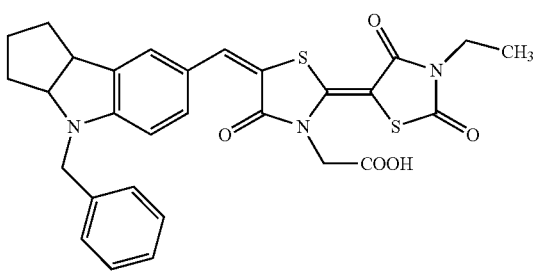
Compound (44)
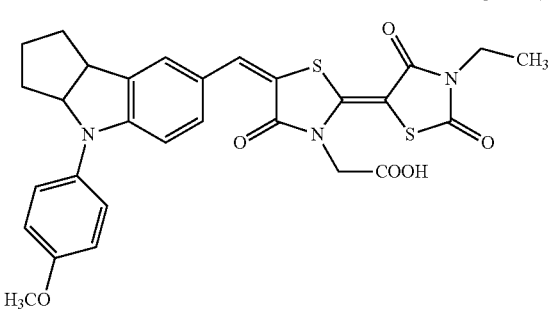
Compound (45)
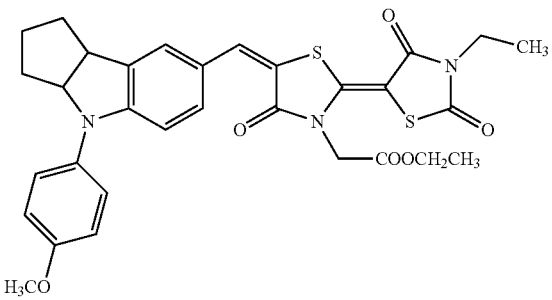
Compound (46)
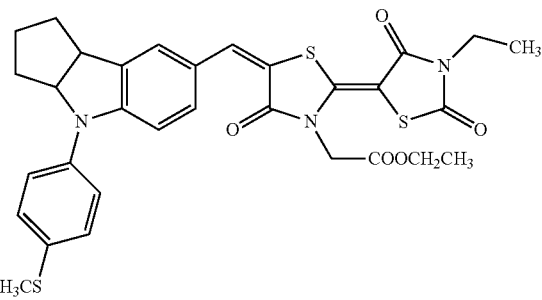
Compound (47)
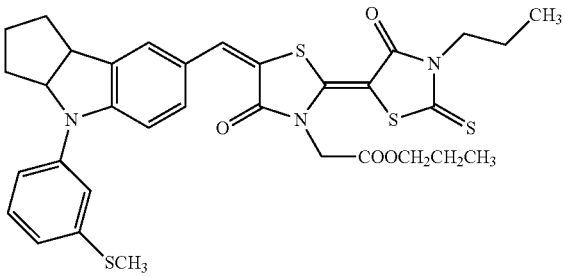

Compound (48)
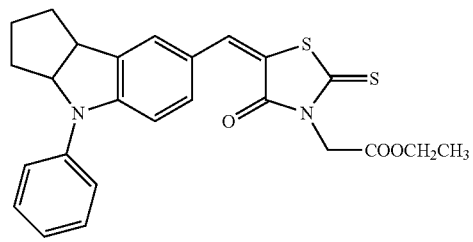
Compound (49)
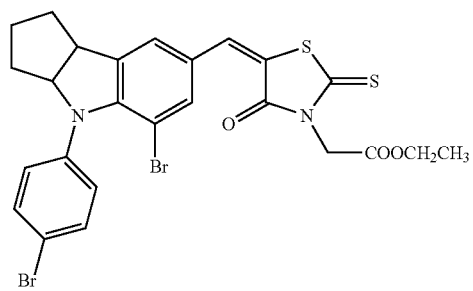
Compound (50)
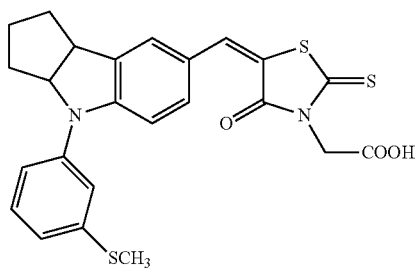
Compound (51)
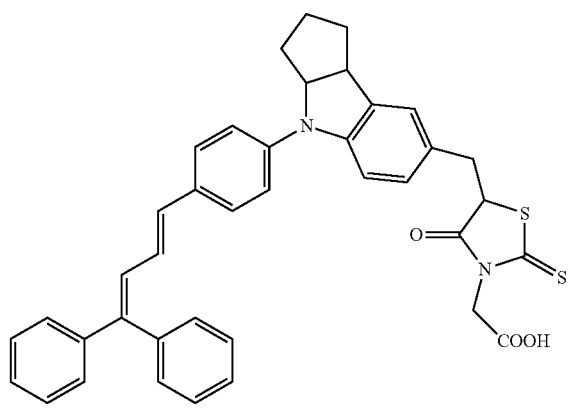
Compound (52)
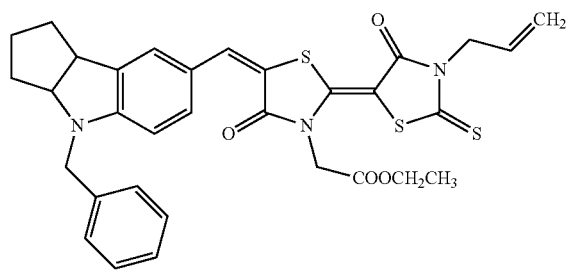
Compound (53)
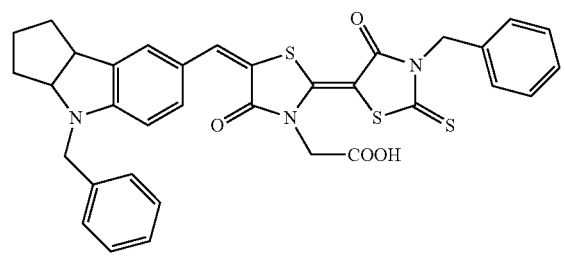
Compound (54)
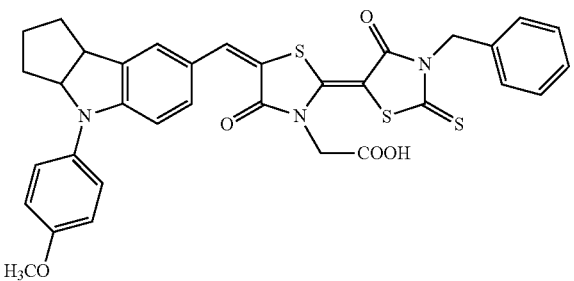
Compound (55)
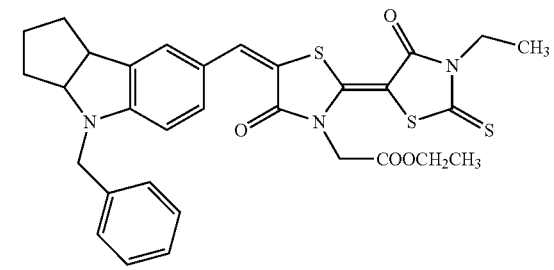
Compound (56)
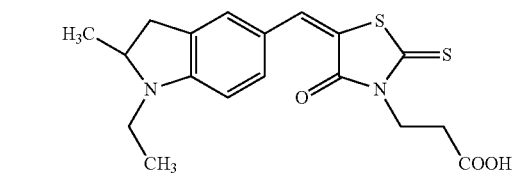
Compound (57)
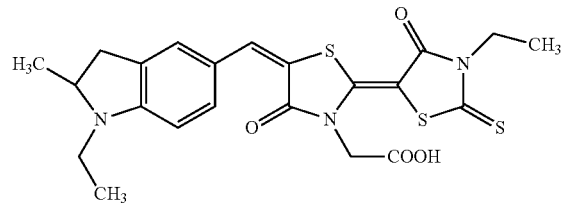

-continued
Compound (58)
Compound (59)
Compound (60)
Compound (61)
Compound (62)
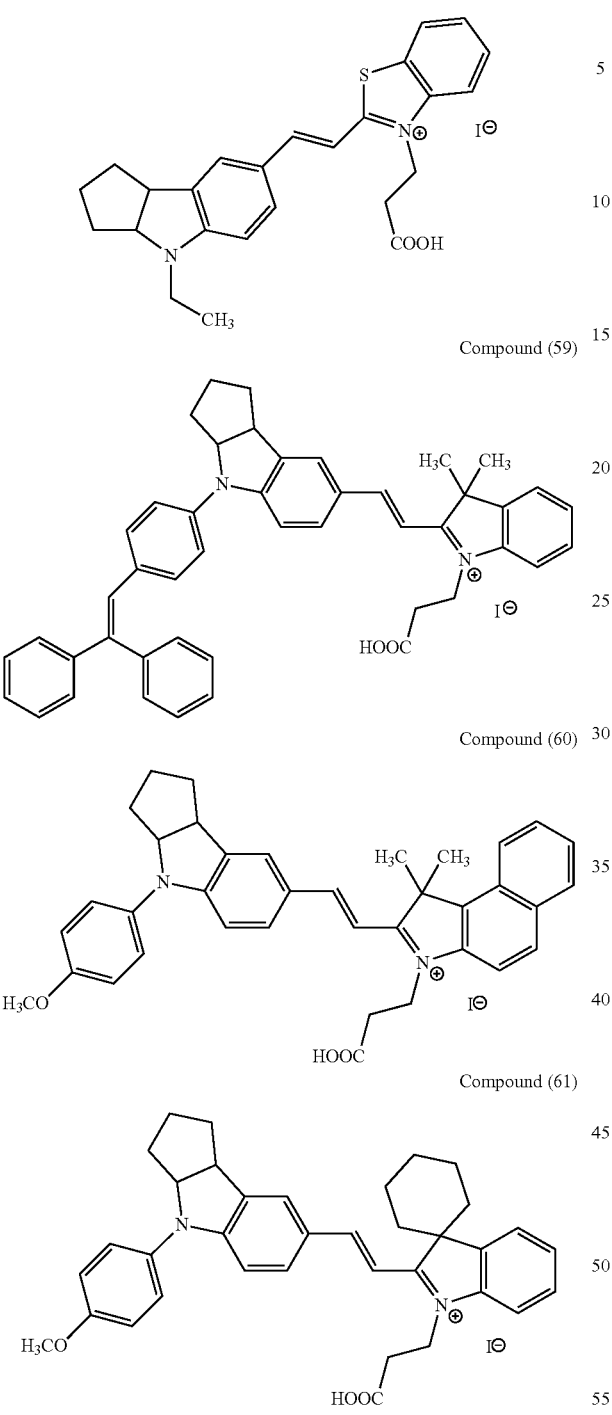
-continued
Compound (63)
Compound (64)
Compound (65)
Compound (66)
Compound (67)
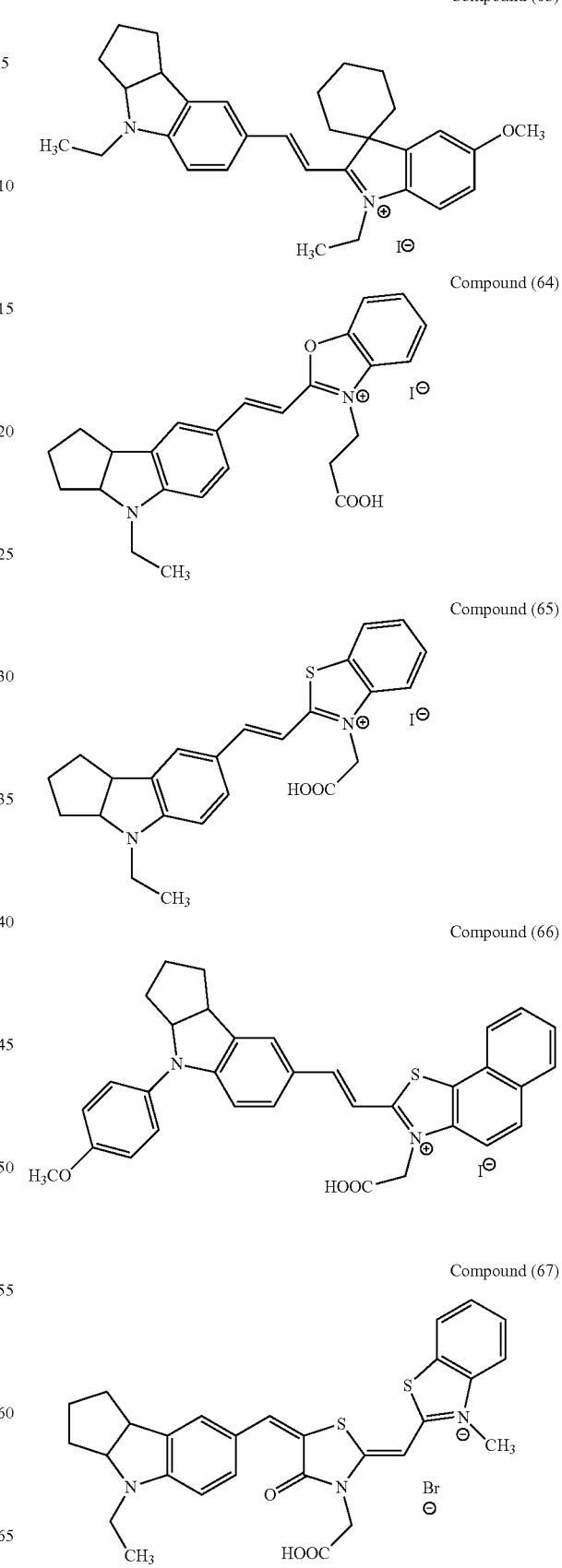

Compound (68)
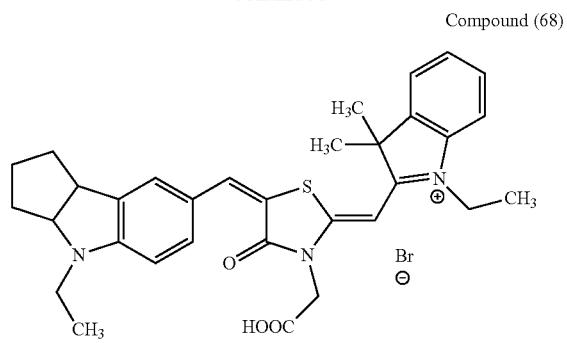
Compound (69)
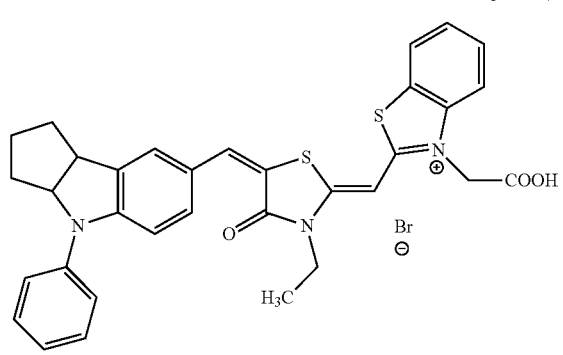
Compound (70)
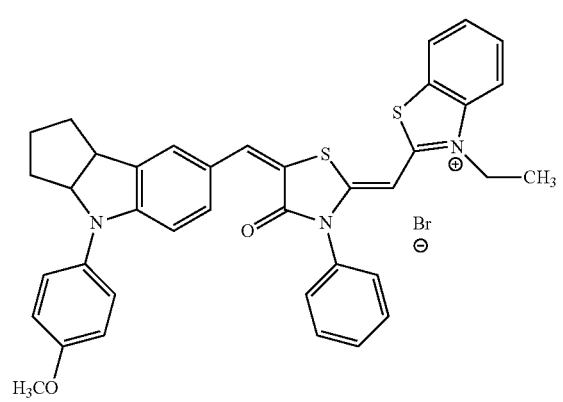
Compound (71)
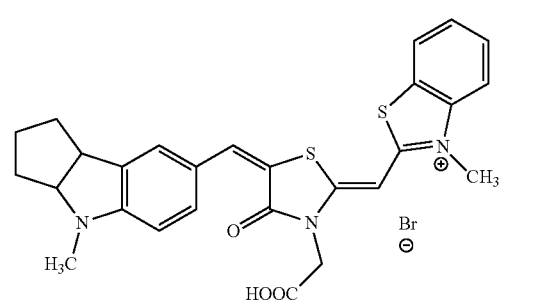
Compound (72)
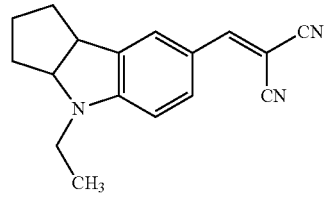
Compound (73)
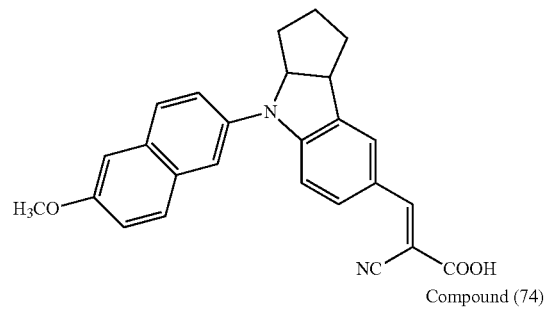
Compound (74)
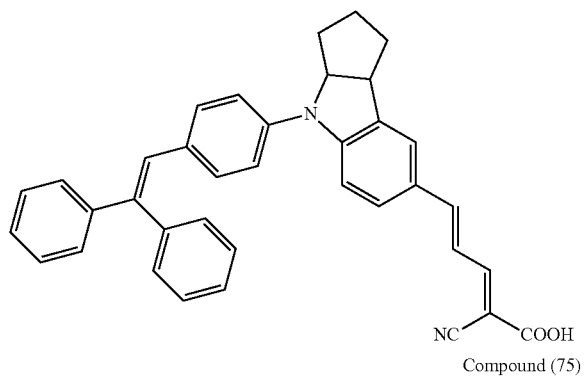
Compound (75)
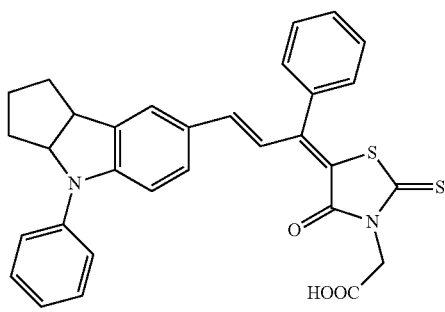
Compound (76)
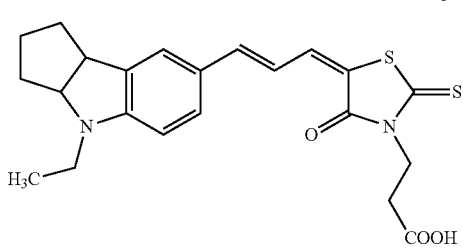
Compound (77)
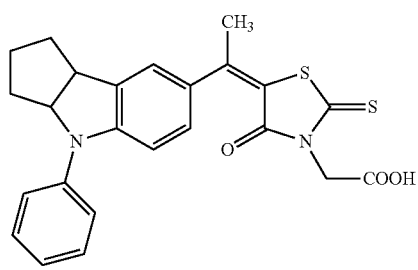

Compound (78)
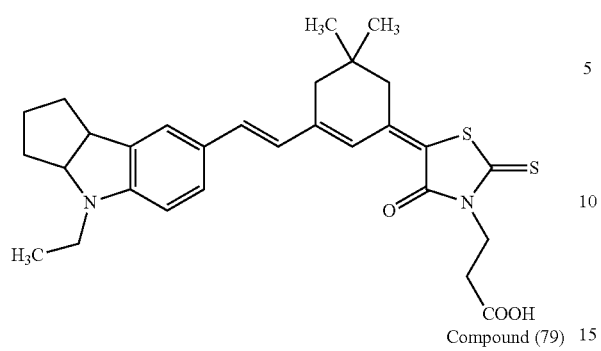

Compound (79)
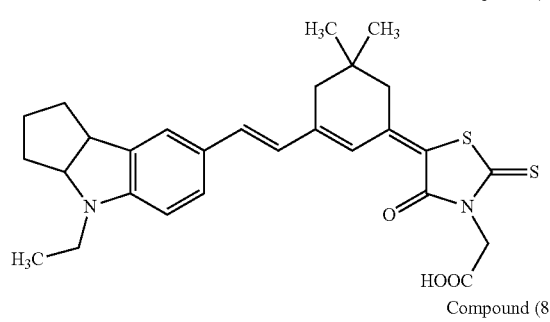

Compound (80)
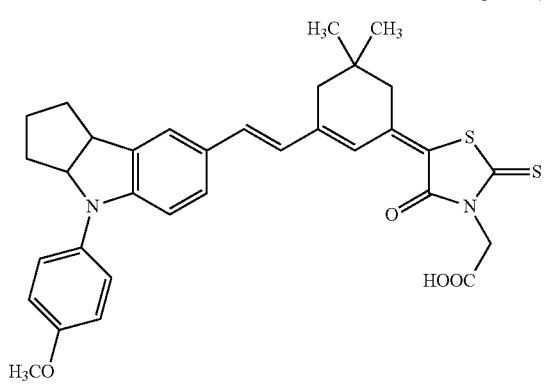

Compound (81)
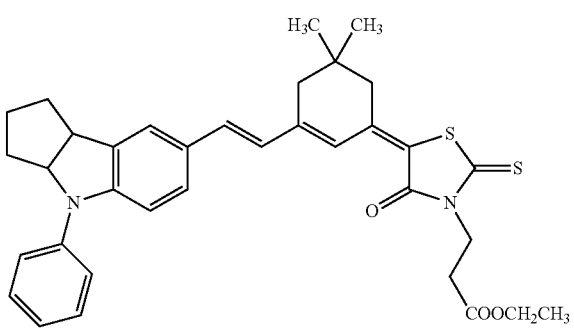

Compound (82)
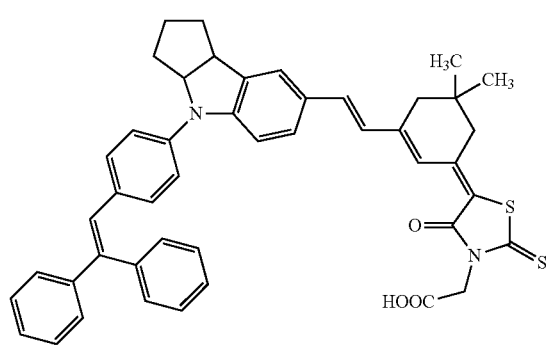

Compound (83)
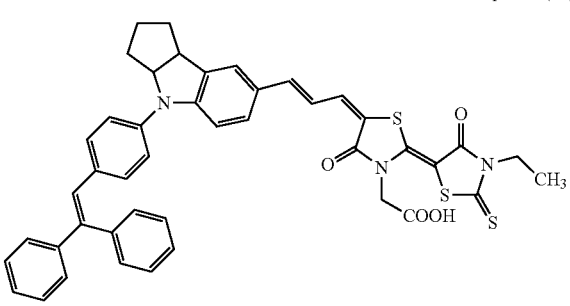

Compound (84)
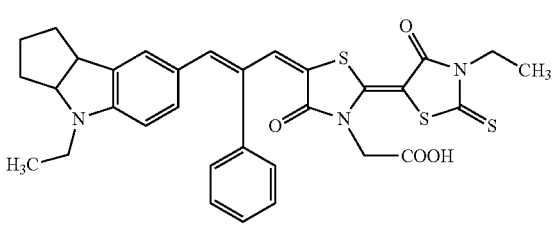

Compound (85)
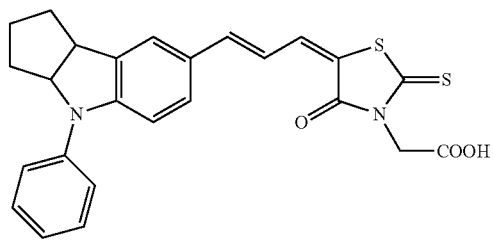

Substituents used in general formula (1) of the compounds (1) to (85) are shown in Table 1.

TABLE 1

| Compound | R1 | R2 | R3 | R4 | R5 | R6 | R7 | R8 | Y1 | n | R9 |
|---|---|---|---|---|---|---|---|---|---|---|---|
| (1) | Alkyl group | | Aliphatic ring | | | Hydrogen atom | Hydrogen atom | — | — | 0 | General formula (2) |
| (2) | Aryl group | | Aliphatic ring | | | Hydrogen atom | Hydrogen atom | — | — | 0 | General formula (2) |
| (3) | Aralkyl group | | Aliphatic ring | | | Hydrogen atom | Hydrogen atom | — | — | 0 | General formula (2) |

TABLE 1-continued

| Compound | R1 | R2 | R3 | R4 | R5 | R6 | R7 | R8 | Y1 | n | R9 |
|---|---|---|---|---|---|---|---|---|---|---|---|
| (4) | Aryl group | Aliphatic ring | | | | Hydrogen atom | Hydrogen atom | — | — | 0 | General formula (2) |
| (5) | Aryl group | Aliphatic ring | | | | Hydrogen atom | Hydrogen atom | — | — | 0 | General formula (2) |
| (6) | Aryl group | Aliphatic ring | | | | Hydrogen atom | Hydrogen atom | — | — | 0 | General formula (2) |
| (7) | Aryl group | Aliphatic ring | | | | Hydrogen atom | Hydrogen atom | — | — | 0 | General formula (2) |
| (8) | Alkyl group | Aliphatic ring | | | | Hydrogen atom | Hydrogen atom | — | — | 0 | General formula (2) |
| (9) | Alkyl group | Aliphatic ring | | | | Hydrogen atom | Hydrogen atom | — | — | 0 | General formula (2) |
| (10) | Alkyl group | Aliphatic ring | | | | Hydrogen atom | Hydrogen atom | — | — | 0 | General formula (2) |
| (11) | Aryl group | Aliphatic ring | | | | Hydrogen atom | Hydrogen atom | — | — | 0 | General formula (2) |
| (12) | Aryl group | Aliphatic ring | | | | Hydrogen atom | Hydrogen atom | — | — | 0 | General formula (2) |
| (13) | Aryl group | Aliphatic ring | | | | Hydrogen atom | Hydrogen atom | — | — | 0 | General formula (2) |
| (14) | Alkyl group | Aliphatic ring | | | | Hydrogen atom | Hydrogen atom | — | — | 0 | General formula (2) |
| (15) | Alkyl group | Aliphatic ring | | | | Hydrogen atom | Hydrogen atom | — | — | 0 | General formula (2) |
| (16) | Aryl group | Aliphatic ring | | | | Hydrogen atom | Hydrogen atom | — | — | 0 | General formula (2) |
| (17) | Aryl group | Aliphatic ring | | | | Hydrogen atom | Hydrogen atom | — | — | 0 | General formula (2) |
| (18) | Alkyl group | Aliphatic ring | | | | Hydrogen atom | Hydrogen atom | — | — | 0 | General formula (2) |
| (19) | Aryl group | Aliphatic ring | | | | Hydrogen atom | Hydrogen atom | — | — | 0 | General formula (2) |
| (20) | Aryl group | Aliphatic ring | | | | Hydrogen atom | Hydrogen atom | — | — | 0 | General formula (2) |
| (21) | Aryl group | Aliphatic ring | | | | Hydrogen atom | Hydrogen atom | — | — | 0 | General formula (2) |
| (22) | Aryl group | Aliphatic ring | | | | Hydrogen atom | Hydrogen atom | — | — | 0 | General formula (2) |
| (23) | Aryl group | Aliphatic ring | | | | Hydrogen atom | Hydrogen atom | — | — | 0 | General formula (2) |
| (24) | Aryl group | Aliphatic ring | | | | Hydrogen atom | Hydrogen atom | — | — | 0 | General formula (2) |
| (25) | Aryl group | Aliphatic ring | | | | Hydrogen atom | Hydrogen atom | — | — | 0 | General formula (2) |
| (26) | Alkyl group | Aliphatic ring | | | | Hydrogen atom | Hydrogen atom | — | — | 0 | General formula (2) |
| (27) | Alkyl group | Aliphatic ring | | | | Hydrogen atom | Hydrogen atom | — | — | 0 | General formula (2) |
| (28) | Aralkyl group | Aliphatic ring | | | | Hydrogen atom | Hydrogen atom | — | — | 0 | General formula (2) |
| (29) | Aryl group | Aliphatic ring | | | | Hydrogen atom | Hydrogen atom | — | — | 0 | General formula (2) |
| (30) | Aryl group | Aliphatic ring | | | | Hydrogen atom | Hydrogen atom | — | — | 0 | General formula (2) |
| (31) | Aryl group | Aliphatic ring | | | | Hydrogen atom | Hydrogen atom | — | — | 0 | General formula (2) |
| (32) | Aryl group | Aliphatic ring | | | | Hydrogen atom | Hydrogen atom | — | — | 0 | General formula (2) |
| (33) | Aryl group | Aliphatic ring | | | | Hydrogen atom | Hydrogen atom | — | — | 0 | General formula (2) |
| (34) | Aryl group | Aliphatic ring | | | | Hydrogen atom | Hydrogen atom | — | — | 0 | General formula (4) |
| (35) | Aryl group | Aliphatic ring | | | | Hydrogen atom | Hydrogen atom | — | — | 0 | General formula (4) |
| (36) | Aryl group | Aliphatic ring | | | | Hydrogen atom | Hydrogen atom | — | — | 0 | General formula (4) |
| (37) | Aryl group | Aliphatic ring | | | | Hydrogen atom | Hydrogen atom | — | — | 0 | General formula (4) |
| (38) | Aryl group | Aliphatic ring | | | | Hydrogen atom | Hydrogen atom | — | — | 0 | General formula (2) |
| (39) | Aryl group | Aliphatic ring | | | | Hydrogen atom | Hydrogen atom | — | — | 0 | General formula (2) |
| (40) | Aryl group | Aliphatic ring | | | | Hydrogen atom | Hydrogen atom | — | — | 0 | General formula (2) |
| (41) | Aryl group | Aliphatic ring | | | | Hydrogen atom | Hydrogen atom | — | — | 0 | General formula (2) |
| (42) | Aralkyl group | Aliphatic ring | | | | Hydrogen atom | Hydrogen atom | — | — | 0 | General formula (2) |

TABLE 1-continued

| Compound | R1 | R2 | R3 | R4 | R5 | R6 | R7 | R8 | Y1 | n | R9 |
|---|---|---|---|---|---|---|---|---|---|---|---|
| (43) | Aralkyl group | | Aliphatic ring | | | Hydrogen atom | Hydrogen atom | — | — | 0 | General formula (2) |
| (44) | Aryl group | | Aliphatic ring | | | Hydrogen atom | Hydrogen atom | — | — | 0 | General formula (2) |
| (45) | Aryl group | | Aliphatic ring | | | Hydrogen atom | Hydrogen atom | — | — | 0 | General formula (2) |
| (46) | Aryl group | | Aliphatic ring | | | Hydrogen atom | Hydrogen atom | — | — | 0 | General formula (2) |
| (47) | Aryl group | | Aliphatic ring | | | Hydrogen atom | Hydrogen atom | — | — | 0 | General formula (2) |
| (48) | Aryl group | | Aliphatic ring | | | Hydrogen atom | Hydrogen atom | — | — | 0 | General formula (2) |
| (49) | Aryl group | | Aliphatic ring | | | Halogen atom | Hydrogen atom | — | — | 0 | General formula (2) |
| (50) | Aryl group | | Aliphatic ring | | | Hydrogen atom | Hydrogen atom | — | — | 0 | General formula (2) |
| (51) | Aryl group | | Aliphatic ring | | | Hydrogen atom | Hydrogen atom | — | — | 0 | General formula (2) |
| (52) | Aralkyl group | | Aliphatic ring | | | Hydrogen atom | Hydrogen atom | — | — | 0 | General formula (2) |
| (53) | Aralkyl group | | Aliphatic ring | | | Hydrogen atom | Hydrogen atom | — | — | 0 | General formula (2) |
| (54) | Aryl group | | Aliphatic ring | | | Hydrogen atom | Hydrogen atom | — | — | 0 | General formula (2) |
| (55) | Aralkyl group | | Aliphatic ring | | | Hydrogen atom | Hydrogen atom | — | — | 0 | General formula (2) |
| (56) | Alkyl group | Alkyl group | | Hydrogen atom | | Hydrogen atom | Hydrogen atom | — | — | 0 | General formula (2) |
| (57) | Alkyl group | Alkyl group | | Hydrogen atom | | Hydrogen atom | Hydrogen atom | — | — | 0 | General formula (2) |
| (58) | Alkyl group | | Aliphatic ring | | | Hydrogen atom | Hydrogen atom | — | — | 0 | General formula (3) |
| (59) | Aryl group | | Aliphatic ring | | | Hydrogen atom | Hydrogen atom | — | — | 0 | General formula (3) |
| (60) | Aryl group | | Aliphatic ring | | | Hydrogen atom | Hydrogen atom | — | — | 0 | General formula (3) |
| (61) | Aryl group | | Aliphatic ring | | | Hydrogen atom | Hydrogen atom | — | — | 0 | General formula (3) |
| (62) | Aryl group | | Aliphatic ring | | | Hydrogen atom | Hydrogen atom | — | — | 0 | General formula (3) |
| (63) | Alkyl group | | Aliphatic ring | | | Hydrogen atom | Hydrogen atom | — | — | 0 | General formula (3) |
| (64) | Alkyl group | | Aliphatic ring | | | Hydrogen atom | Hydrogen atom | — | — | 0 | General formula (3) |
| (65) | Alkyl group | | Aliphatic ring | | | Hydrogen atom | Hydrogen atom | — | — | 0 | General formula (3) |
| (66) | Aryl group | | Aliphatic ring | | | Hydrogen atom | Hydrogen atom | — | — | 0 | General formula (3) |
| (67) | Alkyl group | | Aliphatic ring | | | Hydrogen atom | Hydrogen atom | — | — | 0 | General formula (2) |
| (68) | Alkyl group | | Aliphatic ring | | | Hydrogen atom | Hydrogen atom | — | — | 0 | General formula (2) |
| (69) | Aryl group | | Aliphatic ring | | | Hydrogen atom | Hydrogen atom | — | — | 0 | General formula (2) |
| (70) | Aryl group | | Aliphatic ring | | | Hydrogen atom | Hydrogen atom | — | — | 0 | General formula (2) |
| (71) | Alkyl group | | Aliphatic ring | | | Hydrogen atom | Hydrogen atom | — | — | 0 | General formula (2) |
| (72) | Alkyl group | | Aliphatic ring | | | Hydrogen atom | Hydrogen atom | — | — | 0 | Dicyano-methylene group |
| (73) | Aryl group | | Aliphatic ring | | | Hydrogen atom | Hydrogen atom | — | — | 0 | Cyanocarboxy-methylene group |
| (74) | Aryl group | | Aliphatic ring | | | Hydrogen atom | Hydrogen atom | Hydrogen atom | —CH= | 1 | Cyanocarboxy-methylene group |
| (75) | Aryl group | | Aliphatic ring | | | Hydrogen atom | Hydrogen atom | Hydrogen atom | Cyclohexene ring | 1 | General formula (2) |
| (76) | Alkyl group | | Aliphatic ring | | | Hydrogen atom | Hydrogen atom | Hydrogen atom | —CH= | 1 | General formula (2) |
| (77) | Aryl group | | Aliphatic ring | | | Hydrogen atom | Alkyl group | — | — | 0 | General formula (2) |
| (78) | Alkyl group | | Aliphatic ring | | | Hydrogen atom | Hydrogen atom | Hydrogen atom | Cyclohexene ring | 1 | General formula (2) |
| (79) | Alkyl group | | Aliphatic ring | | | Hydrogen atom | Hydrogen atom | Hydrogen atom | Cyclohexene ring | 1 | General formula (2) |

TABLE 1-continued

| Compound | R1 | R2 | R3 | R4 | R5 | R6 | R7 | R8 | Y1 | n | R9 |
|---|---|---|---|---|---|---|---|---|---|---|---|
| (80) | Aryl group | Aliphatic ring | | | | Hydrogen atom | Hydrogen atom | Hydrogen atom | Cyclohexene ring | 1 | General formula (2) |
| (81) | Aryl group | Aliphatic ring | | | | Hydrogen atom | Hydrogen atom | Hydrogen atom | Cyclohexene ring | 1 | General formula (2) |
| (82) | Aryl group | Aliphatic ring | | | | Hydrogen atom | Hydrogen atom | Hydrogen atom | Cyclohexene ring | 1 | General formula (2) |
| (83) | Aryl group | Aliphatic ring | | | | Hydrogen atom | Hydrogen atom | Hydrogen atom | —CH= | 1 | General formula (2) |
| (84) | Alkyl group | Aliphatic ring | | | | Hydrogen atom | Hydrogen atom | Aryl group | —CH= | 1 | General formula (2) |
| (85) | Aryl group | Aliphatic ring | | | | Hydrogen atom | Hydrogen atom | Hydrogen atom | —CH= | 1 | General formula (2) |

Embodiment 2

A macrophage identification agent according to Embodiment 2 of the present invention contains one or more compounds represented by the following general formula (6):

General formula (6)

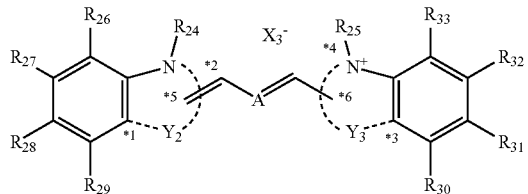

In general formula (6), $R_{24}$ and $R_{25}$ each independently represent an alkyl group, a carboxylalkyl group, an alkoxycarbonylalkyl group, or an alkylcarbonyloxyalkyl group; $R_{26}$ to $R_{33}$ each independently represent a hydrogen atom, an alkyl group, an aryl group, an alkoxy group, a halogen atom, an alkoxysulfonyl group, a N-alkylsulfamoyl group, an alkyloxycarbonyl group, a carbamoyl group, or a N-alkylcarbamoyl group, wherein $R_{26}$ and $R_{27}$, $R_{28}$ and $R_{29}$, $R_{30}$ and $R_{31}$, and $R_{32}$ and $R_{33}$ may be independently cyclized to form a benzene ring; $X_1^-$ represents an anionic group; $Y_2$ represents a group containing *1, *2 and *5, and containing an oxygen atom, a sulfur atom, a N-alkyl nitrogen atom or —C($R_{34}$)($R_{35}$)—, or a group containing *1, *2 and *5 and represented by *1-C*5-CH=CH-*2 or *1-CH=CH-*5-*2; $Y_3$ represents a group containing *3, *4 and *6 and containing an oxygen atom, a sulfur atom, a N-alkyl nitrogen atom or —C($R_{34}$)($R_{35}$)—, or a group containing *3, *4 and *6 and represented by *3-$Y_3$-*6-*4, *3-C*6-CH=CH-*4, or *3-CH=CH-*6-*4, wherein $R_{34}$ and $R_{35}$ each independently represent an alkyl group and may be bound to each other to form a ring; and A represents a 3-oxocyclobutenolate ring or the following general formula (7) or (8):

General formula (7)

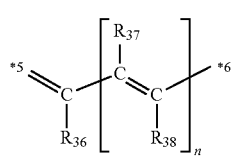

General formula (8)

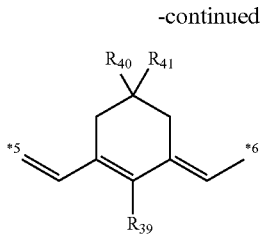

In general formula (7), $R_{36}$ to $R_{38}$ each independently represent a hydrogen atom, an alkyl group or an aryl group; and n represents a value of 0 to 2. In general formula (8), $R_{39}$ represents a hydrogen atom, a phenyl group, a thiol group, an alkoxy group, an aryloxy group, or a halogen atom; and $R_{40}$ and $R_{41}$ each independently represent a hydrogen atom, an alkyl group or an alkyloxycarbonyl group.

<Regarding Compounds>

The compounds represented by general formula (6) of the present embodiment will now be described.

In general formula (6), the alkyl group used as $R_{24}$ and $R_{25}$ is not especially limited, and examples include a methyl group, an ethyl group, a propyl group, a butyl group, a pentyl group and a hexyl group.

In general formula (6), the carboxylalkyl group used as $R_{24}$ and $R_{25}$ is not especially limited, and examples include a carboxylmethyl group, a carboxylethyl group, and a carboxylpropyl group.

In general formula (6), the alkoxycarbonylalkyl group used as $R_{24}$ and $R_{25}$ is not especially limited, and examples include a methoxycarbonylmethyl group, a methoxycarbonylethyl group, an ethoxycarbonylethyl group, a butoxycarbonylethyl group, and a methoxycarbonylpropyl group. The alkylcarbonyloxyalkyl group used as $R_{24}$ and $R_{25}$ is not especially limited, and examples include a methylcarbonyloxymethyl group, an ethylcarbonyloxymethyl group, an ethylcarbonyloxyethyl group, ethylcarbonylbutyl, and a proxycarbonyloxymethyl group.

In general formula (6), the alkyl group used as $R_{26}$ to $R_{33}$ is not especially limited, and examples include a methyl group, an ethyl group, a propyl group, a butyl group, a pentyl group and a hexyl group.

In general formula (6), the aryl group used as $R_{26}$ to $R_{33}$ is not especially limited, and examples include a phenyl group, a 2-bromophenyl group, a 3-bromophenyl group, a 4-bromophenyl group, a 2-methoxyphenyl group, a 3-methoxyphenyl group, a 4-methoxyphenyl group, a 2-thiomethylphenyl group, a 3-thiomethylphenyl group, a 4-thiomethylphenyl group and a naphthyl group.

In general formula (6), the alkoxy group used as $R_{26}$ to $R_{33}$ is not especially limited, and examples include a methoxy group, an ethoxy group a propoxy group and a butoxy group.

In general formula (6), examples of the halogen atom used as $R_{26}$ to $R_{33}$ include a fluorine atom, a chlorine atom, a bromine atom and an iodine atom.

In general formula (6), the alkoxysulfonyl group used as $R_{26}$ to $R_{33}$ is not especially limited, and examples include a methoxysulfonyl group and an ethoxysulfonyl group.

In general formula (6), N-alkylsulfamoyl used as $R_{26}$ to $R_{33}$ is not especially limited, and examples include a N-methylsulfamoyl group, a N-ethylsulfamoyl group, a N,N-dimethylsulfamoyl group and a N,N-ethylsulfamoyl group.

In general formula (6), the alkyloxycarbonyl group used as $R_{26}$ to $R_{33}$ is not especially limited, and examples include a methyloxycarbonyl group, an ethyloxycarbonyl group, a propyloxycarbonyl group and a butyloxycarbonyl group.

In general formula (6), the N-alkylcarbamoyl group used as $R_{26}$ to $R_{33}$ is not especially limited, and examples include a N-methylcarbamoyl group, a N-ethylcarbamoyl group, a N,N-dimethylcarbamoyl group and a N,N-diethylcarbamoyl group.

In general formula (6), $R_{26}$ to $R_{33}$ each independently represent preferably a hydrogen atom, a halogen atom, a phenyl group or an alkoxy group, and more preferably a hydrogen atom or a phenyl group.

In general formula (6), the anionic group represented by $X_3^-$ is not especially limited, and examples include a chloride ion, a bromide ion, an iodide ion, a sulfate ion, a nitrate ion, a methanesulfonate ion, a p-toluenesulfonate ion, a tetrafluoroborate ion, a hexafluorophosphate ion, and an ammonium ion.

In general formula (6), the alkylene group used as $Y_2$ and $Y_3$ is not especially limited, and examples include a methylene group, an ethylene group, a propylene group and a butylene group.

In general formula (6), the alkyl group used as $R_{34}$ and $R_{35}$ of $Y_2$ and $Y_3$ is not especially limited, and examples include a methyl group, an ethyl group, a propyl group, a butyl group, a pentyl group, a hexyl group, and a 2-ethylhexyl group. $R_{34}$ and $R_{35}$ are preferably the same but may be different from each other.

In general formula (6), $R_{34}$ and $R_{35}$ may be bound to each other to form an aliphatic ring, and examples of the ring include a cyclohexane ring and a cyclopentane ring.

In general formula (7), the alkyl group used as $R_{36}$ to $R_{38}$ is not especially limited, and examples include a methyl group, an ethyl group, a propyl group, a butyl group, a pentyl group and a hexyl group.

In general formula (7), the aryl group used as $R_{36}$ to $R_{38}$ is not especially limited, and examples include a phenyl group, a 2-bromophenyl group, a 3-bromophenyl group, a 4-bromophenyl group, a 2-methoxyphenyl group, a 3-methoxyphenyl group, a 4-methoxyphenyl group, a 2-thiomethylphenyl group, a 3-thiomethylphenyl group, and a 4-thiomethylphenyl group.

In general formula (8), examples of the thiol group used as $R_{39}$ include a mercaptomethyl group, a mercaptobutyl group and a mercaptophenyl group.

In general formula (8), examples of the alkoxy group used as $R_{39}$ include a methoxy group, an ethoxy group, a propoxy group and a butoxy group.

In general formula (8), examples of the aryloxy group used as $R_{39}$ include a phenoxy group and a phenoxy group that may have a substituent.

In general formula (8), examples of the halogen atom used as $R_{39}$ include a fluorine atom, a chlorine atom, a bromine atom and an iodine atom.

In general formula (8), the alkyl group used as $R_{40}$ and $R_{41}$ is not especially limited, and examples include alkyl groups, such as a methyl group, an ethyl group, a propyl group, a butyl group, a pentyl group and a hexyl group.

In general formula (8), the alkyloxycarbonyl group used as $R_{40}$ and $R_{41}$ is not especially limited, and examples include a methyloxycarbonyl group, an ethyloxycarbonyl group, a propyloxycarbonyl group and a butyloxycarbonyl group.

<Regarding Compounds Represented by General Formula (9)>

Suitable examples of the compound of the present embodiment include compounds represented by the following general formula (9):

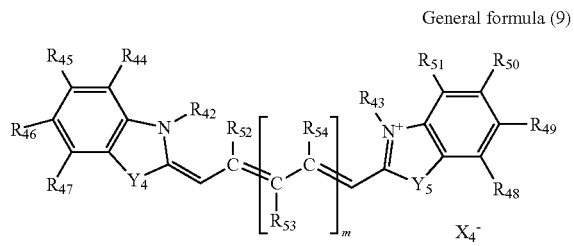

General formula (9)

In general formula (9), $R_{42}$ and $R_{43}$ each independently represent an alkyl group, a carboxylalkyl group, an alkylcarbonyloxyalkyl group, or an alkoxycarbonyl alkyl group; $R_{44}$ to $R_{51}$ each independently represent a hydrogen atom, an alkyl group, an aryl group, an alkoxy group, a halogen atom, an alkoxysulfonyl group, a N-alkylsulfamoyl group, an alkyloxycarbonyl group, or a N-alkylcarbamoyl group, wherein $R_{44}$ and $R_{45}$, $R_{46}$ and $R_{47}$, $R_{48}$ and $R_{49}$, and $R_{50}$ and $R_{51}$ may be independently cyclized to form a benzene ring; $R_{52}$ to $R_{54}$ each independently represent a hydrogen atom, an alkyl group or an aryl group; m represents a value of 0 to 2; $X_2^-$ represents an anionic group; $Y_4$ and $Y_5$ each represent an oxygen atom, a sulfur atom or an alkylene group, wherein the alkylene group may have a substituent, the substituent used in this case is an alkyl group, and the substituents may be bound to each other to form an aliphatic ring.

In general formula (9), the alkyl group used as $R_{42}$ and $R_{43}$ is not especially limited, and examples include alkyl groups such as a methyl group, an ethyl group, a propyl group, a butyl group, a pentyl group, and a hexyl group.

In general formula (9), the carboxylalkyl group used as $R_{42}$ and $R_{43}$ is not especially limited, and examples include a carboxylmethyl group, a carboxylethyl group and a carboxylpropyl group.

In general formula (9), the alkoxycarbonylalkyl group used as $R_{42}$ and $R_{43}$ is not especially limited, and examples include a methoxycarbonylmethyl group, a methoxycarbonylethyl group, an ethoxycarbonylethyl group, a butoxycarbonylethyl group, and a methoxycarbonylpropyl group.

In general formula (9), the alkylcarbonyloxyalkyl group is not especially limited, and examples include a methylcarbonyloxymethyl group, an ethylcarbonyloxymethyl group, an ethylcarbonyloxyethyl group, ethylcarbonylbutyl, and a proxycarbonyloxymethyl group.

In general formula (9), the alkyl group used as $R_{44}$ to $R_{48}$ is not especially limited, and examples include a methyl group, an ethyl group, a propyl group, a butyl group, a pentyl group and a hexyl group.

In general formula (9), the aryl group used as $R_{44}$ to $R_{48}$ is not especially limited, and examples include a phenyl group, a 2-bromophenyl group, a 3-bromophenyl group, a 4-bromophenyl group, a 2-methoxyphenyl group, a 3-methoxyphenyl group, a 4-methoxyphenyl group, a 2-thiomethylphenyl group, a 3-thiomethylphenyl group, a 4-thiomethylphenyl group and a naphthyl group.

In general formula (9), the alkoxy group used as $R_{44}$ to $R_{48}$ is not especially limited, and examples include a methoxy group, an ethoxy group, a propoxy group and a butoxy group.

In general formula (9), examples of the halogen atom used as $R_{44}$ to $R_{51}$ include a fluorine atom, a chlorine atom, a bromine atom and an iodine atom.

In general formula (9), the alkoxysulfonyl group used as $R_{44}$ to $R_{51}$ is not especially limited, and examples include a methoxysulfonyl group and an ethoxysulfonyl group.

In general formula (9), the N-alkylsulfamoyl group used as $R_{44}$ to $R_{51}$ is not especially limited, and examples include a N-methylsulfamoyl group, a N-ethylsulfamoyl group, a N,N-dimethylsulfamoyl group and a N,N-ethylsulfamoyl group.

In general formula (9), the alkyloxycarbonyl group used as $R_{44}$ to $R_{51}$ is not especially limited, and examples include a methyloxycarbonyl group, an ethyloxycarbonyl group, a propyloxycarbonyl group and a butyloxycarbonyl group.

In general formula (9), the N-alkylcarbamoyl group used as $R_{44}$ to $R_{51}$ is not especially limited, and examples include a N-methylcarbamoyl group, a N-ethylcarbamoyl group, a N,N-dimethylcarbamoyl group and a N,N-diethylcarbamoyl group.

In general formula (9), $R_{44}$ to $R_{51}$ each independently represent preferably a hydrogen atom, a halogen atom, a phenyl group or an alkoxy group, and more preferably a hydrogen atom or a phenyl group.

In general formula (9), the alkyl group used as $R_{52}$ to $R_{51}$ is not especially limited, and examples include a methyl group, an ethyl group, a propyl group, a butyl group, a pentyl group and a hexyl group.

In general formula (9), the aryl group used as $R_{52}$ to $R_{51}$ is not especially limited, and examples include a phenyl group, a 2-bromophenyl group, a 3-bromophenyl group, a 4-bromophenyl group, a 2-methoxyphenyl group, a 3-methoxyphenyl group, a 4-methoxyphenyl group, a 2-thiomethylphenyl group, a 3-thiomethylphenyl group, and a 4-thiomethylphenyl group.

In general formula (9), the anionic group represented by $X_4^-$ is not especially limited, and examples include a chloride ion, a bromide ion, an iodide ion, a sulfate ion, a nitrate ion, a methanesulfonate ion, a p-toluenesulfonate ion, a tetrafluoroborate ion, a hexafluorophosphate ion, and an ammonium ion.

In general formula (9), $Y_4$ and $Y_5$ each represent an oxygen atom, a sulfur atom or an alkylene group, the alkylene group may have a substituent, the substituent used in this case is an alkyl group, and the substituents may be bound to each other to form an aliphatic ring.

Here, the alkylene group is not especially limited, and examples include a methylene group, an ethylene group, a propylene group, a butylene group, a pentylene group, a hexylene group, and a 2-ethylhexylene group. The aliphatic ring formed by the substituents is not especially limited, and examples include a cyclohexane ring and a cyclopentane ring.

Many of the compounds represented by general formula (9) of the present embodiment are put on the market and can be available. Alternatively, these compounds can be synthesized by a method similar to known methods (NPL 2 and the like).

<Compounds Represented by General Formula (12)>

Suitable examples of the compound of the present embodiment include compounds represented by the following general formula (12):

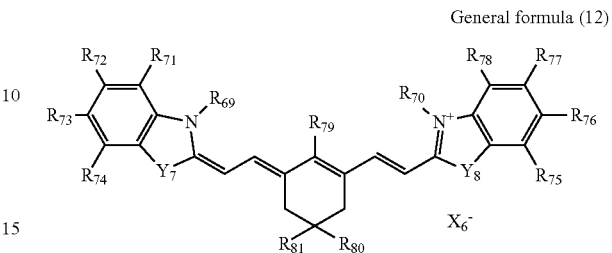

General formula (12)

In general formula (12), $R_{69}$ and $R_{70}$ each independently represent an alkyl group, a carboxylalkyl group, or an alkoxycarbonylalkyl group; and $R_{71}$ to $R_{78}$ each independently represent a hydrogen atom, an alkyl group, an aryl group, an alkoxy group, a halogen atom, an alkoxysulfonyl group, a N-alkylsulfamoyl group, an alkyloxycarbonyl group, or a N-alkylcarbamoyl group, wherein $R_{71}$ and $R_{72}$, $R_{73}$ and $R_{74}$, $R_{75}$ and $R_{76}$, and $R_{77}$ and $R_{78}$ may be independently cyclized to form a benzene ring.

$R_{79}$ represents a hydrogen atom, a phenyl group, a thiol group, an alkoxy group, an aryloxy group, or a halogen atom; $R_{80}$ and $R_{81}$ each independently represent a hydrogen atom, an alkyl group or an alkylcarbonyloxy group; $X_6^-$ represents an anionic group; $Y_7$ and $Y_8$ each represent an oxygen atom, a sulfur atom or an alkylene group, wherein the alkylene group may have a substituent, the substituent used in this case is an alkyl group, and the substituents may be bound to each other to form an aliphatic ring.

In general formula (12), the alkyl group used as $R_{69}$ and $R_{70}$ is not especially limited, and examples include alkyl groups such as a methyl group, an ethyl group, a propyl group, a butyl group, a pentyl group, and a hexyl group.

In general formula (12), the carboxylalkyl group used as $R_{69}$ and $R_{70}$ is not especially limited, and examples include an acetic acid group, a propionic acid group and a butanoic acid group.

In general formula (12), the alkoxycarbonylalkyl group used as $R_{69}$ and $R_{70}$ is not especially limited, and examples include a methoxycarbonylmethyl group, a methoxycarbonylethyl group, an ethoxycarbonylethyl group, a butoxycarbonylethyl group, and a methoxycarbonylpropyl group.

In general formula (12), the alkyl group used as $R_{71}$ to $R_{78}$ is not especially limited, and examples include a methyl group, an ethyl group, a propyl group, a butyl group, a pentyl group, and a hexyl group.

In general formula (12), the aryl group used as $R_{71}$ to $R_{78}$ is not especially limited, and examples include a phenyl group, a 2-bromophenyl group, a 3-bromophenyl group, a 4-bromophenyl group, a 2-methoxyphenyl group, a 3-methoxyphenyl group, a 4-methoxyphenyl group, a 2-thiomethylphenyl group, a 3-thiomethylphenyl group, a 4-thiomethylphenyl group, and a naphthyl group.

In general formula (12), the alkoxy group used as $R_{71}$ to $R_{78}$ is not especially limited, and examples include a methoxy group, an ethoxy group, a propoxy group and a butoxy group.

In general formula (12), examples of the halogen atom used as $R_{71}$ to $R_{78}$ include a fluorine atom, a chlorine atom, a bromine atom and an iodine atom.

In general formula (12), the alkoxysulfonyl group used as $R_{71}$ to $R_{78}$ is not especially limited, and examples include a methyl sulfonate group and an ethyl sulfonate group.

In general formula (12), the alkylsulfamoyl group used as $R_{71}$ to $R_{78}$ is not especially limited, and examples include a sulfonic acid monomethyl amide group, a monoethyl amide sulfonate group, a dimethyl amide sulfonate group, and a diethyl amide sulfonate group.

In general formula (12), the alkylcarbonyloxyalkyl group used as $R_{71}$ to $R_{78}$ is not especially limited, and examples include a carboxylic acid methyl ester group, a carboxylic acid ethyl ester group, a carboxylic acid propyl ester group, and a carboxylic acid butyl ester group.

In general formula (12), the N-alkylcarbamoyl group used as $R_{71}$ to $R_{78}$ is not especially limited, and examples include a N-methylcarbamoyl group, a N-ethylcarbamoyl group, a N,N-dimethylcarbamoyl group and a N,N-diethylcarbamoyl group.

In general formula (12), $R_{71}$ to $R_{78}$ represent preferably a hydrogen atom, a halogen atom, a phenyl group or an alkoxy group, and more preferably a hydrogen atom or a phenyl group.

In general formula (12), examples of the thiol group used as $R_{79}$ include a mercaptomethyl group, a mercaptobutyl group and a mercaptophenyl group.

In general formula (12), examples of the alkoxy group used as $R_{79}$ include a methoxy group, an ethoxy group, a propoxy group and a butoxy group.

In general formula (12), examples of the aryloxy group used as $R_{79}$ include a phenoxy group, or a phenoxy group that may have a substituent.

In general formula (12), examples of the halogen atom used as $R_{79}$ include a fluorine atom, a chlorine atom, a bromine atom and an iodine atom.

In general formula (12), the alkyl group used as $R_{80}$ and $R_{81}$ is not especially limited, and examples include alkyl groups such as a methyl group, an ethyl group, a propyl group, a butyl group, a pentyl group, and a hexyl group.

In general formula (12), the alkyloxycarbonyl group used as $R_{80}$ and $R_{81}$ is not especially limited, and examples include a methyloxycarbonyl group, an ethyloxycarbonyl group, a propyloxycarbonyl group and a butyloxycarbonyl group.

In general formula (12), the anionic group represented by $X_6^-$ is not especially limited, and examples include a chloride ion, a bromide ion, an iodide ion, a sulfate ion, a nitrate ion, a methanesulfonate ion, a p-toluenesulfonate ion, a tetrafluoroborate ion, a hexafluorophosphate ion, and an ammonium ion.

In general formula (12), the alkylene group used as $Y_7$ and $Y_8$ is not especially limited, and examples include a methylene group, an ethylene group, a propylene group, a butylene group, a pentylene group, a hexylene group, and a 2-ethylene hexyl group. The alkyl group used as a substituent of the alkylene group is not especially limited, and examples include a methyl group, an ethyl group, a propyl group and a butyl group.

Many of the compounds represented by general formula (12) of the present invention are put on the market and can be easily available. Alternatively, these compounds can be easily synthesized by a method similar to known methods (for example, NPL 8).

Suitable specific examples of the compounds of the present embodiment include, but are not limited to, the following compounds (86) to (115):

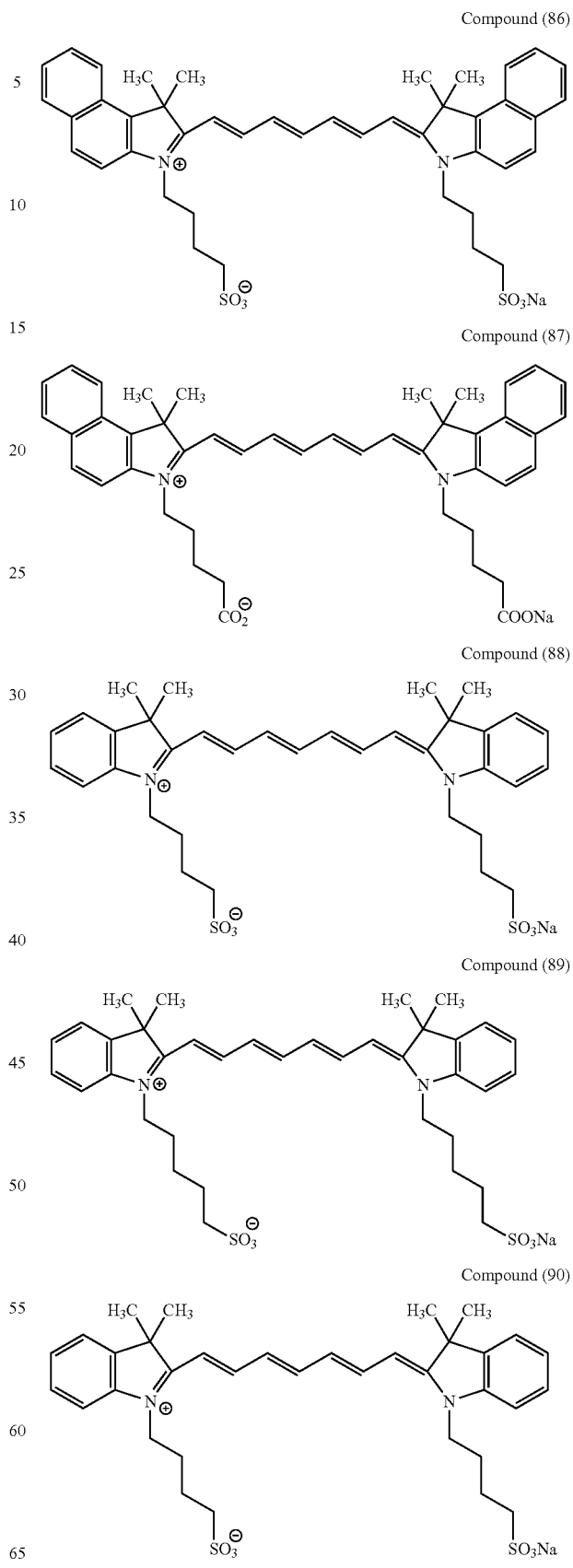

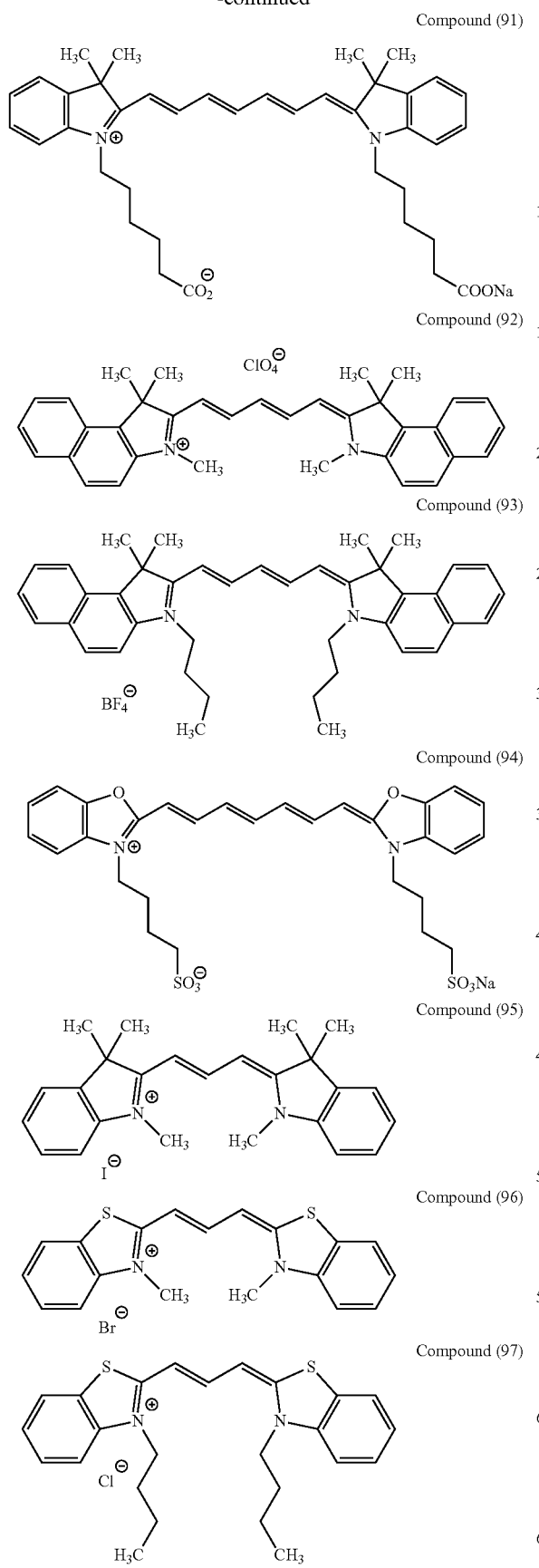
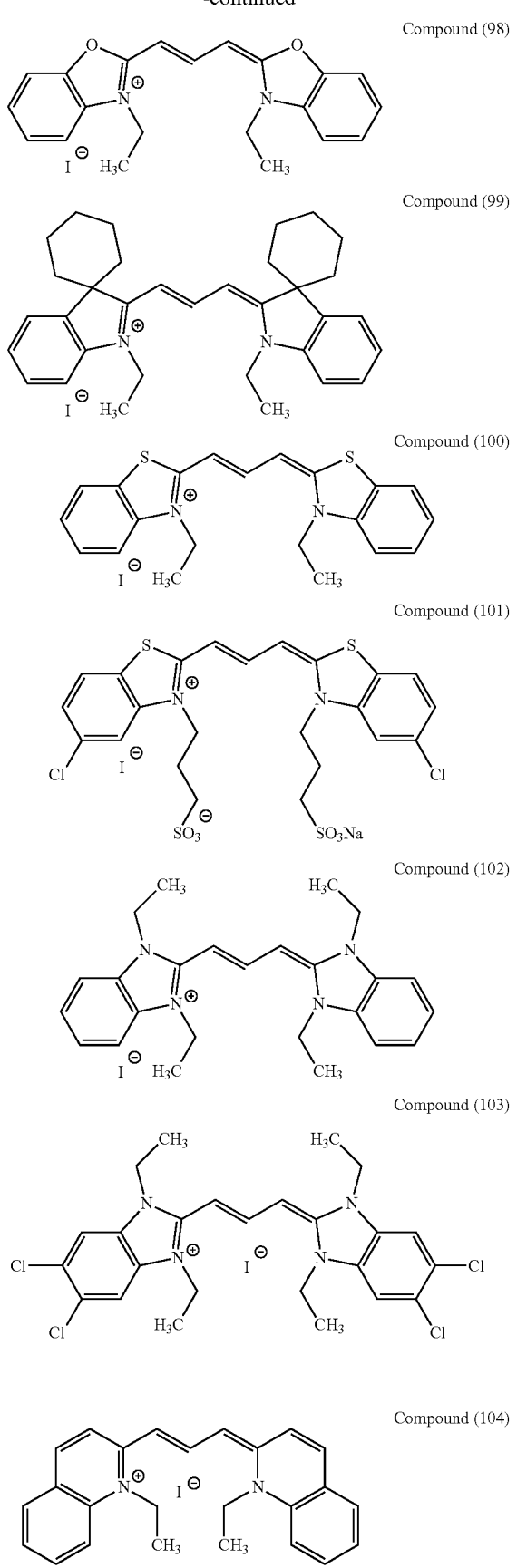

Compound (105)
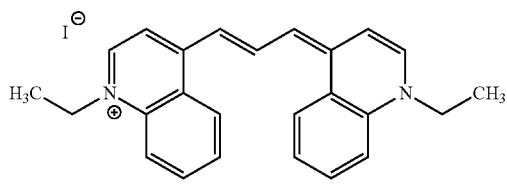
Compound (106)
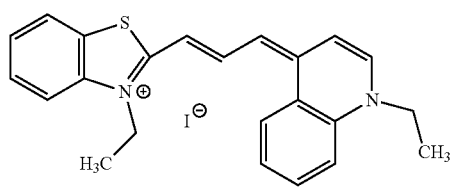
Compound (107)
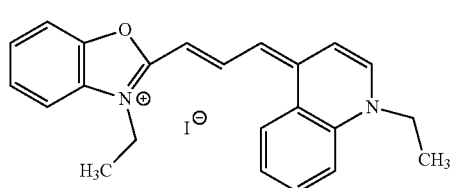
Compound (108)
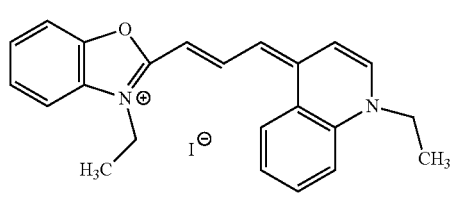
Compound (109)
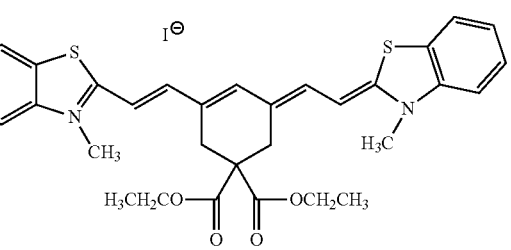
Compound (110)
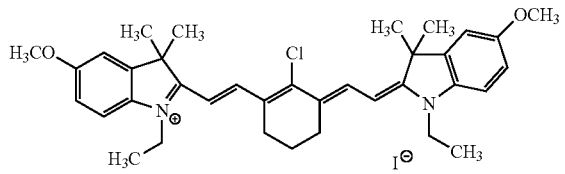
Compound (111)
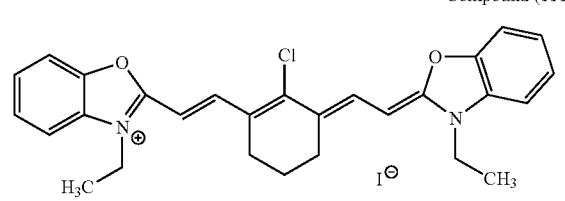
Compound (112)
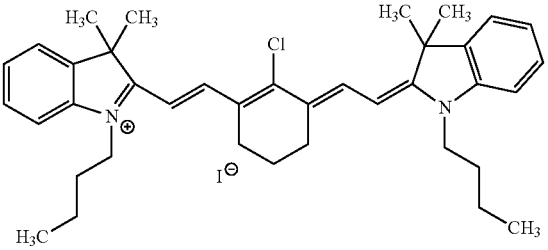
Compound (113)
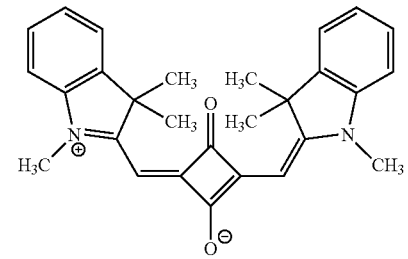
Compound (114)
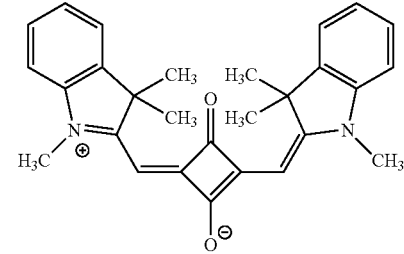
Compound (115)
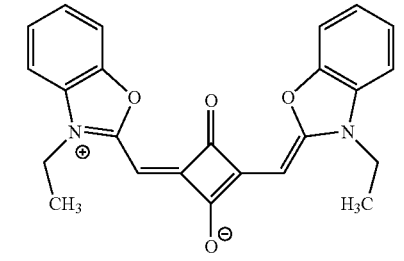
Embodiment 3
A macrophage identification agent according to Embodiment 3 of the present invention contains one or more compounds represented by the following general formula (10):
General formula (10)
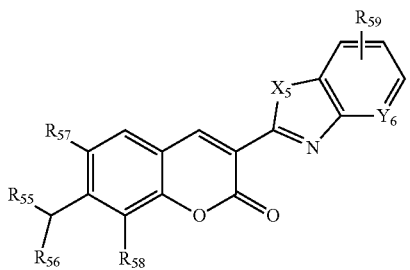

In general formula (10), $R_{55}$ and $R_{56}$ each independently represent an alkyl group; $R_{57}$ and $R_{58}$ each independently represent a hydrogen atom or an alkyl group, wherein $R_{55}$ and $R_{57}$, and $R_{56}$ and $R_{58}$ may be independently bound to each other to form a ring; $R_{59}$ represents a hydrogen atom, an alkyl group, an aryl group, an alkoxy group or a halogen atom; $X_5$ represents a sulfur atom, an oxygen atom or —$NR_6$—; and $Y_6$ represents a carbon atom or a nitrogen atom.

<Regarding Compounds>

The compounds represented by general formula (10) will be described. In general formula (10), the alkyl group used as $R_{55}$ and $R_{56}$ is not especially limited, and examples include linear or branched alkyl groups having 1 to 12 carbon atoms, such as a methyl group, an ethyl group, a propyl group, a butyl group and an ethylhexyl group. $R_{55}$ and $R_{56}$ can be a methyl group or an ethyl group.

In general formula (10), the alkyl group used as $R_{57}$ and $R_{58}$ is not especially limited, and examples include linear or branched alkyl groups having 1 to 12 carbon atoms, such as a methyl group, an ethyl group, a propyl group, a butyl group and an ethylhexyl group.

In general formula (10), the ring formed when $R_{55}$ and $R_{57}$ or $R_{56}$ and $R_{58}$ are bound to each other is not especially limited, and examples include a tetrahydropyridine ring or a piperidine ring.

In general formula (10), the alkyl group used as $R_{59}$ is not especially limited, and examples include linear or branched alkyl groups having 1 to 12 carbon atoms, such as a methyl group, an ethyl group, a propyl group, a butyl group and an ethylhexyl group.

In general formula (10), the aryl group used as $R_{59}$ is not especially limited, and examples include a phenyl group, a methylphenyl group, a bromophenyl group and a methoxyphenyl group.

In general formula (10), the alkoxy group used as $R_{59}$ is not especially limited, and examples include a methoxy group, an ethoxy group, a propoxy group and a butoxy group.

In general formula (10), the halogen atom used as $R_{59}$ is not especially limited, and examples include a fluorine atom, a chloro atom, a bromo atom and an iodine atom.

In general formula (10), $X_5$ can be a sulfur atom or an oxygen atom because a subtype can be more easily identified in such a case.

The compounds represented by general formula (10) of the present embodiment can be easily synthesized by a method similar to known methods (NPL 3 and the like).

Suitable specific examples of the compounds represented by general formula (10) of the present embodiment include, but are not limited to, the following compounds (116) to (138):

Compound (116)

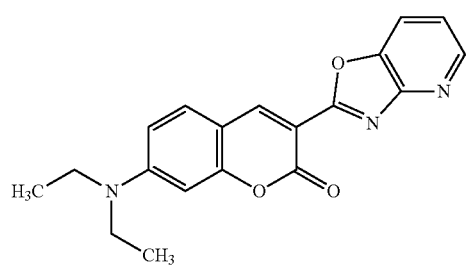

-continued

Compound (117)

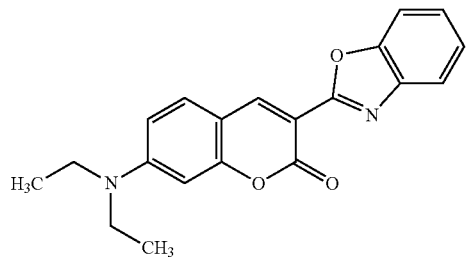

Compound (118)

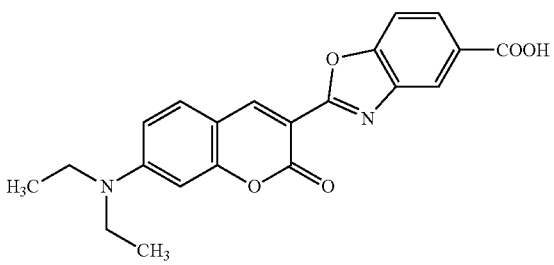

Compound (119)

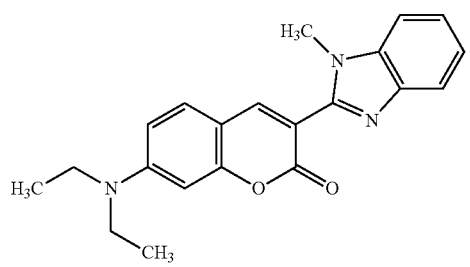

Compound (120)

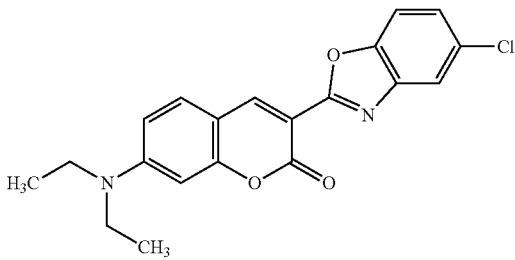

Compound (121)

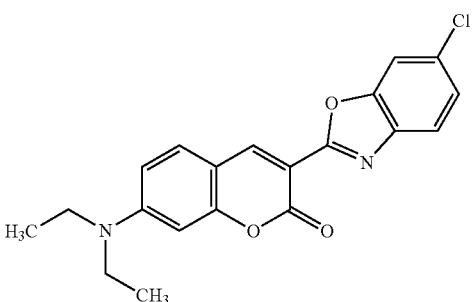

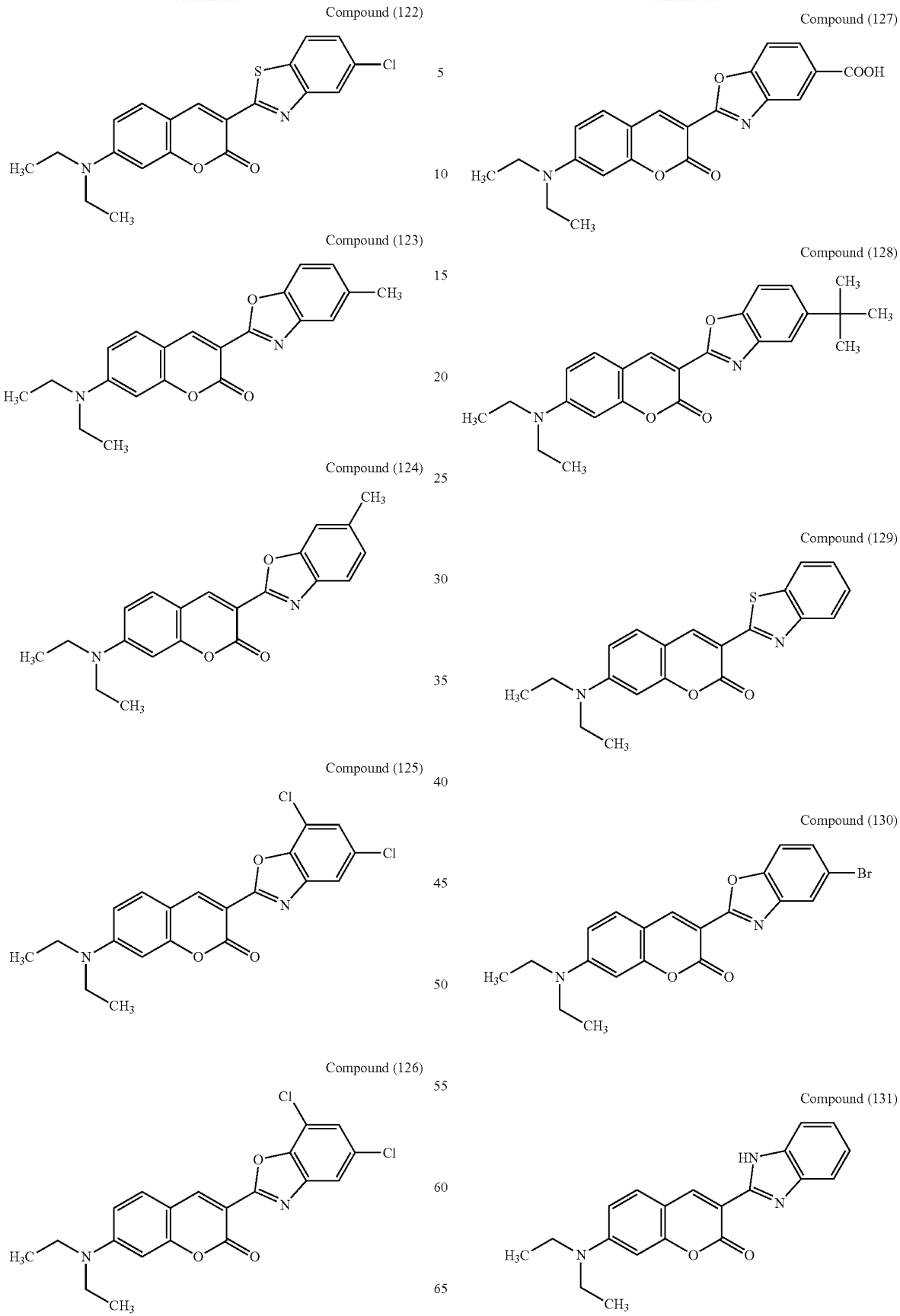

-continued

Compound (132)
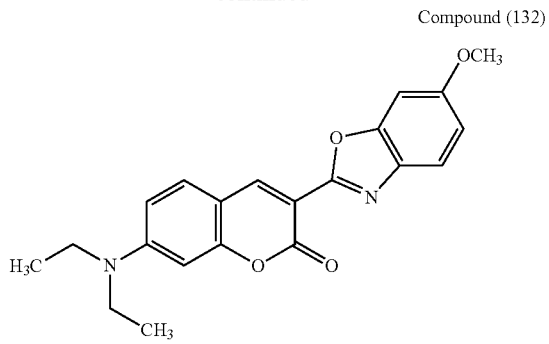

Compound (133)
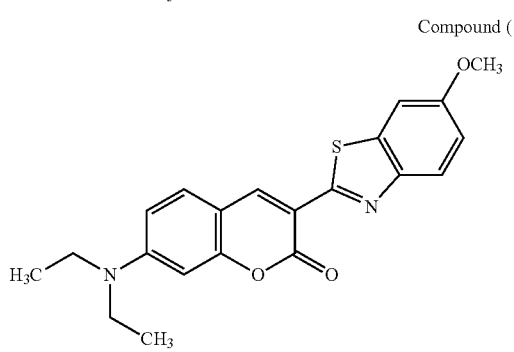

Compound (134)
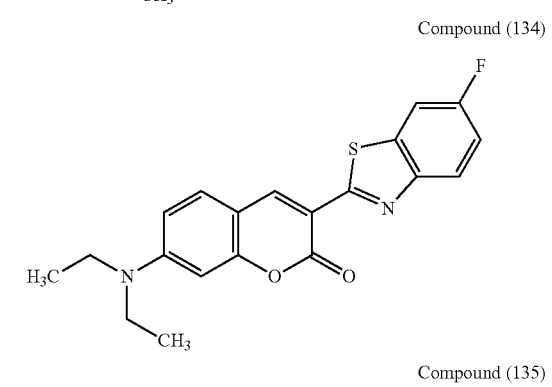

Compound (135)
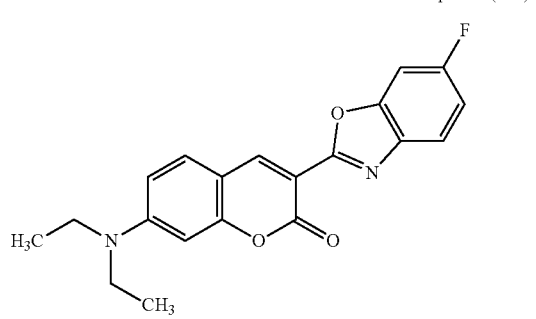

Compound (136)
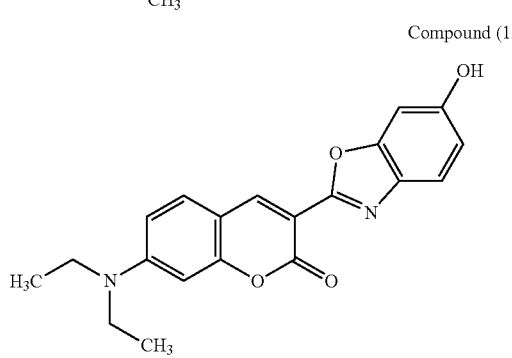

-continued

Compound (137)
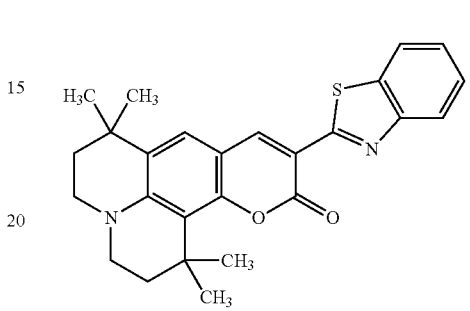

Compound (138)
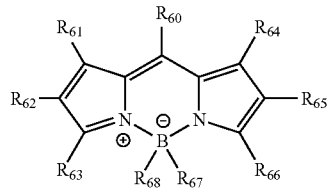

Embodiment 4

A macrophage identification agent according to Embodiment 4 of the present invention contains one or more compounds represented by the following general formula (11):

General formula (11)

In general formula (11), $R_{60}$ represents a hydrogen atom, an alkyl group, an aryl group, a thioalkyl group, an amino group, a hetero ring group, an alkenyl group, a hydroxyl group, a halogen atom, or an alkoxy group; $R_{61}$ to $R_{66}$ each independently represent a hydrogen atom, an alkyl group, an aryl group, a hetero ring group, an aralkyl group, or a sulfonyl group, wherein $R_{62}$ and $R_{63}$, and $R_{65}$ and $R_{66}$ may be bound to each other to form a hetero ring; and $R_{67}$ and $R_{68}$ each independently represent a fluorine atom or an alkynyl group.

<Regarding Compounds>

The compounds represented by general formula (11) will be described. In general formula (11), the alkyl group used as $R_{60}$ is not especially limited, and examples include linear or branched alkyl groups having 1 to 12 carbon atoms, such as a methyl group, an ethyl group, a propyl group, a butyl group and an ethylhexyl group, and alkyl halide groups such as trifluoromethyl.

In general formula (11), the aryl group used as $R_{60}$ is not especially limited, and examples include a phenyl group, a methylphenyl group, a methoxyphenyl group, a thiomethylphenyl group, a chlorophenyl group, a bromophenyl group, a fluorophenyl group, a butylphenyl group, a dimethylphenyl group, a trimethylphenyl group and a naphthyl group.

In general formula (11), the thioalkyl group used as $R_{60}$ is not especially limited, and examples include linear or branched thioalkyl groups having 1 to 12 carbon atoms, such as a thiomethyl group, a thioethyl group, a thiopropyl group, a thiobutyl group, and a thioethylylhexyl group.

In general formula (11), the amino group used as $R_{60}$ is not especially limited, and examples include an amino group, a methylamino group, a dimethylamino group, a butylamino group, a dibutylamino group and a phenylamino group.

In general formula (11), the hetero ring group used as $R_{60}$ is not especially limited, and examples include a pyridine ring, a thiophene ring, and a furan ring.

In general formula (11), the alkenyl group used as $R_{60}$ is not especially limited, and examples include a vinyl group and a 3-butenyl group.

In general formula (11), the halogen atom used as $R_{60}$ is not especially limited, and examples include a fluorine atom, a chloro atom, a bromo atom and an iodine atom.

In general formula (11), the alkoxy group used as $R_{60}$ is not especially limited, and examples include a methoxy group, an ethoxy group, a propoxy group and a butoxy group.

In general formula (11), $R_{60}$ represents preferably an alkyl group or an aryl group, and particularly preferably a methyl group, an ethyl group, a propyl group, a butyl group or a phenyl group because a subtype can be more easily identified in such a case.

In general formula (11), the alkyl group used as $R_{61}$ to $R_{66}$ is not especially limited, and examples include linear or branched alkyl groups having 1 to 12 carbon atoms, such as a methyl group, an ethyl group, a propyl group, a butyl group and an ethylhexyl group.

In general formula (11), the aryl group used as $R_{61}$ to $R_{66}$ is not especially limited, and examples include a phenyl group, a methylphenyl group, a methoxyphenyl group, a thiomethylphenyl group, a chlorophenyl group, a bromophenyl group, a fluorophenyl group, a butylphenyl group, a dimethylphenyl group, a trimethylphenyl group and a naphthyl group.

In general formula (11), the hetero ring group used as $R_{61}$ to $R_{66}$ is not especially limited, and examples include a pyridine ring, a thiophene ring, and a furan ring.

In general formula (11), the aralkyl group used as $R_{61}$ to $R_{66}$ is not especially limited, and examples include a benzyl group or a phenethyl group.

In general formula (11), the sulfonyl group used as $R_{61}$ to $R_{66}$ is not especially limited, and examples include a sulfo group and a salt such as sodium sulfonate.

In general formula (11), the hetero ring formed when $R_{62}$ and $R_{63}$ or $R_{65}$ and $R_{66}$ are bound to each other is not especially limited, and an example includes a furan ring.

In general formula (11), $R_{60}$ to $R_{66}$ each may further have a substituent, and the substituent is not especially limited as long as the identification of a subtype is not largely inhibited. Examples include alkyl groups such as a methyl group, an ethyl group, a n-propyl group, an isopropyl group, a n-butyl group, an isobutyl group, a sec-butyl group and a tert-butyl group; aryl groups such as a phenyl group and a naphthyl group; alkoxy groups such as a methoxy group, an ethoxy group, and a butoxy group; aryloxy groups such as a phenoxy group and a naphthyloxy group; di-substituted amino groups such as a dimethylamino group, a N-ethyl-N-phenylamino group and a diphenylamino group; acyl groups such as an acetyl group and a benzoyl group; a sulfonyl group; a carbamoyl group; a sulfamoyl group; hetero ring groups such as a pyridyl group, a triazinyl group, and a benzothiazolyl group; a nitro group; and halogen atoms such as a fluorine atom, a chlorine atom, a bromine atom and an iodine atom.

In general formula (11), the alkynyl group used as $R_{67}$ and $R_{67}$ is not especially limited, and examples include a vinyl group and a 3-butenyl group.

The compounds represented by general formula (11) of the present embodiment can be easily synthesized by a method similar to known methods (for example, NPL 4, NPL 5 and NPL 6).

Suitable specific examples of the compounds represented by general formula (11) of the present invention include, but are not limited to, the following compounds (139) to (169). In the following, TMS stands for a trimethyl silyl group $(-Si(CH_3)_3)$.

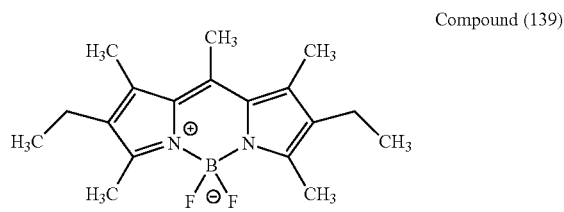

Compound (139)

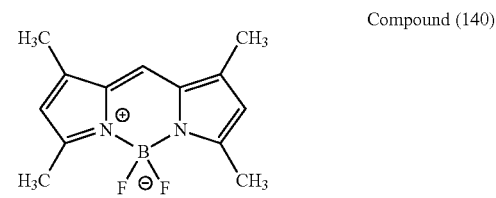

Compound (140)

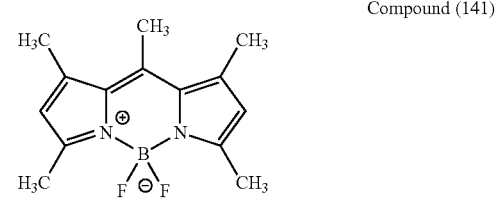

Compound (141)

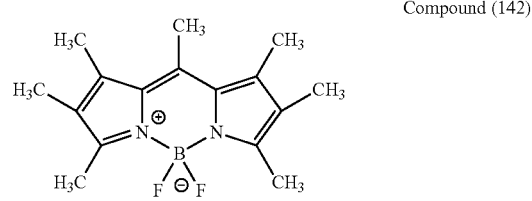

Compound (142)

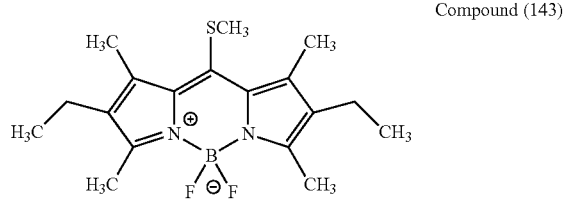

Compound (143)

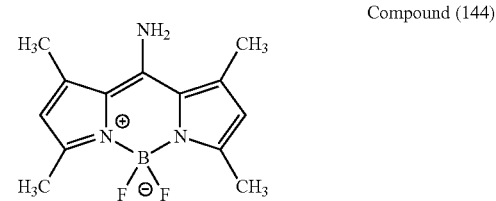

Compound (144)

Compound (145)
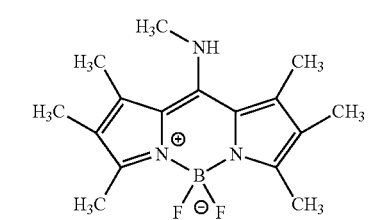
Compound (146)
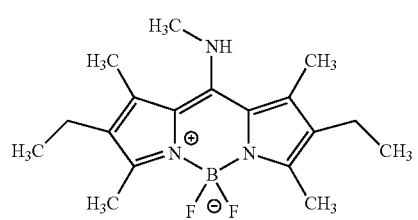
Compound (147)
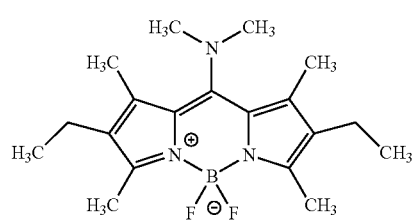
Compound (148)
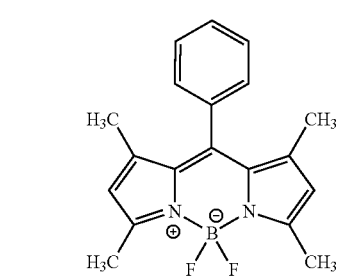
Compound (149)
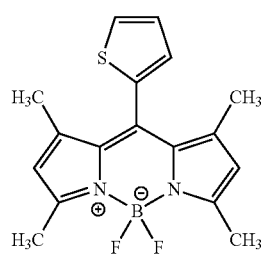
Compound (150)
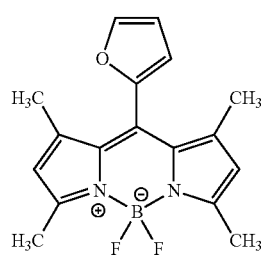
Compound (151)
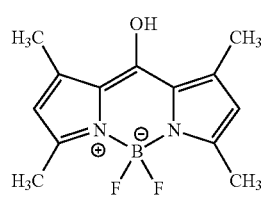
Compound (152)
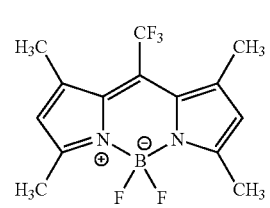
Compound (153)
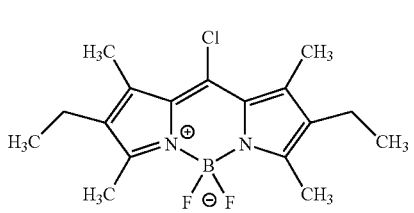
Compound (154)
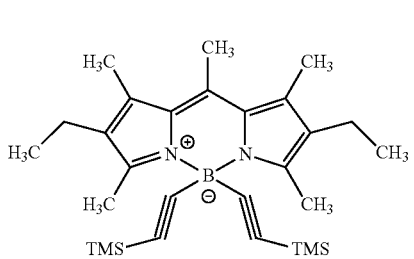
Compound (155)
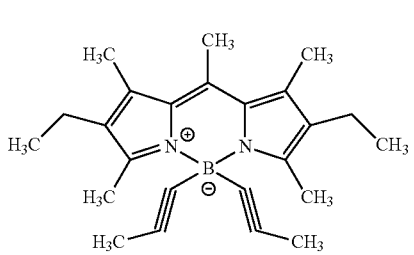
Compound (156)
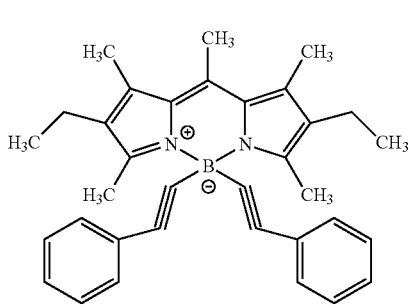
Compound (157)
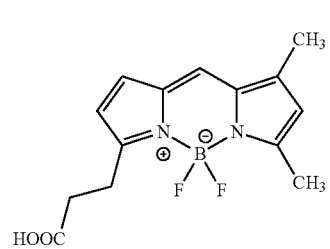
Compound (158)
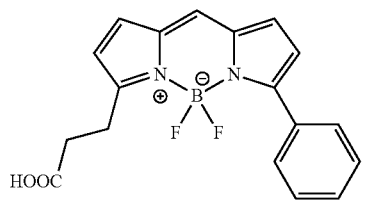

Compound (159)
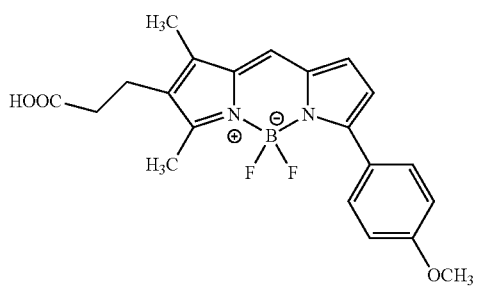
Compound (160)
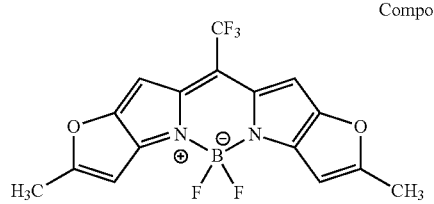
Compound (161)
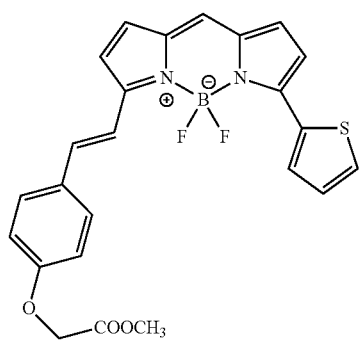
Compound (162)
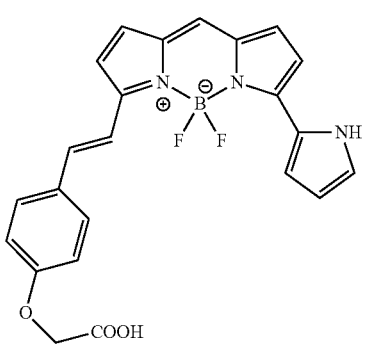
Compound (163)
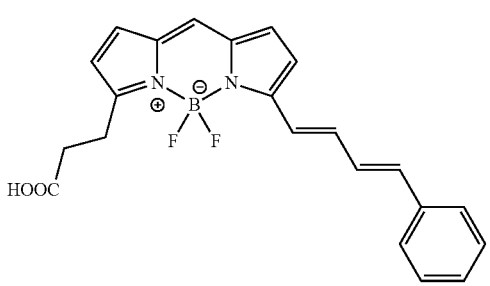
Compound (164)
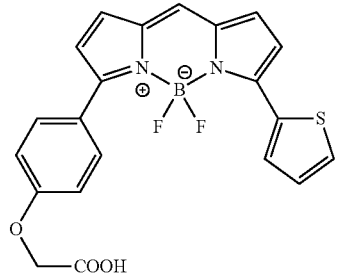
Compound (165)
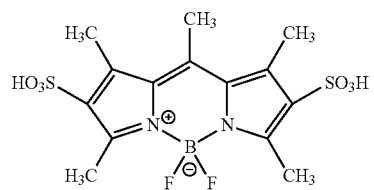
Compound (166)
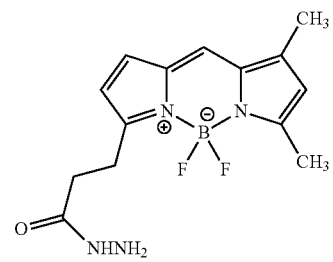
Compound (167)
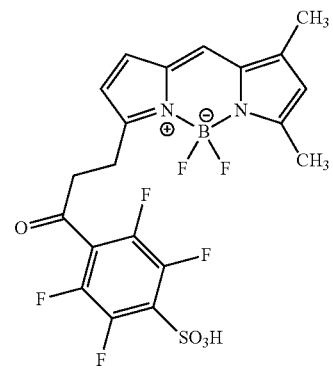
Compound (168)
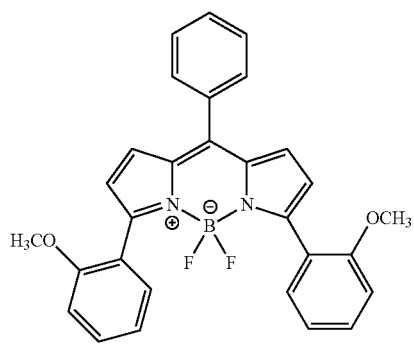

-continued

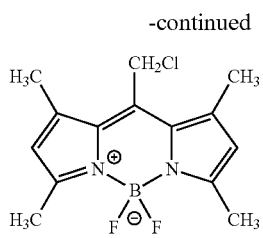

Compound (169)

The organic compounds of the present invention can be organic compounds having a molecular weight less than 10,000, preferably 5,000 or less, and more preferably 2,000 or less. Besides, the organic compounds of the present invention are preferably dye compounds, and more preferably fluorescent compounds having fluorescent characteristics. Since a fluorescent compound has high sensitivity, the compound can be used for staining at a low concentration, and hence, the necessary amount of compound can be relatively reduced.

The wavelength for exciting each of the organic compounds represented by general formulas (1), (6), (10) and (11) of the present invention is not especially limited, and a wavelength of 200 to 1400 nm is generally used because of the limit of a laser wavelength for generating excitation light and a range of a wavelength that can be easily transmitted through a living body. The wavelength can be 340 to 800 nm because such a wavelength falls in to a wavelength range in which fluorescence can be detected by various types of apparatuses. In particular, if merely one type of compounds represented by general formulas (1), (6), (10) and (11) is used, a compound having an excitation wavelength in the vicinity of 455 to 530 nm can be suitably used because an inexpensive versatile apparatus containing a 488 nm laser can be used.

Although it has been revealed that the macrophage subtypes largely affect the pathologic change of an inflammatory disease, the detailed mechanism has not been clarified yet. When the identification agent of the present invention is used, macrophage subtypes can be identified to be visualized, and therefore, the identification agent of the present invention can be used as a research reagent for clarifying the relationship between the pathologic change of an inflammatory disease and a subtype. Furthermore, since there are a large number of reports that a subtype reflects the pathologic change of an inflammatory disease, the identification agent of the present invention can be used as a labeling agent for a subtype to be used for determining or diagnosing the pathology of an inflammatory disease in the research or clinical field. The identification agent of the present invention can be used as a labeling agent for making pathological diagnosis in vitro or ex vivo, or a labeling agent for making diagnosis in vivo with an endoscope or the like.

<Regarding Macrophages>

In the present invention, subtypes are not especially limited as long as the subtypes are those different in the function, the expression gene, the expression protein, the cell producing substance such as a protein or a low-molecular weight substance, or the like, but herein refer to the M1 macrophage and the M2 macrophage.

The M1 macrophage herein is not especially limited as long as the M1 macrophage has functions of immune activation, promotion of inflammation, disinfection, antitumor and the like. Examples include macrophages having a large amount of proteins, expressed on cell surfaces, such as cluster of differentiation (hereinafter referred to as CD) 16, CD32, CD64, CD80, CD169 and lymphocyte antigen 6C, macrophages producing a large amount of inflammatory proteins such as tumor necrosis factor-α (hereinafter referred to as TNF-α), interleukin-6 (hereinafter referred to as IL-6), interleukin-12, interleukin-23 and interleukin-1β, macrophages producing a small amount of anti-inflammatory proteins such as interleukin-10 (hereinafter referred to as the IL-10), macrophages producing a large amount of proteins such as CC chemokine ligand 2, CC chemokine ligand 3, CC chemokine ligand 4, CC chemokine ligand 5, CC chemokine ligand 9, CC chemokine ligand 10, CC chemokine ligand 11, CXC chemokine ligand 9, CXC chemokine ligand 10, and CXC chemokine ligand 11, macrophages producing a large amount of reactive nitrogen species such as nitrogen monoxide or reactive oxygen species, and macrophages expressing, at high expression level, genes of any of the aforementioned proteins, inducible nitric monoxide synthase (hereinafter referred to as the iNOS) or the like.

The M2 macrophage herein is not especially limited as long as the M2 macrophage has functions of suppression of immune or inflammation, healing of wound, tissue remodeling, vascularization, promotion of tumor growth and the like. Examples include macrophages having a large amount of proteins, expressed on cell surfaces, such as CD163, CD206, CD204, CD209, CD301, Dectin-1 and Galectin-3, macrophages producing a large amount of anti-inflammatory proteins such as IL-10, interleukin-1RA and a decoy receptor for interleukin-1, macrophages producing a small amount of inflammatory proteins such as interleukin-12, macrophages producing a large amount of proteins such as CC chemokine ligand 1, CC chemokine 16, CC chemokine ligand 17, CC chemokine ligand 18, CC chemokine ligand 22, CC chemokine ligand 24, CXC chemokine ligand 3, CXC chemokine ligand 4, CXC chemokine ligand 23 and transforming growth factor μ (hereinafter referred to as the TGF-β), macrophages producing a large amount of polyamine, and macrophages expressing, at high expression level, genes of any of the aforementioned proteins, arginase-1 (hereafter referred to as the Arg1), Ym1, FIZZ1 and the like.

<Regarding Biological Sample>

A biological sample used in the present invention is not especially limited, and the biological sample can be, for example, a biont, a biological tissue, a biological tissue section, a biological tissue block, human cells, animal cells, human cultured cells, or animal cultured cells. The biological sample may be precedently fixed with formalin or the like.

Examples of species for the biological sample of, for example, vertebrates include a teleost such as tiger puffer, grass puffer, green spotted puffer, killifish, or zebra fish; an amphibian such as a *xenopus*; a bird such as a chicken or a quail; a small animal such as a rat, a mouse or a hamster; a large animal such as a goat, a pig, a dog, a cat, a rabbit, a bovine or a horse; and a primate such as a monkey, a chimpanzee or a human.

Examples of species for the biological sample of invertebrates include a fruit fly and a roundworm.

Examples of the biological sample of cultured cells include cultured cells derived from normal tissues of any of the aforementioned species, or derived from various diseased tissues.

In some cases, cells of a specific subtype may be produced by culture, so as to be used for screening or the like.

A method for producing cells by culture is not especially limited as long as precursor cells of macrophages of monocytes or the like are stimulated by a specific cytokine or the like to be differentiated into a desired subtype.

The M1 macrophage can be produced, for example, by adding a macrophage colony stimulating factor (hereinafter referred to as the M-CSF), a granulocyte macrophage colony stimulating factor or phorbol myristate acetate (hereinafter referred to as the PMA) to a medium for culturing precursor cells of macrophages collected from a bone marrow, a spleen, a tissue, a blood or the like. Alternatively, in addition to the administration of the M-CSF, the granulocyte macrophage stimulating factor or the PMA, either of protein combinations of interferon-γ and lipopolysaccharide, and interferon-γ and a tumor necrosis factor may be added for producing the M1 macrophage.

The M2 macrophage can be produced, for example, by adding an M-CSF, a granulocyte macrophage stimulating factor or the PMA to a medium for culturing precursor cells of macrophages collected from a bone marrow, a spleen, a tissue, a blood or the like. Alternatively, in addition to the administration of the M-CSF, the granulocyte macrophage stimulating factor or the PMA, any of proteins and protein combinations out of interleukin-4 (hereinafter referred to as the IL-4), interleukin-13 (hereinafter referred to as the IL-13), IL-4 and IL-13, IL-10, an immune complex and interleukin-1β, an immune complex and lipopolysaccharide, an immune complex and a toll-like receptor, and an immune complex and interleukin-1 receptor ligand may be added for producing the M2 macrophage.

On the other hand, for purpose of developing a treatment method, in a case where, for example, a subtype present in a biological sample or in vivo is to be changed to another subtype, or macrophage having been changed in the subtype in vitro is intravitally administered to find the effect of the subtype change, the subtype can be changed by a method similar to that described above.

Identification Method

Embodiment 5 of the present invention provides a method for identifying the macrophage subtypes M1 and M2, specifically, a method for identifying the macrophage M1 and the macrophage M2 based on spectral characteristics obtained with an organic compound added. The organic compound is not especially limited but can be a dye compound having a molecular weight of 2000 or less.

In the identification method of the present embodiment, the M1 macrophage or the M2 macrophage contained in a biological sample is identified preferably by utilizing a difference in staining properties between the M1 macrophage and the M2 macrophage.

In the present embodiment, the organic compound can be a macrophage identification agent of the present invention.

The identification method of the present embodiment can be performed, after staining a biological sample by exposing the macrophage identification agent of the present invention to the biological sample, by a flow cytometry method or by using an identifying apparatus such as a fluorescence activated cell sorting (hereinafter referred to as FACS). The subtypes can be identified by using such an apparatus by utilizing a difference in the staining properties depending upon the subtypes.

The difference in the staining properties is not especially limited, but can be, for example, a difference in the amount or speed for import of the macrophage identification agent into cells, a difference in the amount or speed for extracellularly export of the macrophage identification agent having been imported into cells, a difference in the interaction of the macrophage identification agent on cell surfaces of the subtypes, and a difference in the fluorescence intensity of the macrophage identification agent depending upon the subtypes.

Alternatively, a stained biological sample may be observed with a fluorescence microscope, so as to make identification in an image based on a difference in the fluorescence intensity derived from a difference in the abundance of the macrophage identification agent in cells or on cell surfaces depending upon the subtypes.

Alternatively, a plurality of excitation lights can be used for irradiation and a plurality of types of fluorescence can be detected, so that fluorescence derived from the macrophage identification agent can be detected by using a combination of a plurality of excitation light and fluorescence wavelengths. When a plurality of excitation light and fluorescence wavelengths are thus combined, useful information for identifying the subtypes can be obtained.

In performing the identification by the flow cytometry method or by using the identifying apparatus such as an FACS, optical characteristics such as forward scattering and side scattering can be simultaneously used for removing, from signals detected by the identifying apparatus, signals derived from particles other than cells. Besides, the identification can be performed merely on living cells by staining dead cells with a dead cell detection reagent. As the dead cell detection reagent, a commercially available reagent can be suitably used.

In employing the observation with a fluorescence microscope, if an image of a biological sample is captured while allowing the compound used as the macrophage identification agent to emit light in cells or on cell surfaces by irradiating the biological sample with excitation light, a light emitting portion and a non-light emitting portion can be easily detected. Besides, if a bright field image obtained by irradiation with visible light and a fluorescent image obtained by irradiation with excitation light are combined with each other by using image processing means, distributions of the subtypes in the biological sample can be observed in more details. Furthermore, a confocal microscope can be used because an optical section image can be thus obtained. Besides, a multiphoton excitation fluorescence microscope can be suitably used for observing the inside of a biological sample because this type of microscope has deep tissue penetration and high spatial resolution.

The macrophage subtypes can be identified by the identification method of the present invention, and therefore, the identification method of the present invention can be used for clarifying the relationship between the pathologic change of an inflammatory disease and the subtypes. Besides, the identification method of the present invention can be used for determining or diagnosing the pathology of an inflammatory disease in the research or clinical field.

<Staining>

In staining cells by exposing the macrophage identification agent of the present invention to the biological sample, the compound represented by general formula (1) may be directly used, or may be dissolved in a suitable solvent before use.

The solvent used in the present invention is not especially limited, and examples of the solvent include water, physiological saline, a buffer such as a phosphate buffered saline (hereinafter referred to as PBS) or a Tris buffer, a cell culture medium such as a Dulbecco's Modified Eagle Medium (hereinafter referred to as D-MEM), an Iscove's Modified Dulbecco's Medium (hereinafter referred to as IMDM), a Hanks' Balanced Salt Solutions (hereinafter referred to as HBSS), Minimun Essential Medium-Eagle, Earle's Salts Base, with Non-Essential Amino Acid (hereinafter referred to as the MEM-NEAA), or Roswell Park Memorial Institute Medium (hereinafter referred to as RPMI) 1640, a commercially available buffer for FACS analysis, and an infusion solution such as a lactated Ringer's solution. Such a solvent can particularly contain water by 50% or more. Besides, a mixture of two or more of these solvents can be used.

On the other hand, to such a solvent, a serum such as a fetal bovine serum (hereinafter referred to as the FBS) or a horse serum, or an antibacterial agent such as sodium azide or penicillin-streptomycin (hereinafter referred to as the P/S) can be added before use. In particular, a physiological saline, a buffer such as a PBS or a Tris buffer, a cell culture medium such as a D-MEM, an IMDM, or a HBSS, a commercially available buffer for FACS analysis, or an infusion solution such as a lactated Ringer's solution can be suitably used from the viewpoint of controlling a salt concentration, pH and the like to be suitable for cells.

The compound represented by general formula (1) can be dissolved, before mixing with the aforementioned solvent, in an organic solvent such as dimethyl sulfoxide (hereinafter referred to as DMSO) or ethanol as long as the organic solvent is used at a concentration not affecting the biological sample.

Another additive may be added if necessary. The additive used in the present invention is not especially limited as long as the staining of macrophages is not affected, and examples of the additive include a humectant, a surface tension adjuster, a thickener, a salt such as sodium chloride, any of various pH adjusters, a pH buffer solution, an antiseptic agent, an antibacterial agent, a sweetener and a perfume. One of these additives may be singly used, or more of these additives may be used in combination.

The concentration of the compound represented by general formula (1) in the macrophage identification agent of the present invention is not especially limited as long as the compound is used in an amount sufficient for identifying the subtypes, and can be appropriately decreased/increased according to the state of a sample in which a target subtype is present. In general, the compound is used in a concentration of 0.001 nM or more and 1000 µM or less, and more preferably in a concentration of 0.01 nM or more and 100 µM or less. Particularly when the compound is used in vivo, the amount of the compound can be as small as possible.

One of the compounds represented by general formula (1) for the macrophage identification agent of the present invention can be singly used, or two or more of the compounds may be used in combination. Besides, two or more of the compounds represented by general formula (1) for the macrophage identification agent of the present invention can be used in combination with a known fluorescent dye.

The staining of cells by exposing the macrophage identification agent of the present invention to the biological sample can be performed, in the case of a use in vitro or ex vivo, by mixing the biological sample with the macrophage identification agent in a suitable vessel, or bringing the macrophage identification agent into contact with the biological sample on a slide glass or the like by dropping, spraying or the like.

In the case of a use in vivo, the macrophage identification agent may be administered to a living body by orally administering the agent, or by injecting, spraying or applying the agent intravenously or intraarterially intravascularly, orally, sublingually, intrarectally, intraperitoneally, cutaneously, subcutaneously, intravesically, intratracheally (intrabronchially), intraocularly, intranasally or intraaurally. Alternatively, the macrophage identification agent may be used together with a probe of an endoscope such as a catheter.

The temperature at which the staining is performed is not especially limited, but the macrophage identification agent is exposed to the biological sample at a temperature of preferably 4 to 42° C., more preferably 4 to 38° C., further more preferably 31 to 38° C. and most preferably 37° C.

The time for the staining is not especially limited, but the macrophage identification agent is exposed to the biological sample for preferably 1 minute or more and 24 hours or less, more preferably 1 minute or more and 4 hours or less, and further more preferably 1 minute or more and 1 hour or less. The staining can be performed generally in 1 hour.

<Staining Mechanism>

The macrophage identification agent of the present invention can identify a subtype based on a difference in the intensity of fluorescence derived from the macrophage identification agent caused depending on the subtypes, and this difference is caused, for example, for the following reason: Depending on the subtypes, the amount or speed for import of the macrophage identification agent into cells is different, or the amount or speed for extracellularly export of the macrophage identification agent having been imported into cells is different, the interaction of the macrophage identification agent, having been imported into cells, with a component present in the cells, such as a high molecular weight substance, a low molecular weight substance, a gaseous molecule, or an ion, is different depending on the subtypes, or the interaction of the macrophage identification agent with cell surfaces is different depending on the subtypes.

The macrophage identification agent of the present invention works as a substrate of at least one or more transporters expressed on cell surfaces of a subtype, and therefore, the amount or speed for import of the macrophage identification agent into cells or the amount or speed for extracellularly export of the macrophage identification agent having been imported into cells is different depending on the subtypes.

Herein, to "work as a substrate of a transporter" means that the agent can be selectively transported by an entry transporter in the absence of an influx transporter inhibitor but cannot be transported in the presence of the influx transporter inhibitor, or that the migration via an influx transporter is changed in the presence of an influx transporter inhibitor. Alternatively, it means that the agent is selectively transported by an efflux transporter, that the agent is transported by an efflux transporter in the absence of an efflux transporter inhibitor but is not transported in the presence of the inhibitor, or that the migration via an efflux transporter is changed in the presence of an efflux transporter inhibitor.

The transporter is not especially limited, and examples include an ABC transporter, an SLC transporter, a glucose transporter and a dopamine transporter. Among these transporters, an efflux transporter is preferred, an ABC transporter is more preferred, and a transporter working as a substrate of Pgp (P-glycoprotein), BCRP (Breast Cancer Resistance Protein), MRP (Multidrug Resistance-associated Protein) or MDR (Multidrug Resistance) is further more preferred.

The macrophage identification agent of the present invention is different in the amount or speed of being imported into cells by endocytosis depending on the subtypes. If the macrophage identification agent of the present invention is modified with a liposome, the macrophage identification agent can be easily imported into cells by endocytosis.

The macrophage identification agent of the present invention shows, depending on the subtypes, a different interaction with a high molecular weight substance such as an enzyme or a protein, a low molecular weight substance such as a lipid, gaseous molecules such as reactive oxygen species or reactive nitrogen species, or ion species such as hydrogen ions present in the cells.

The macrophage identification agent of the present invention shows, depending on the subtypes, a different interaction with cell surfaces. The interaction between the macrophage identification agent and the cell surfaces is caused with at least one or more proteins expressed on the cell surfaces of a subtype, amino acid or a functional group contained in the protein, a cell membrane, a lipid contained in the cell membrane, a charge present on the cell surfaces, a hydrophilic region present on the cell surfaces, a hydrophobic region present on the cell surfaces, or the like.

<Washing>

After the macrophage identification agent of the present invention is exposed to the biological sample, a washing operation may be performed as occasion demands. The washing operation will now be described.

If a cell sample obtained by extraction or culture has been stained, the cell sample is precipitated in a proper vessel by centrifugation for removing the staining solution. Next, a solution not containing a dye compound such as the macrophage identification agent of the present invention (i.e., a washing solution) is added to the resultant for washing.

If a tissue or tissue section has been stained, a washing operation is performed by exposing, in a proper vessel or on a slide glass or the like, the resultant sample to a solution not containing a dye compound such as the macrophage identification agent of the present invention (i.e., a washing solution).

The washed operation may be repeated more than once if necessary. Besides, the biological sample may be allowed to stand in a washing solution for a prescribed period of time. Furthermore, a shaking or heating operation may be performed if necessary.

If the washed biological sample is a sample of cells, in particular, a stirring operation or a filtering operation may be performed so that the cells cannot be aggregated.

Sorting Method

A sorting method for a subtype according to Embodiment 6 of the present invention will now be described.

Through the identification performed by the aforementioned identification method for a subtype for selectively sorting, a subtype of interest can be sorted.

For sorting cells, a commercially available FACS apparatus can be suitably used. Besides, if the identification is performed by using an image, cells can be sorted by selectively collecting or removing cells of a subtype of interest or a subtype other than the subtype of interest. For selectively collecting or removing, an aspirator or the like can be used.

It has been revealed that a specific type of macrophages plays a significant role in healing an inflammatory disease. For example, there are reports on research that the M1 macrophage plays a significant role in removing cancer cells, and that the M2 macrophage plays a significant role in healing nephritis. Since an arbitrary subtype can be sorted by the sorting method for a macrophage subtype of the present invention, the sorting method of the present invention can be utilized in a treatment for an inflammatory disease in which an arbitrary subtype is transplanted in a disease site.

Evaluation Method

An evaluation method for a subtype according to Embodiment 7 of the present invention includes exposing the macrophage identification agent of the present invention to a biological sample.

Besides, in the evaluation method of the present invention, after or simultaneously with exposing the macrophage identification agent to a biological sample, a test substance may be allowed to work on a part or the whole of the biological sample.

The evaluation method of the present invention further includes detecting the staining properties of a subtype with the macrophage identification agent. Thus, the type, number, ratio, optical characteristics or the like of a subtype contained in the biological sample can be evaluated.

If a test substance is allowed to work, an effect of the test substance on the type, number, ratio, optical characteristics or the like of the subtype can be evaluated. At this point, if a biological sample on which the test substance is allowed work and a biological sample on which the test substance is not allowed to work are separately evaluated, the action of the test substance on the subtype can be evaluated based on change in the type, number, ratio or the like of the subtype depending on the presence or absence of the test substance can be evaluated. Two or more types of test substances may be used for evaluating a difference in the action between the test substances.

Since the type, number, ratio or optical characteristics of a macrophage subtype can be detected by the evaluation method of the present invention, the evaluation method of the present invention can be utilized for clarifying the relationship between the pathologic change of an inflammatory disease and a subtype. Besides, in the research or clinical field, the evaluation method of the present invention can be used for determining or diagnosing the pathology of an inflammatory disease. Furthermore, since there are a large number of reports that the balance between the subtypes is correlated with the prognosis or recurrence of an inflammatory disease, the evaluation method of the present invention can be used for predicting the prognosis or recurrence of an inflammatory disease. In addition, if the change in subtype caused after administering a drug is examined by the evaluation method of the present invention, a therapeutic drug can be developed, an optimal therapeutic drug can be selected, or the effect of a selected therapeutic drug can be evaluated.

Analysis Method

In Embodiment 8 of the present invention, an analysis method in which a macrophage identification agent is exposed to a biological sample simultaneously with, before or after exposing a test substance to the biological sample so as to analyze staining properties of a subtype is provided. The test substance may be a substance affecting or not affecting the staining properties of the subtype with the macrophage identification agent. Besides, two or more types of test substances may be used for analyzing a difference in the action between the test substances.

In using a test substance affecting the staining properties of a subtype with the macrophage identification agent, if a biological sample on which the test substance is allowed to work and a biological sample on which the test substance is not allowed to work are separately evaluated, the influence of the test substance on the staining properties can be evaluated. Thus, the correlation between the test substance and a transporter expressed on surfaces of cells in which the macrophage identification agent works as a substrate, or a protein, a functional group or the like expressed on surfaces of cells with which the macrophage identification agent interacts can be analyzed.

In using a test substance not affecting the staining properties of a subtype with the macrophage identification agent, the correlation between the subtype identified based on the staining properties with the macrophage identification agent and the test substance can be analyzed. A test substance not affecting the staining properties of a subtype with the macrophage identification agent may be a substance affecting or not affecting the subtype.

In using a test substance not affecting the staining properties of a subtype with the macrophage identification agent but affecting the subtype, if a biological sample on which the test substance is allowed to work and a biological sample on which the test substance is not allowed to work are separately evaluated, the action of the test substance on the subtype can be evaluated based on change in the type, number, ratio or the like of the subtype depending upon the presence or absence of the test substance.

In using a test substance affecting neither the staining properties of a subtype with the macrophage identification agent nor the subtype, optical characteristics derived from the test substance may be measured for detecting the interaction between the test substance and the subtype. If a test substance or a material used for labeling the test substance has fluorescence, the interaction between the test substance and the subtype can be detected by fluorescence measurement. For accurately performing the analysis, the test substance or the material used for labeling the test substance can be selected to have a different excitation wavelength or a different fluorescence wavelength from that of the macrophage identification agent of the present invention. If the excitation wavelength or the fluorescence wavelength is different, the binding, incorporation or the like of the test substance to the subtype can be analyzed by detecting a fluorescent signal derived from the macrophage identification agent and a fluorescent signal derived from the test substance or the material used for labeling the test substance. The test substance having fluorescence is not especially limited, and may be a fluorescent surface antigen marker, or an organic or inorganic molecule having fluorescence.

If the correlation between a subtype and a drug (i.e., change in the subtype caused after administering a drug) is examined by the analysis method of the present invention, a therapeutic drug can be developed, an optimal therapeutic drug can be selected, or the effect of a selected therapeutic drug can be analyzed.

Screening Method

In Embodiment 9 of the present invention, a screening method in which a macrophage identification agent is exposed to a biological sample simultaneously with, before or after exposing a substance to the biological sample so as to screen the substance based on the staining properties of a subtype is provided. In the screening, the evaluation method or the analysis method of the present invention described above can be used, so as to evaluate or analyze the effect or the interaction of a plurality of test substances on or with the subtype.

For example, a biologically active substance working on the action of influx and efflux transporters of a compound expressed in a subtype can be evaluated. In particular, the action of an efflux transporter can be suitably evaluated. More preferably, an ABC transporter can be evaluated. In using the macrophage identification agent of the present invention, if the action of an efflux transporter is inhibited by the influence of a biologically active substance and hence the subtype is poorly separated or satisfactorily separated, or is not different from other cells, it can be evaluated that the biologically active substance acts on the efflux transporter.

Alternatively, if a fluorescent labeled anti-surface antigen antibody is used as a test substance in order to examine a surface antigen expressed in a subtype identified by the macrophage identification agent, a type of antibody having a high affinity with the subtype can be screened.

Alternatively, if a fluorescent substance unknown in the incorporation or interaction into or with a subtype is used as a test substance, the function of the test substance on a subtype identified by the macrophage identification agent can be evaluated based on fluorescence intensity.

There are a large number of reports stating that a specific type of macrophage plays a significant role in healing a disease in addition to reports stating that a subtype reflects the pathologic change of an inflammatory disease, and therefore, a therapeutic drug can be developed, an optimal therapeutic drug can be selected or the effect of a selected therapeutic drug can be screened by examining the correlation between a subtype and a drug (i.e., change in the subtype caused after administering a drug) by the screening method of the present invention.

Kit

An identification kit according to Embodiment 10 of the present invention contains at least one or more macrophage identification agents of the present invention. Besides, although not especially limited, the identification kit can contain a vessel, a reagent and the like necessary for exposing the macrophage identification agent to a biological sample.

By using the identification kit of the present invention, an inflammatory disease can be simply diagnosed in situ at the home, in a place for medical examination or in an emergency medical scene.

The present invention will now be described in more details with reference to examples, and it is noted that these examples are described merely for making the present invention more deeply understood and do not limit the present invention at all.

EXAMPLES

Synthetic Example 1

As an example of the macrophage identification agent represented by general formula (1) of the present invention, a synthetic example of the compound (1) will be described.

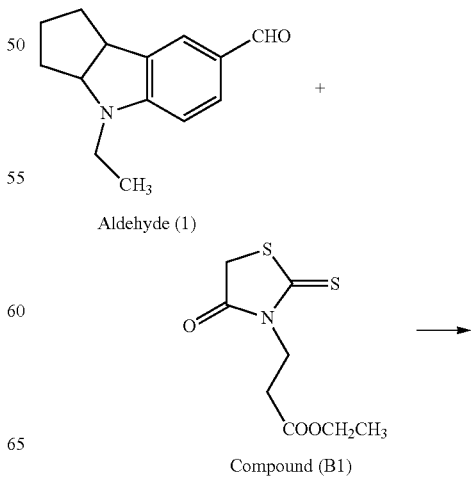

Aldehyde (1)

Compound (B1)

-continued

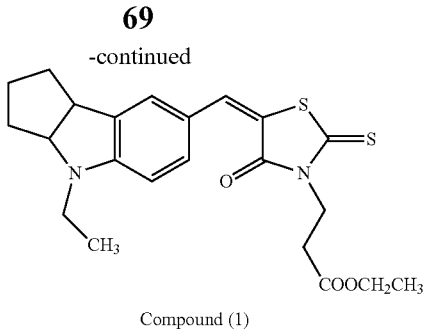

Compound (1)

To a 20 mL acetic acid solution of 2.5 g (11.4 mmol) of aldehyde (1), 2.7 g (11.5 mmol) of a compound (B1) and 1.6 g of ammonium acetate were added, and the resulting solution was stirred for 2 hours under reflux. After completing the reaction, 50 mL of water was slowly added dropwise thereto while cooling, and the resulting solution was cooled to room temperature. The thus deposited solid was filtered out, washed with 100 mL of water twice, and further washed with 50 mL of 2-propanol, thereby obtaining 3.0 g (yield: 60.1%) of the compound (1) of interest.

The obtained substance was confirmed to be the compound (1) of interest by $^1$H nuclear magnetic resonance spectrometric analysis (ECA-400, manufactured by JEOL Ltd.) and LC/TOF MS (LC/MSD TOF, manufactured by Agilent Technologies, Inc.).

<Other Compounds Represented by General Formula (1)>

In the same manner as in Synthetic Example 1, compounds shown in Table 4 were synthesized and identified as the compounds of interest.

Subtype Identification by Using Macrophage Identification Agent Represented by General Formula (1)

Example 1

<Culture of Subtypes>

The culture of subtypes was performed according to a protocol described in NPL 7. Specifically, bone marrow cells collected from the femur of a Balb/c mouse of 8 to 10 weeks old were dispersed to a concentration of $1\times10^6$/mL in an IMDM containing 20% FBS and 1% P/S, and $1\times10^7$ cells were seeded in a 100 mm dish. After further adding an M-CSF (manufactured by Pepro Tech) thereto to a concentration of 50 ng/mL, the cells were incubated for 3 to 4 days in the presence of 5% $CO_2$ at 37° C., so as to differentiate macrophage precursor cells to macrophages. After exchanging the medium, the M-CSF was added to a concentration of 50 ng/mL, and the incubation was performed for further 3 to 4 days in the presence of 5% $CO_2$ at 37° C., and then, the resulting cells were differentiated to macrophage. By adding 200 ng of interferon-γ and 1 μg of polyliposaccharide (both manufactured by Pepro Tech) to the IMDM containing 5% FBS and 1% P/S, the cells were differentiated to the subtype M1. Besides, by adding 100 ng of IL-4 to the IMDM containing 5% FBS and 1% P/S, the cells were differentiated to the subtype M2. After performing the incubation for further 3 days in the presence of 5% $CO_2$ at 37° C., the resultant was rinsed with PBS, and PBS containing 0.25% trypsin and 1 mM EDTA (ethylenediaminetetraacetic acid) was used for collecting, from the dish, the macrophages having been differentiated to the subtypes M1 and M2.

<Confirmation of Subtypes>

The thus collected M1 and M2 macrophages were subjected to gene expression analysis for confirming that the cells had been differentiated to the subtypes. From a part (approximately 0.5 to $5\times10^6$ macrophages) of each of the M1 macrophages and the M2 macrophages thus collected, total RNA was extracted according to a protocol attached to RNeasy mini kit manufactured by Qiagen. Thereafter, cDNA was synthesized by reverse transcription performed according to a protocol of SuperScript® VILO™ cDNA Synthesis Kit (manufactured by Invitrogen). Primers for cDNAs of M1 macrophage marker genes (iNOS and TNFα) and cDNA of M2 macrophage marker genes (Arg1 and CD206) were synthesized. The sequences of the synthesized primers are shown in Table 2. A polymerase chain reaction was performed by using Applied Biosystems 7500 Real-Time PCR system according to a protocol of PowerSYBR® Green PCR Master Mix (manufactured by Applied Biosystems), so as to quantitatively determine the expression level of each marker gene. FIG. 1 illustrates a result of comparison in the expression level among the marker genes obtained from the cells having been differentiated to the M1 macrophages and the M2 macrophages. RQ (Relative Quantification) on the ordinate indicates the expression level of each marker gene obtained from the cells differentiated to the M2 macrophages shown as a relative value obtained by assuming that the expression level of the marker gene obtained from the cells differentiated to the M1 macrophage is 1. As is obvious from FIG. 1, the expression levels of the iNOS and the TNFα were higher in the cells differentiated to the M1 macrophages than in the cells differentiated to the M2 macrophages. On the other hand, the expression levels of the Arg1 and the CD206 were higher in the cells differentiated to the M2 macrophages than in the cells differentiated to the M1 macrophages. It was confirmed based on this result that the M1 macrophages and the M2 macrophages could be prepared by the differentiation.

TABLE 2

| Target gene | Sequence of primer | | Remarks |
| --- | --- | --- | --- |
| | Forward | Reverse | |
| GAPDH | TGAAGCAGGCATCTGAGGG | CGAAGGTGGAAGAGTGGGAG | Endogenous control gene |
| iNOS | AGACCTCAACAGAGCCCTCA | TCGAAGGTGAGCTGAACGAG | M1 macrophage marker |
| TNFα | ACGGCATGGATCTCAAAGAC | AGATAGCAAATCGGCTGACG | M1 macrophage marker |

TABLE 2-continued

| Target gene | Sequence of primer Forward | Reverse | Remarks |
|---|---|---|---|
| Arg1 | CTCCAAGCCAAAGTCCTTAGAG | AGGAGCTGTCATTAGGGACATC | M2 macrophage marker |
| CD206 | CGGTGAACCAAATAATTACCAAAAT | GTGGAGCAGGTGTGGGCT | M2 macrophage marker |

<Staining of Subtypes>

Two×10⁵ each of the thus collected M1 and M2 subtypes were dispensed into a 1.5 mL tube, the compound (1) was added thereto to a concentration of 1 µM, and the resultant was incubated at 37° C. for 30 minutes. Thereafter, the tube was centrifuged at 180 G for 10 minutes to remove the supernatant, a dye for identifying dead cells (aqua fluorescent reactive dye, manufactured by Invitrogen; which is hereinafter sometimes abbreviated as aqua) was added thereto, and the resultant was incubated at 4° C. for 10 minutes. Subsequently, the tube was centrifuged at 180 G for 10 minutes to remove the supernatant, cells were suspended in a FACS buffer to be analyzed by using FACSCanto (trademark) II flow cytometry apparatus manufactured by BD.

<Subtype Identification>

Figure 2:
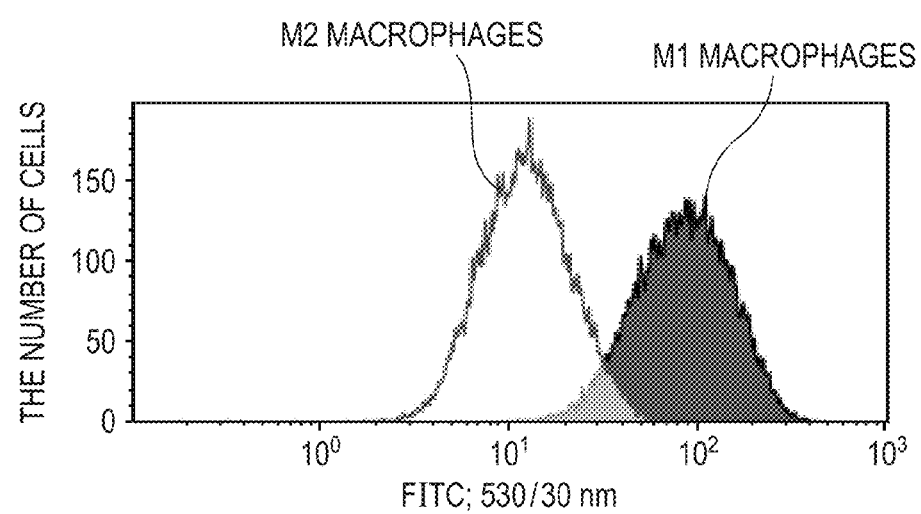
FIG. 2 illustrates a histogram observed in Example 1.

The analysis was performed on a cell population showing a low signal for the aqua, so as to analyze a cell population from which dead cells were eliminated. A fluorescent signal derived from the compound (1) was measured in a FITC channel (excited at 488 nm, 530/30 nm: center wavelength/wavelength width). A histogram was prepared by plotting fluorescence intensity obtained in the FITC channel on the abscissa and plotting the number of cells at each fluorescence intensity on the ordinate, which is shown in FIG. 2.

Examples 2 to 54

Fluorescent signals derived from the compounds (3), (4), (6), (7), (9), (11) to (13), (15), (17), (19) to (26), (28), (30) to (33), (35), (36), (38), (42) to (45), (48) to (62), (65), (67), (74) to (76), (82), (83) and (85) were analyzed in the same manner as in Example 1 except that the compound (1) used in Example 1 was replaced with the compounds (3), (4), (6), (7), (9), (11) to (13), (15), (17), (19) to (26), (28), (30) to (33), (35), (36), (38), (42) to (45), (48) to (62), (65), (67), (74) to (76), (82), (83) and (85).

Comparative Example 1

Figure 3:
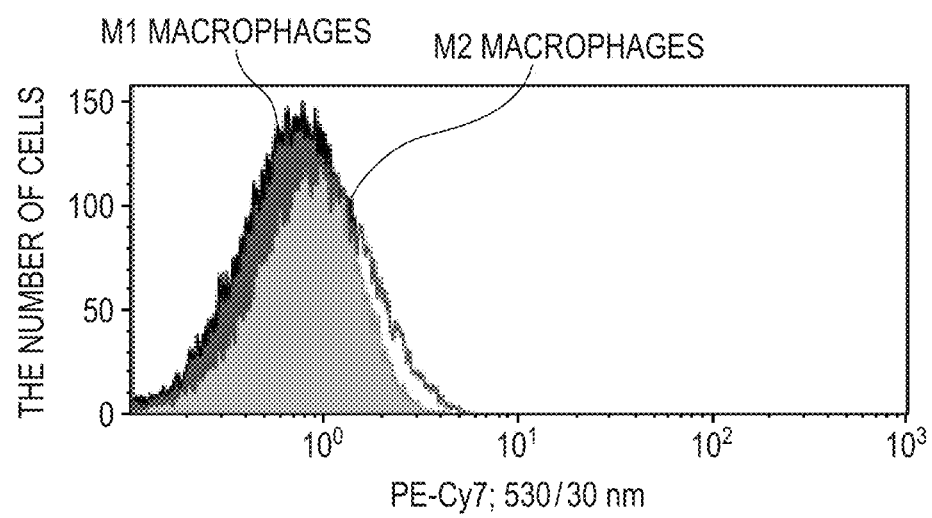
FIG. 3 illustrates a histogram observed in Comparative Example 1.

A fluorescent signal derived from a comparative compound (1) was analyzed in the same manner as in Example 1 except that the compound (1) used in Example 1 was replaced with the comparative compound (1). However, the fluorescent signal derived from the comparative compound (1) was measured in a PE-Cy7 channel (excited at 488 nm, 780/60 nm: center wavelength/wavelength width). A histogram was prepared by plotting fluorescence intensity obtained in the PE-Cy7 channel on the abscissa and plotting the number of cells at each fluorescence intensity on the ordinate, which is shown in FIG. 3.

Comparative Example 2

Figure 4:
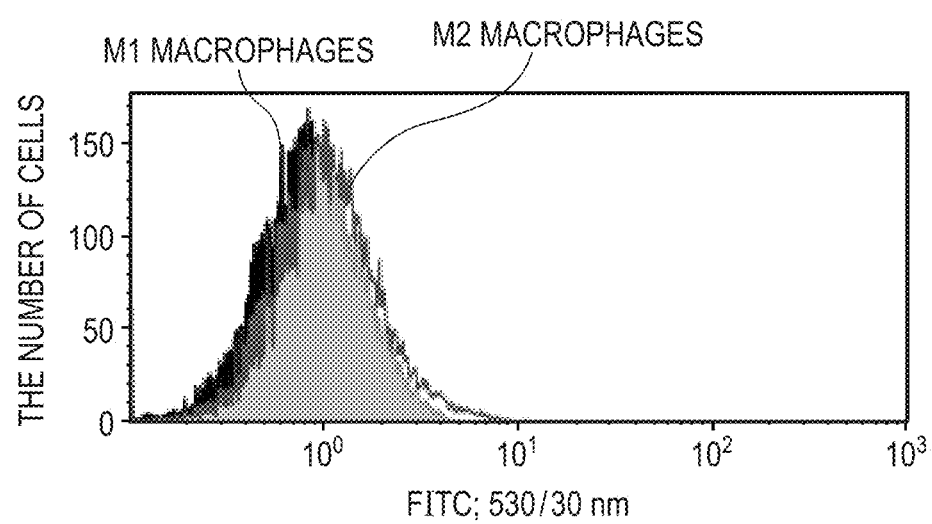
FIG. 4 illustrates a histogram observed in Comparative Example 2.
Figure 5A:
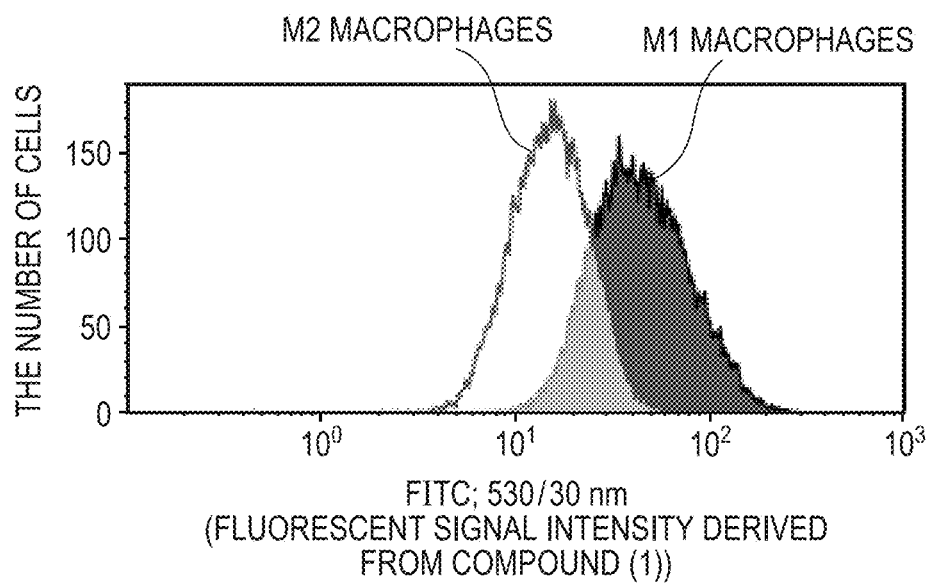
FIGS. 5A, 5B, 5C, 5D and 5E illustrate histograms (FIGS. 5A and 5B) and cytograms (FIGS. 5C, 5D and 5E) observed in Example 55. The cytogram illustrated in FIG. 5C is obtained from M1 macrophages stained with a compound (1) and a compound (33). The cytogram illustrated in FIG. 5D is obtained from M2 macrophages stained with the compound (1) and the compound (33). The cytogram illustrated in FIG. 5E is obtained by overlapping the cytograms illustrated in FIGS. 5C and 5D.
Figure 5B:
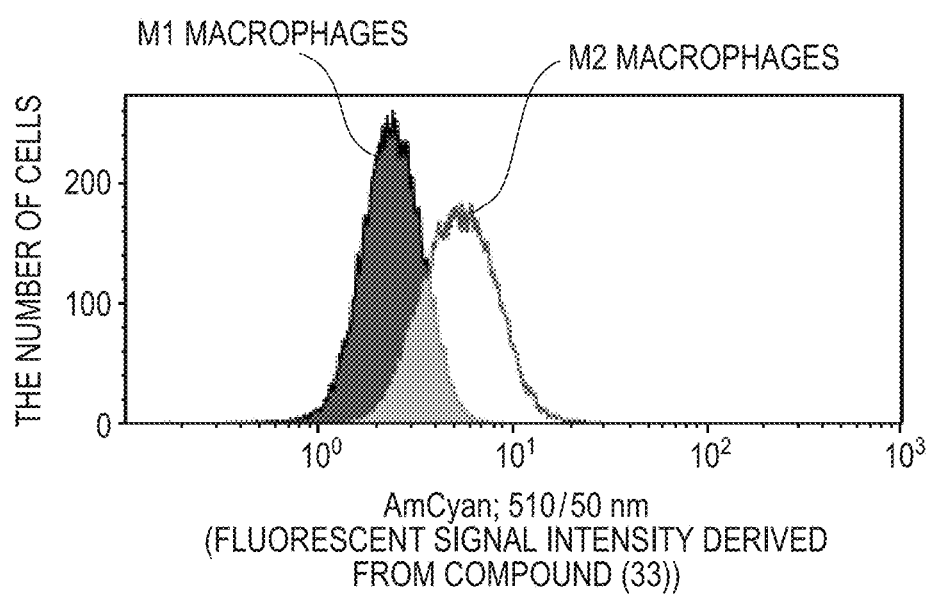
Figure 5C:
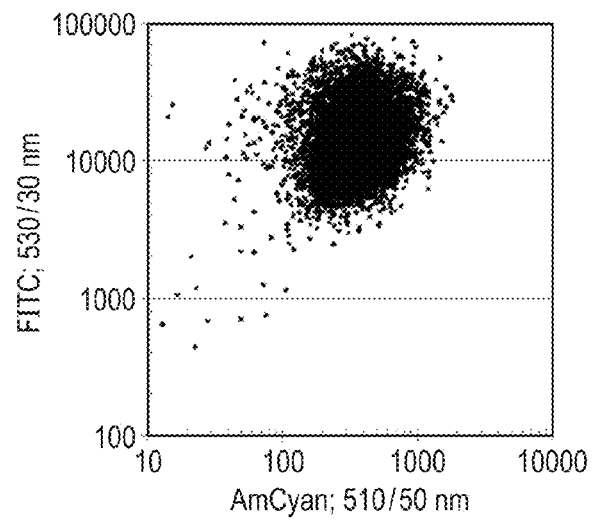
Figure 5D:
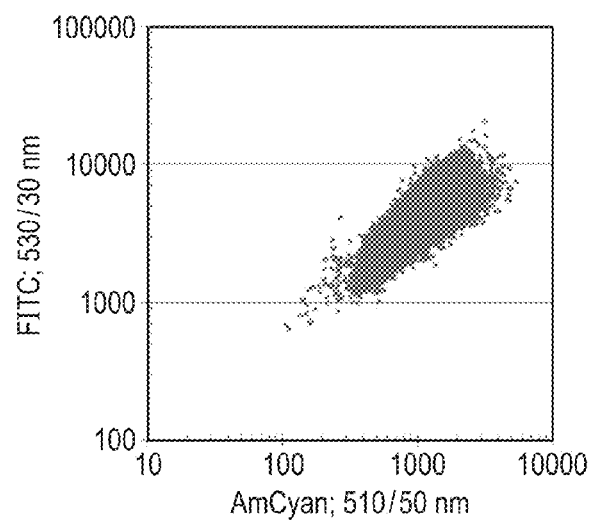
Figure 5E:
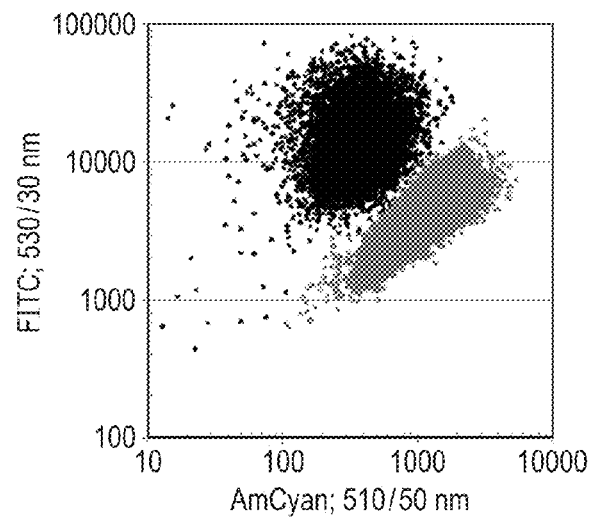

A fluorescent signal derived from a comparative compound (2) was analyzed in the same manner as in Example 1 except that the compound (1) used in Example 1 was replaced with the comparative compound (2). A histogram was prepared by plotting fluorescence intensity obtained in the FITC channel on the abscissa and plotting the number of cells at each fluorescence intensity on the ordinate, which is shown in FIG. 4.

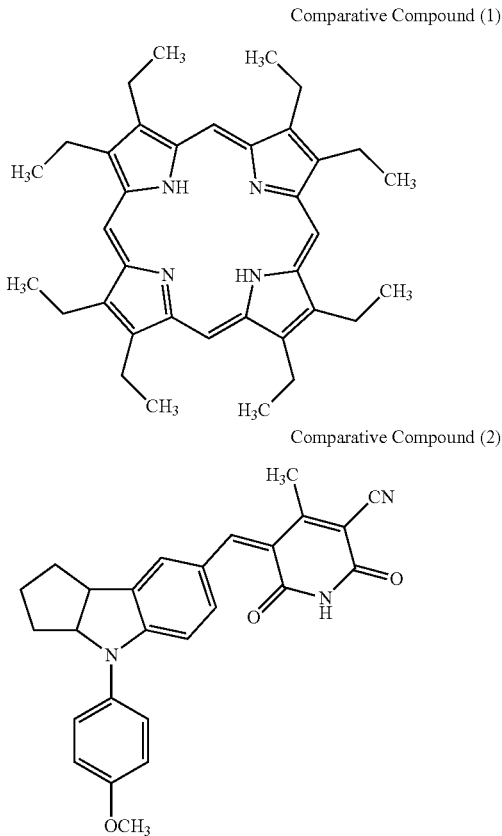

Comparative Compound (1)

Comparative Compound (2)

The results obtained in Examples 1 to 54 and Comparative Examples 1 and 2 described above are shown in Table 4.

<Evaluation Method for Identification Ability of Macrophage Identification Agent Represented by General Formula (1)>

The fluorescent signals derived from the compounds (3), (4), (6), (7), (9), (11) to (13), (15), (17), (19) to (26), (28), (30) to (33), (35), (36), (38), (42) to (45), (48) to (62), (65), (67), (74) to (76), (82), (83) and (85) and the comparative compounds (1) and (2) were measured in channels suitable to the respective compounds. Histograms were prepared by plotting fluorescence intensities obtained in the respective channels on the abscissa and plotting the numbers of cells at each fluorescence intensity on the ordinate. A difference between a fluorescence intensity ($F_{M1}$) at a peak top of the histogram of the M1 macrophage and a fluorescence intensity ($F_{M2}$) at a peak top of the histogram of the M2 macrophage is divided by a sum of a peak width ($W_{M1}$) of the histogram of the M1 macrophage and a peak width ($W_{M2}$) of the histogram of the M2 macrophage, so as to obtain a resolution R, which was used as an index of the identification ability for a subtype (see the following expression (1)).

$$\text{Resolution } R = |F_{M1} - F_{M2}|/(W_{M1} + W_{M2}) \qquad \text{Expression (1)}$$

Based on the thus obtained values of the resolution R, the identification abilities for the subtypes of the compounds (3), (4), (6), (7), (9), (11) to (13), (15), (17), (19) to (26), (28), (30) to (33), (35), (36), (38), (42) to (45), (48) to (62), (65), (67), (74) to (76), (82), (83) and (85) and the comparative compounds (1) and (2) were evaluated as any of A to C according to the following criteria, and if the resolution R was 0.15 or more, the compound was determined to be good in the subtype identification.

A: The compound is very good in the subtype identification (namely, the resolution R is 0.5 or more);
B: the compound is good in the subtype identification (namely, the resolution R is 0.15 or more and less than 0.5); and
C: the compound cannot identify the subtypes (namely, the resolution R is less than 0.15).

Besides, with respect to each of the compounds evaluated to have the identification ability rated as A or B among the compounds (3), (4), (6), (7), (9), (11) to (13), (15), (17), (19) to (26), (28), (30) to (33), (35), (36), (38), (42) to (45), (48) to (62), (65), (67), (74) to (76), (82), (83) and (85) and the comparative compounds (1) and (2), a subtype strongly stained, out of the M1 macrophage (M1) and the M2 macrophage (M2), is shown in a column of "Selectivity" in Table 4.

In Table 3, "Channel" refers to the channel used in measuring the fluorescent signal derived from the corresponding compound. The details of the respective channels are shown in Table 3.

TABLE 3

| Channel | Excitation wavelength (nm) | Center wavelength (nm) | Wavelength width (nm) |
|---|---|---|---|
| FITC | 488 | 530 | 30 |
| PE | 488 | 585 | 42 |
| PerCP-Cy5.5 | 488 | 670-735*[1] | |
| PE-Cy7 | 488 | 780 | 60 |
| APC | 633 | 660 | 20 |
| APC-Cy7 | 633 | 780 | 60 |
| Pacific Blue | 405 | 450 | 50 |
| AmCyan | 405 | 510 | 50 |

*[1]Fluorescence wavelength measurement region

TABLE 4

| Example | Compound | Channel | Peak position of M1 macrophage | Peak position of M2 macrophage | Resolution ratio R | Evaluation of macrophage subtype identification | Selectivity |
|---|---|---|---|---|---|---|---|
| Example 1 | (1) | FITC | 85.8 | 12.4 | 1.150 | A | M1 |
| Example 2 | (3) | PE | 11.2 | 25.0 | 0.622 | A | M2 |
| Example 3 | (4) | FITC | 158 | 45.4 | 1.125 | A | M1 |
| Example 4 | (6) | PE-Cy7 | 26.5 | 50.4 | 0.504 | A | M2 |
| Example 5 | (7) | FITC | 65.4 | 23.6 | 0.567 | A | M1 |
| Example 6 | (9) | FITC | 2.63 | 6.69 | 0.828 | A | M2 |
| Example 7 | (11) | PE | 30.5 | 16.2 | 0.544 | A | M1 |
| Example 8 | (12) | PE | 50.7 | 97.7 | 0.594 | A | M2 |
| Example 9 | (13) | PE | 7.74 | 20.4 | 0.714 | A | M2 |
| Example 10 | (15) | PE | 7.52 | 10.5 | 0.700 | A | M2 |
| Example 11 | (17) | FITC | 7.74 | 16.5 | 0.577 | A | M2 |
| Example 12 | (19) | Pacific Blue | 0.90 | 0.64 | 0.319 | B | M1 |
| Example 13 | (20) | PE-Cy7 | 4.47 | 2.10 | 0.290 | B | M1 |
| Example 14 | (21) | FITC | 40.0 | 20.3 | 0.351 | B | M1 |
| Example 15 | (22) | PE-Cy7 | 199 | 313 | 0.389 | B | M2 |
| Example 16 | (23) | PE | 1.10 | 1.48 | 0.185 | B | M2 |
| Example 17 | (24) | PE | 18.1 | 27.6 | 0.347 | B | M2 |
| Example 18 | (25) | PE | 27.4 | 18.2 | 0.346 | B | M1 |
| Example 19 | (26) | PE | 3.51 | 4.49 | 0.202 | B | M2 |
| Example 20 | (28) | PE | 9.54 | 15.8 | 0.431 | B | M2 |
| Example 21 | (30) | PE-Cy7 | 55.1 | 73.9 | 0.257 | B | M2 |
| Example 22 | (31) | PE-Cy7 | 65.1 | 89.0 | 0.248 | B | M2 |
| Example 23 | (32) | PE-Cy7 | 88.7 | 155 | 0.476 | B | M2 |
| Example 24 | (33) | AmCyan | 5.00 | 9.05 | 0.522 | A | M2 |
| Example 25 | (35) | Pacific Blue | 1.15 | 1.29 | 0.192 | B | M2 |
| Example 26 | (36) | Pacific Blue | 5.70 | 3.82 | 0.344 | B | M1 |
| Example 27 | (38) | FITC | 3.74 | 1.63 | 0.724 | A | M1 |
| Example 28 | (42) | FITC | 4.19 | 1.79 | 0.616 | A | M1 |
| Example 29 | (43) | PE | 7.14 | 13.0 | 0.411 | B | M2 |
| Example 30 | (44) | PE | 24.5 | 12.9 | 0.330 | B | M1 |
| Example 31 | (45) | FITC | 18.2 | 4.84 | 0.822 | A | M1 |
| Example 32 | (48) | FITC | 65.4 | 9.74 | 0.621 | A | M1 |
| Example 33 | (49) | PE | 3.26 | 5.02 | 0.486 | B | M2 |
| Example 34 | (50) | FITC | 3.24 | 0.99 | 1.025 | A | M1 |
| Example 35 | (51) | PE-Cy7 | 87.5 | 23.3 | 0.684 | A | M1 |
| Example 36 | (52) | PE | 3.90 | 1.68 | 0.756 | A | M1 |
| Example 37 | (53) | PerCP-Cy5.5 | 128 | 190 | 0.650 | A | M2 |
| Example 38 | (54) | PerCP-Cy5.5 | 154 | 211 | 0.531 | A | M2 |
| Example 39 | (55) | PE | 2.34 | 1.86 | 0.206 | B | M1 |

TABLE 4-continued

| Example | Compound | Channel | Peak position of M1 macrophage | Peak position of M2 macrophage | Resolution ratio R | Evaluation of macrophage subtype identification | Selectivity |
|---|---|---|---|---|---|---|---|
| Example 40 | (56) | PE | 4.90 | 6.36 | 0.207 | B | M2 |
| Example 41 | (57) | PE-Cy7 | 4.20 | 3.59 | 0.167 | B | M1 |
| Example 42 | (58) | PE | 1.67 | 6.20 | 0.698 | A | M2 |
| Example 43 | (59) | APC-Cy7 | 188 | 325 | 0.733 | A | M2 |
| Example 44 | (60) | PE | 4.55 | 7.65 | 0.621 | A | M2 |
| Example 45 | (61) | PE | 2.39 | 3.15 | 0.219 | B | M2 |
| Example 46 | (62) | PerCP-Cy5.5 | 193 | 333 | 0.561 | A | M2 |
| Example 47 | (65) | PE | 2.96 | 4.67 | 0.236 | B | M2 |
| Example 48 | (67) | PE | 8.28 | 27.6 | 0.808 | A | M2 |
| Example 49 | (74) | Pacific Blue | 2.52 | 1.25 | 0.538 | A | M1 |
| Example 50 | (75) | PE-Cy7 | 96.1 | 235 | 0.665 | A | M2 |
| Example 51 | (76) | PerCP-Cy5.5 | 7.77 | 10.5 | 0.283 | B | M2 |
| Example 52 | (82) | Pacific Blue | 3.18 | 1.42 | 0.783 | A | M1 |
| Example 53 | (83) | PE-Cy7 | 20.3 | 10.6 | 0.516 | A | M1 |
| Example 54 | (85) | PE-Cy7 | 225 | 285 | 0.179 | B | M2 |
| Comparative Example 1 | Comparative compound (1) | PE-Cy7 | 1.70 | 1.86 | 0.006 | C | not identified |
| Comparative Example 2 | Comparative compound (2) | FITC | 0.86 | 1.05 | 0.007 | C | not identified |

As is obvious from Table 4 and FIGS. 2 to 4, although there is no difference in the staining intensity between the M1 macrophages and the M2 macrophages stained by using the comparative compound (1) or (2) and hence these macrophages cannot be identified, if the macrophage identification agent containing the dye compound represented by general formula (1) of the present invention is used, the M1 macrophages and the M2 macrophages can be identified from each other based on a difference in the fluorescence intensity.

Example 55

Two×$10^5$ each of M1 macrophages and M2 macrophages cultured in the same manner as in Example 1 were dispensed into a 1.5 mL tube, and the compound (1) and the compound (33) were added thereto each to a concentration of 1 μM. Dead cells were identified by using TO-PRO-3 (manufactured by Invitrogen).

A fluorescent signal derived from the compound (1) was measured in the FITC channel (excitation wavelength: 488 nm, center wavelength: 530 nm, wavelength width: 30 nm) and a fluorescent signal derived from the compound (33) was measured in an AmCyan channel (excitation wavelength: 405 nm, center wavelength: 510 nm, wavelength width: 50 nm). A cytogram developed by plotting the intensity of the fluorescent signal derived from the compound (1) and obtained in the FITC channel on the ordinate and plotting the intensity of the fluorescent signal derived from the compound (33) and obtained in the AmCyan channel on the abscissa was prepared.

The analysis was performed on a cell population showing a low signal for the TO-PRO-3, so as to analyze a cell population from which dead cells were eliminated.

The operation was performed in the same manner as in Example 1 except for the above.

As a result, as is obvious from FIGS. 5A to 5E, when the compound (1) is used, the M1 macrophages are more strongly stained than the M2 macrophages. On the contrary, when the compound (33) is used, the M2 macrophages are more strongly stained than the M1 macrophages. Therefore, the M1 macrophages and the M2 macrophages stained with the compound (1) and the compound (33) are plotted, on the cytogram developed with respect to the intensities of the fluorescent signals derived from these compounds, as cell populations having different fluorescent characteristics, and hence, these macrophages can be easily identified.

This example reveals that the subtypes can be identified even when two or more types of compounds for the macrophage identification agent represented by general formula (1) of the present invention are used in combination.

Sorting of Subtype by Using Macrophage Identification Agent Represented by General Formula (1)

Example 56

One×$10^5$ each of M1 macrophages and M2 macrophages cultured in the same manner as in Example 1 were mixed in a 1.5 mL tube, and the compound (1) was added thereto to a concentration of 1 μM.

The operation was performed in the same manner as in Example 1 except for the above.

Figure 6A:
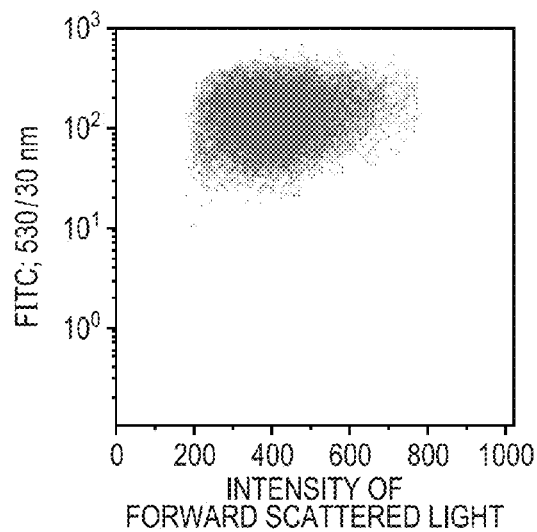
FIGS. 6A, 6B and 6C illustrate cytograms observed in Example 56. The cytogram illustrated in FIG. 6A is obtained from M1 macrophages stained with the compound (1), the cytogram illustrated in FIG. 6B is obtained from M2 macrophages stained with the compound (1), and the cytogram illustrated in FIG. 6C is obtained from a sample of a mixture of the M1 macrophages and the M2 macrophages stained with the compound (1).
Figure 6B:
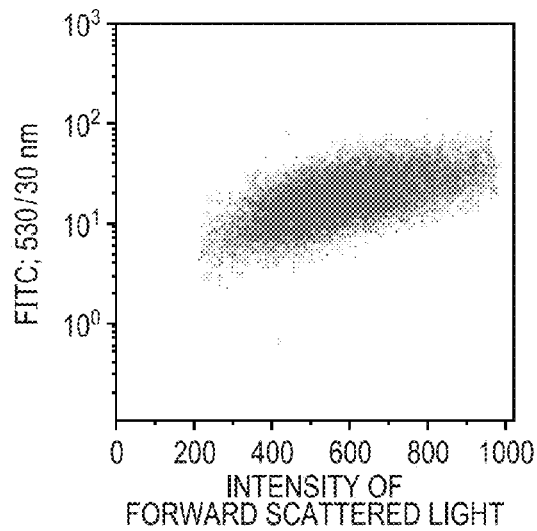
Figure 6C:
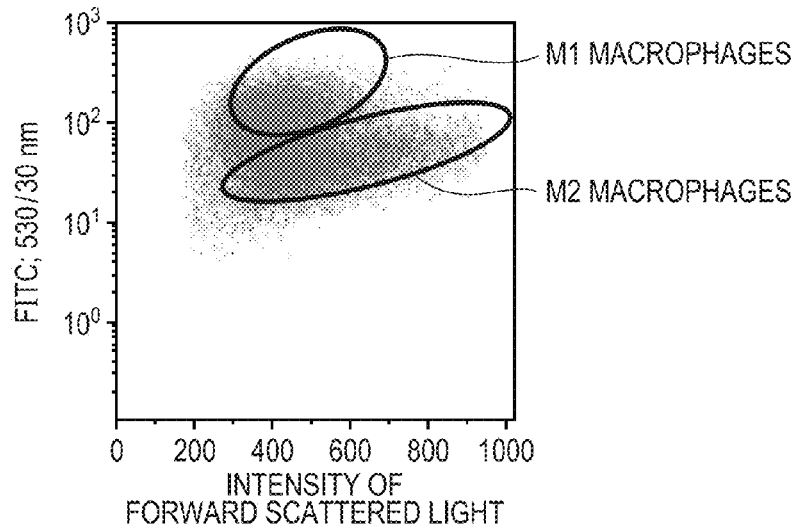

As a result, as is obvious from FIGS. 6A to 6C, the M1 macrophages and the M2 macrophages stained with the compound (1) were plotted, on a cytogram developed with respect to the intensity of forward scattered light affected by the size of cells and the intensity of a fluorescent signal derived from the compound (1), as cell populations having different fluorescence intensity distributions.

Since the compound (1) has a characteristic to stain the M1 macrophages more strongly than the M2 macrophages, the M1 macrophages can be identified as a cell population having a high fluorescence intensity derived from the compound (1), and on the other hand, the M2 macrophages can be identified as a cell population having a low fluorescence intensity derived from the compound (1).

Besides, the M1 macrophages and the M2 macrophages identified by using the compound (1) could be each sorted with an FACS apparatus. The sorted subtypes were confirmed by a fluorescent antibody method and gene expression analysis.

It was found through Examples 1 to 56 described above that the subtypes can be identified and sorted by using the macrophage identification agent represented by general formula (1) of the present invention.

Analysis and Screening of Subtype by Using Macrophage Identification Agent Represented by General Formula (1)

Example 57

Two×$10^5$ each of M1 macrophages and M2 macrophages cultured in the same manner as in Example 1 were dispensed into a 1.5 mL tube, and the compound (1) was added thereto to a concentration of 1 µM. Besides, Fumitremorgin C (manufactured by Sigma-Aldrich, hereinafter referred to as FTC) was added thereto, as a substance for inhibiting export of the compound (1) having been imported into cells, to a concentration of 10 µM, and the resultant was incubated at 37° C. for 30 minutes. Thereafter, the tube was centrifuged at 180 G for 10 minutes to remove the supernatant, and then, 1 mL of a HBSS buffer containing the FTC in a concentration of 10 µM was added thereto to suspend the cells, and the resultant was further incubated at 37° C. for 30 minutes.

Furthermore, each tube was centrifuged at 180 G for 10 minutes to remove the supernatant, the cells were suspended by adding the dye aqua for identifying dead cells thereto, and the resultant was incubated at 4° C. for 10 minutes. Thereafter, the tube was centrifuged at 180 G for 10 minutes to remove the supernatant, and then, the cells were suspended in a FACS buffer and analyzed by using a FACSCanto (trademark) II flow cytometry apparatus manufactured by BD.

The analysis was performed on a cell population showing a low signal for the aqua, so as to analyze a cell population from which dead cells were eliminated.

Comparative Example 3

Figure 7A:
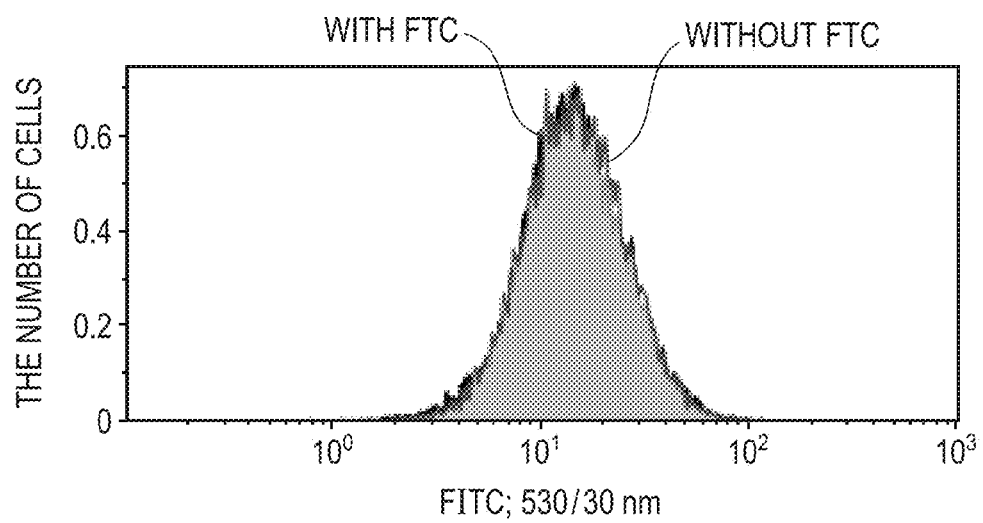
FIGS. 7A and 7B illustrate histograms observed in Example 57 and Comparative Example 3. The histogram illustrated in FIG. 7A is obtained from M1 macrophages stained with the compound (1), and the histogram illustrated in FIG. 7B is obtained from M2 macrophages stained with the compound (1).
Figure 7B:
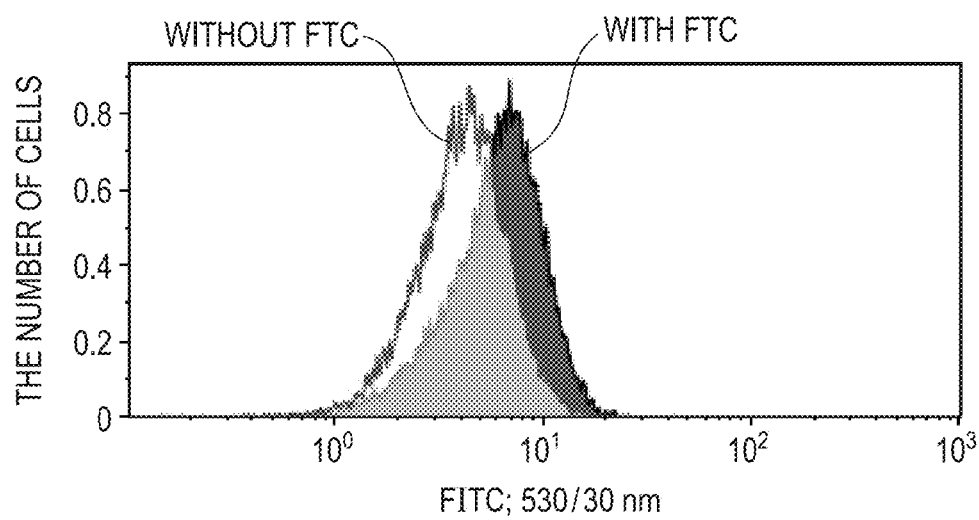

The analysis was performed in the same manner as in Example 57 except that the FTC was not added. As a result, as is obvious from FIGS. 7A and 7B, in a histogram in which the fluorescence intensity obtained in the FITC channel used for measuring a fluorescent signal derived from the compound (1) was plotted on the abscissa and the number of cells at each fluorescence intensity was plotted on the ordinate, the enhancement of the fluorescence intensity caused by the inhibition by the FTC of the export of the compound (1) from the cells was observed merely in the M2 macrophages. Thus, it was found that the influence of the export inhibition by the FTC is different depending on the subtypes.

Example 58

Two×$10^5$ each of M1 macrophages and M2 macrophages cultured in the same manner as in Example 1 were dispensed into a 1.5 mL tube, the compound (1) was added thereto to a concentration of 1 µM, and the resultant was incubated at 37° C. for 30 minutes. Thereafter, the tube was centrifuged at 180 G for 10 minutes to remove the supernatant, and then, a blocking treatment for cell surfaces was performed by using 2.4G2 (anti-mouse CD16/32 antibody, manufactured by Biolegend). To the cells having been subjected to the blocking treatment, a FACS buffer containing 0.2 µg of Pacific Blue-labeled anti-CD40 antibody and 0.1 µg of Alexa Fluor647-labeled anti-Dectin-1 antibody was added for performing immunofluorescent staining. The fluorescent labeling with these antibodies was selected so that the fluorescence wavelengths of the antibodies could overlap neither with each other nor with the fluorescence wavelengths of the compound (1) and the aqua.

Thereafter, each tube was centrifuged at 180 G for 10 minutes to remove the supernatant, the cells were suspended by adding the dye aqua for identifying dead cells, and the resultant was incubated at 4° C. for 10 minutes. Then, after the tube was centrifuged at 180 G for 10 minutes to remove the supernatant, the cells were suspended in a FACS buffer and analyzed by using the FACSCanto (trademark) II flow cytometry apparatus manufactured by BD. The analysis was performed on a cell population showing a low signal for the aqua, so as to analyze a cell population from which dead cells were eliminated.

As a result, in the M1 macrophages identified based on the strong staining with the compound (1), a fluorescent signal derived from the Pacific Blue-labeled anti-CD40 antibody was observed in a Pacific Blue channel (excited at 405 nm, 450/50 nm: center wavelength/wavelength width). On the contrary, in the M2 macrophages identified based on the weak staining with the compound (1), a fluorescent signal derived from the Alexa Fluor647-labeled anti-Dectin-1 antibody was observed in an APC channel (excited at 633 nm, 660/20 nm: center wavelength/wavelength width). It was found based on this result that the anti-CD40 antibody and the anti-Dectin-1 antibody are antibodies specifically binding respectively to the M1 macrophages and the M2 macrophages.

Identification of Macrophage Subtypes Differentiated from Mouse Cell Line by Using Macrophage Identification Agent Represented by General Formula (1)

Example 59

The subtypes were identified by using the compound (1) in the same manner as in Example 1 except that the macrophage subtypes differentiated from the mouse bone marrow cells were changed to macrophage subtypes differentiated from a cell line established from mouse monocytic leukemia.

<Culture of Subtypes>

The culture of subtypes was performed with reference to NPL 9. Specifically, RAW264.7 cells purchased from American Type Culture Collection, that is, a cell line established from mouse monocytic leukemia, were subcultured several times, and the resultant cells were dispersed to a concentration of 3.3×$10^4$/mL in a D-MEM containing 10% FBS, 1% P/S and 1% MEM-NEAA, and 3.3×$10^5$ cells were seeded in a 100 mm dish. The cells were grown by incubation performed in the presence of 5% $CO_2$ at 37° C. After 2 to 4 days, it was confirmed that an area of about to 70% of the bottom of the dish had been covered by the cells, the medium was then exchanged, and by adding 200 ng of interferon-γ and 1 µg of polyliposaccharide (both manufactured by Pepro Tech) to the medium, the cells were differentiated to the subtype M1. Besides, by adding 100 ng of IL-4, the cells were differentiated to the subtype M2. After incubation performed in the presence of 5% $CO_2$ at 37° C. for 24 hours, the resultant was rinsed with PBS, and PBS containing 0.25% trypsin and 1 mM EDTA was used for collecting, from the dish, the macrophages having been differentiated to the subtypes M1 and M2.

<Confirmation of Subtypes>

Figure 8:
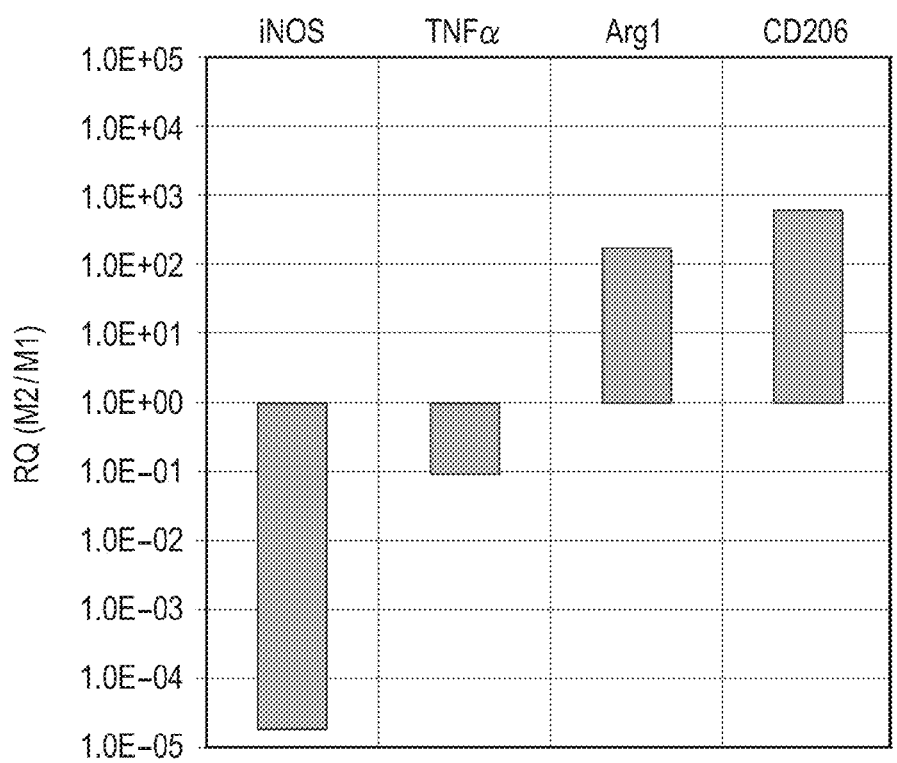
FIG. 8 illustrates a result of the gene expression analysis performed on M1 macrophage and M2 macrophage differentiated from RAW264.7 cells.

The thus collected M1 and M2 macrophages were subjected to the gene expression analysis performed in the same manner as in Example 1, resulting in confirming that the cells had been differentiated to the subtypes. The result is illustrated in FIG. 8. As is obvious from FIG. 8, the expression levels of the iNOS and the TNFα were higher in the cells differentiated to the M1 macrophages than in the cells differentiated to the M2 macrophages. On the other hand, the expression levels of the Arg1 and the CD206 were higher in the cells differentiated to the M2 macrophages than in the cells differentiated to the M1 macrophages. It was confirmed based on this result that the M1 macrophages and the M2 macrophages could be prepared by the differentiation.

After staining the M1 macrophages and the M2 macrophages differed from the RAW264.7 cells with the compound (1) in the same manner as in Example 1, a fluorescent signal derived from the compound (1) was analyzed in the same manner as in Example 1 except that dead cells were identified by using the TO-PRO-3. A histogram was prepared by plotting fluorescence intensity obtained in the FITC channel on the abscissa and plotting the number of cells at each fluorescence intensity on the ordinate, which is shown in FIG. 9.

Figure 9:
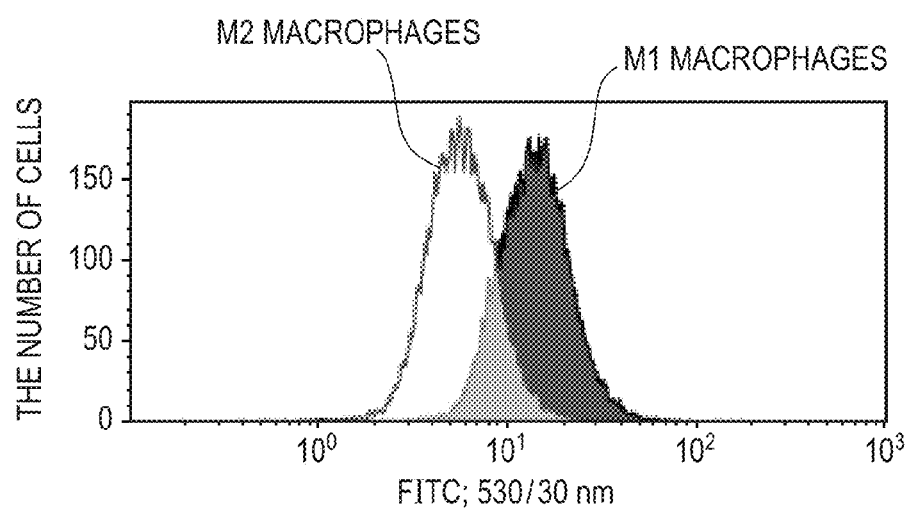
FIG. 9 illustrates a histogram observed in Example 59.

As a result, as is obvious from FIG. 9, the M1 macrophages were stained more strongly than the M2 macrophages by the compound (1), and it was thus found that these macrophages can be identified based on a difference in the fluorescence intensity.

in the presence of 5% $CO_2$ at 37° C. for 2 days with 500 ng of PMA added thereto. After exchanging the medium, by adding 200 ng of interferon-γ and 1 μg of polyliposaccharide (both manufactured by Pepro Tech) to the medium, the cells were differentiated to the subtype M1. Besides, by adding 200 ng of IL-4 and IL-13, the cells were differentiated to the subtype M2. After incubation performed in the presence of 5% $CO_2$ at 37° C. for 24 hours, the resultant was rinsed with PBS, and PBS containing 0.25% trypsin and 1 mM EDTA (ethylenediaminetetraacetic acid) was used for collecting, from the dish, the macrophages having been differentiated to the subtypes M1 and M2.

Figure 10:
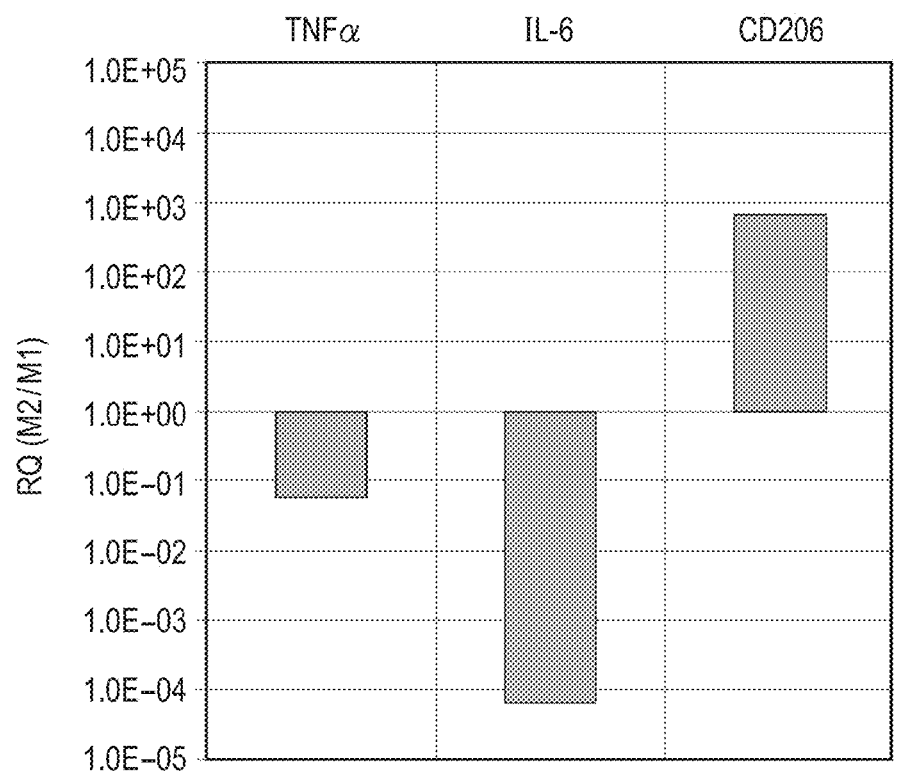
FIG. 10 illustrates a result of the gene expression analysis performed on M1 macrophage and M2 macrophage differentiated from THP-1 cells.

Through the gene expression analysis performed in the same manner as in Example 1 by using primers shown in Table 5, the collected M1 macrophages and M2 macrophages were confirmed to have been differentiated to the subtypes. The result is illustrated in FIG. 10. As is obvious from FIG. 10, the expression levels of the TNFα and IL-6 were higher in the cells differentiated to the M1 macrophages than in the cells differentiated to the M2 macrophages. On the other hand, the expression level of the CD206 was higher in the cells differentiated to the M2 macrophages than in the cells differentiated to the M1 macrophages. It was confirmed based on this result that the M1 macrophages and the M2 macrophages could be prepared by the differentiation.

TABLE 5

| Target gene | Sequence of primer | | Remarks |
| --- | --- | --- | --- |
| | Forward | Reverse | |
| GAPDH | CAACAGCGACACCCACTCCT | CACCCTGTTGCTGTAGCCAAA | Endogenous control gene |
| TNFα | TGCACTTTGGAGTGATCGGC | CTCAGCTTGAGGGTTTGCTAC | M1 macrophage marker |
| IL-6 | AGCCACTCACCTCTTCAGAAC | GCCTCTTTGCTGCTTTCACAC | M1 macrophage marker |
| CD206 | CCCTCAGAAAGTGATGTGCCTA | TACTTGTGAGGTCACCGCCT | M2 macrophage marker |

Identification of Macrophage Subtypes Differentiated from Human Cell Line by Using Macrophage Identification Agent Represented by General Formula (1)

Examples 60 to 64

The subtypes were identified by using the compound (1) in the same manner as in Example 1 except that the macrophage subtypes differentiated from the mouse bone marrow cells were changed to macrophage subtypes differentiated from a cell line established from human acute monocytic leukemia.
<Culture of Subtypes>
The culture of subtypes was performed with reference to NPL 10. Specifically, THP-1 cells purchased from JCRB Cell Bank of National Institute of Biomedical Innovation, that is, a cell line established from human acute monocytic leukemia, were subcultured several times, and the resultant cells were dispersed to a concentration of $5.0 \times 10^5$/mL in an RPMI1640 containing 10% FBS and 1% P/S, and $5.0 \times 10^6$ cells were seeded in a 100 mm dish. The monocytes were differentiated into macrophages by incubating the resultant After staining the M1 macrophages and the M2 macrophages differentiated from the THP-1 cells with the compounds (1)(3)(4)(12) and (15) in the same manner as in Example 1, fluorescent signals derived from the compounds (1) (3) (4) (12) and (15) were analyzed in the same manner as in Example 1 except that dead cells were identified by using the TO-PRO-3. Specifically, fluorescent signals derived from the compounds (1) (3) (4) (12) and (15) were measured by using the channels which are appropriate for each of the compounds and the identification abilities for the subtypes of the compounds were evaluated based on the values of the resolution R.

Comparative Example 4

After staining the M1 macrophages and the M2 macrophages differentiated from the THP-1 cells with the compound (1) in the same manner as in Example 1, dead cells were identified by using the TO-PRO-3, and fluorescent signal derived from the compound (1) was analyzed in the same manner as in Example 1 except that the fluorescent signal derived from the comparative compound (2) was measured using the PE-Cy7 channel (excited at 488 nm, 780/60 nm: center wavelength/wavelength width). The identification abilities for the subtypes of the compounds were evaluated based on the values of the resolution R.

Comparative Example 5

After staining the M1 macrophages and the M2 macrophages differentiated from the THP-1 cells with the compound (2) in the same manner as in Example 1, dead cells were identified by using the TO-PRO-3, and fluorescent signal derived from the compound (2) was analyzed in the same manner as in Example 1. The identification abilities for the subtypes of the compounds were evaluated based on the values of the resolution R.

The results obtained in Examples 60 to 64 and Comparative Examples 4 and 5 described above are shown in Table 6. The details of channels shown in Table 6 are shown in Table 3.

TABLE 6

| Example | Compound | Channel | Peak position of M1 macrophage | Peak position of M2 macrophage | Resolution ratio R | Evaluation of macrophage subtype identification | Selectivity |
|---|---|---|---|---|---|---|---|
| Example 60 | (1) | FITC | 58.1 | 33.4 | 0.409 | B | M1 |
| Example 61 | (3) | PE | 9.63 | 12.3 | 0.257 | B | M2 |
| Example 62 | (4) | FITC | 26.5 | 17.9 | 0.372 | B | M1 |
| Example 63 | (12) | PE | 37.4 | 46.5 | 0.276 | B | M2 |
| Example 64 | (15) | PE | 5.62 | 7.4 | 0.216 | B | M2 |
| Comparative Example 4 | Comparative compound (4) | PE-Cy7 | 0.24 | 0.21 | 0.021 | C | No selectivity |
| Comparative Example 5 | Comparative compound (5) | FITC | 0.25 | 0.21 | 0.061 | C | No selectivity |

As is obvious from Table 6, when using the M1 macrophages and the M2 macrophages differentiated from the THP-1 cell, there was no difference in the staining intensity between the M1 macrophages and the M2 macrophages stained by using the comparative compound (1) or (2) and hence these macrophages cannot be identified. On the other hand when the macrophage identification agent containing the dye compound represented by general formula (1) of the present invention is used, the M1 macrophages and the M2 macrophages could be identified from each other based on a difference in the fluorescence intensity.

It is understood from Examples 57 and 58 that the macrophage identification agent represented by general formula (1) of the present invention can be used for analyzing the correlation between a subtype and a substance.

It is understood from Examples 1 to 58 and Comparative Examples 1 and 2 described above that the macrophage identification agent represented by general formula (1) of the present invention can be used for identifying, sorting, evaluating and analyzing a subtype.

Besides, by performing operations similar to those of Examples 57 and 58 on a plurality of substances, the correlation between a subtype and the substances can be screened by using the macrophage identification agent represented by general formula (1) of the present invention.

Besides, it was revealed based on Example 59 that not only the subtypes differentiated from bone marrow cells but also the subtypes differentiated from a mouse cell line can be identified by using the macrophage identification agent represented by general formula (1) of the present invention.

This result supports that subtypes can be identified by using the macrophage identification agent represented by general formula (1) of the present invention even if the cell type is different.

Besides, it was revealed based on Examples 60 to 64 and comparative examples 4 and 5 that not only the subtypes differentiated from bone marrow cells but also the subtypes differentiated from a human cell line can be identified by using the macrophage identification agent represented by general formula (1) of the present invention. This result further supports that subtypes can be identified by using the macrophage identification agent represented by general formula (1) of the present invention even if human-derived cells are used, and probably suggests that the present invention is applicable to pathologic tissues like human tissues or even a human individual.

Synthetic Example 2

As an example of the macrophage identification agent represented by general formula (6) of the present invention, a synthetic example of the compound (86) will be described.

Compound (A1)

Compound (B2)

Compound (86)

Under a nitrogen atmosphere, 0.22 g (1.0 mmol) of a compound (B2) and 0.16 g (2.0 mmol) of anhydrous sodium acetate were added to a 10 mL acetic anhydride solution of 0.61 g (2.0 mmol) of a compound (A1), and the resulting solution was stirred at 100° C. for 1 hour. After completing the reaction, 100 mL of a saturated saline was slowly added dropwise thereto while cooling, and the resulting solution was cooled to room temperature. The resultant solution was extracted with 50 mL of dichloromethane twice. After drying the resultant over anhydrous sodium sulfate, an organic layer was concentrated under reduced pressure. The residue was purified by silica gel chromatography and recrystallized from diethyl ether, thereby obtaining 0.29 g (yield: 59%) of the compound (86). The obtained substance was confirmed to be the compound of interest by the $^1$H nuclear magnetic resonance spectrometric analysis (ECA-400, manufactured by JEOL Ltd.) and the LC/TOF MS (LC/MSD TOF, manufactured by Agilent Technologies, Inc.).

Synthetic Example 3

As an example of the macrophage identification agent represented by general formula (6) of the present invention, a synthetic example of the compound (110) will be described.

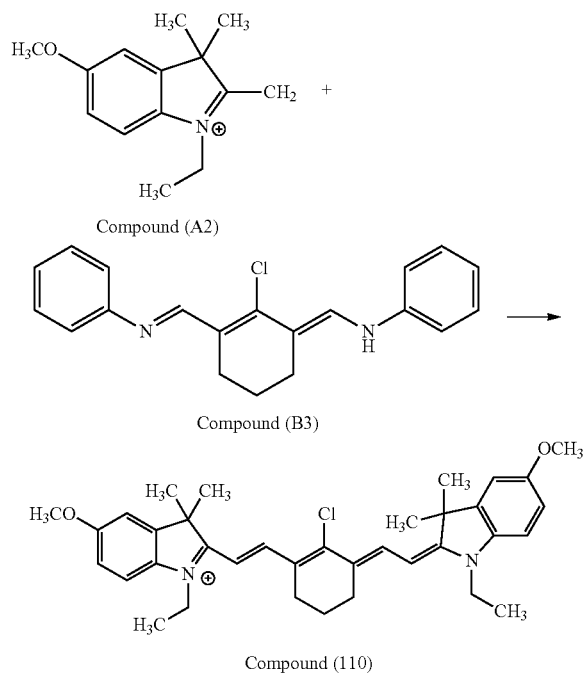

Under a nitrogen atmosphere, 0.32 g (1.0 mmol) of a compound (B3) and 0.25 g (3.0 mmol) of anhydrous sodium acetate were added to a 10 mL acetic anhydride solution of 0.48 g (2.2 mmol) of a compound (A2), and the resulting solution was stirred at 100° C. for 1 hour. After completing the reaction, 100 mL of a saturated saline was slowly added dropwise thereto while cooling, and the resulting solution was cooled to room temperature. The resultant solution was extracted with 50 mL of dichloromethane twice. After drying the resultant over anhydrous sodium sulfate, an organic layer was concentrated under reduced pressure. The residue was purified by the silica gel chromatography and recrystallized from diethyl ether, thereby obtaining 0.38 g (yield: 54%) of the compound (110). The obtained substance was confirmed to be the compound (110) of interest by the $^1$H nuclear magnetic resonance spectrometric analysis (ECA-400, manufactured by JEOL Ltd.) and the LC/TOF MS (LC/MSD TOF, manufactured by Agilent Technologies, Inc.).

<Other Compounds Represented by General Formula (6)>

In the same manner as in Synthetic Examples 2 and 3, compounds shown in Table 7 were synthesized and identified as the compounds of interest.

Subtype Identification by Using Macrophage Identification Agent Represented by General Formula (6)

Example 65

Figure 11:
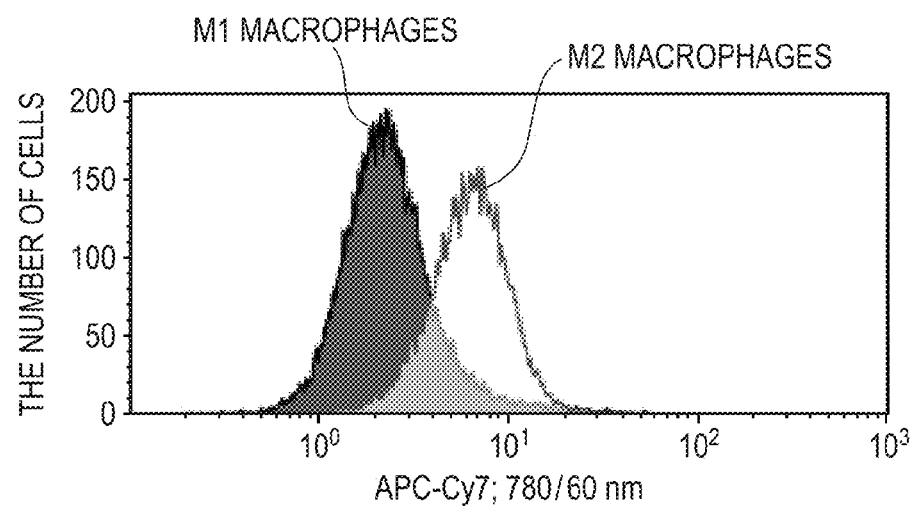
FIG. 11 illustrates a histogram observed in Example 65.

A fluorescent signal derived from the compound (86) was analyzed in the same manner as in Example 1 except that the compound (1) used in Example 1 was replaced with the compound (86). However, the signal of the compound (86) was measured in an APC-Cy7 channel (excited at 633 nm, in a fluorescence wavelength measurement region of 780/60 nm of center wavelength/wavelength width). A histogram was prepared by plotting fluorescence intensity obtained in the APC-Cy7 channel on the abscissa and plotting the number of cells at each fluorescence intensity on the ordinate, which is shown in FIG. 11.

Examples 66 to 76

Fluorescent signals derived from the compounds (88), (90), (91), (92), (95), (98), (99), (100), (103), (104) and (113) were analyzed in the same manner as in Example 1 except that the compound (1) used in Example 1 was replaced with the compounds (88), (90), (91), (92), (95), (98), (99), (100), (103), (104) and (113).

Comparative Example 6

Figure 12:
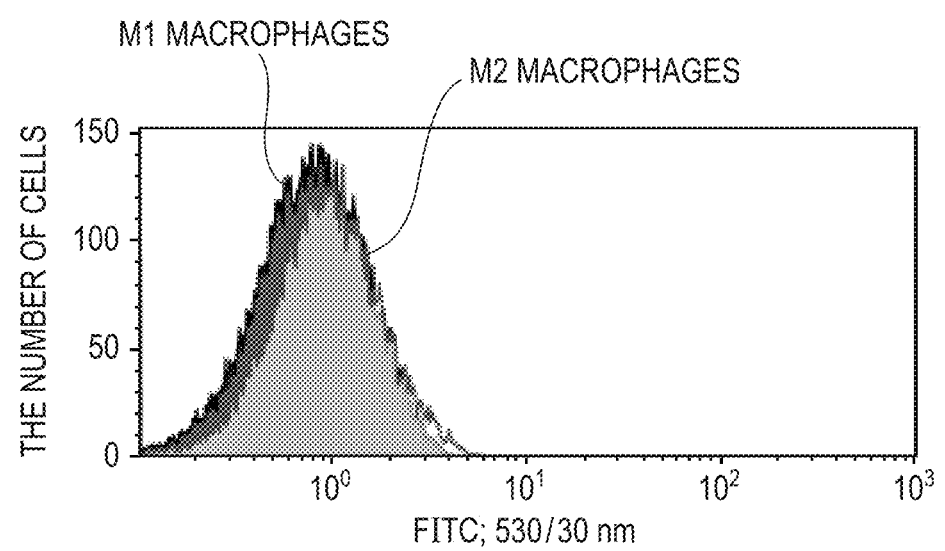
FIG. 12 illustrates a histogram observed in Comparative Example 6.

A fluorescent signal derived from a comparative compound (3) was analyzed in the same manner as in Example 1 except that the compound (1) used in Example 1 was replaced with the comparative compound (3). However, the fluorescent signal of the comparative compound (3) was measured in the FITC channel (excited at 488 nm, 530/30 nm: center wavelength/wavelength width). A histogram was prepared by plotting fluorescence intensity obtained in the FITC channel on the abscissa and plotting the number of cells at each fluorescence intensity on the ordinate, which is shown in FIG. 12.

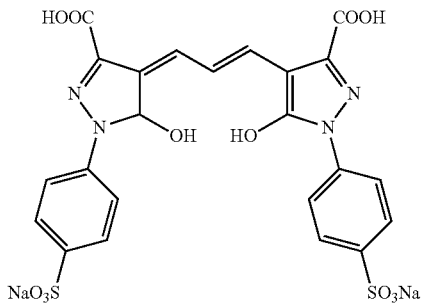

Comparative Compound (3)

The results obtained in Examples 65 to 76 and Comparative Examples 1 and 6 described above are shown in Table 7.

<Evaluation Method for Identification Ability of Macrophage Identification Agent Represented by General Formula (6)>

Fluorescent signals derived from the compounds (88), (90), (91), (92), (95), (98), (99), (100), (103), (104) and (113) and the comparative compound (3) were measured in channels suitable to the respective compounds in the same manner as in the evaluation method for the identification ability of the macrophage identification agent represented by general formula (1) except that the compounds (3), (4), (6), (7), (9), (11) to (13), (15), (17), (19) to (26), (28), (30) to (33), (35), (36), (38), (42) to (45), (48) to (62), (65), (67), (74) to (76), (82), (83) and (85) and the comparative compounds (1) and (2) used in the evaluation method for the identification ability of the macrophage identification agent represented by general formula (1) were replaced with the compounds (88), (90), (91), (92), (95), (98), (99), (100), (103), (104) and (113). By using a resolution R thus obtained as an index, the identification ability for a subtype of each compound was evaluated.

The evaluation results are shown in Table 7. The details of channels shown in Table 7 are shown in Table 3.

As a result, when the compound (103) is used for staining, the M2 macrophage shows a higher fluorescence intensity in the PE-Cy7 channel than the M1 macrophage, and on the contrary, when the compound (113) is used for staining, the M2 macrophage shows a higher fluorescence intensity in the APC-Cy7 channel than the M1 macrophage. Therefore, on the cytogram developed with respect to the intensity of the fluorescent signal obtained in the PE-Cy7 channel and the intensity of the fluorescent signal obtained in the APC-Cy7 channel, the M1 macrophages and the M2 macrophages stained with the compound (103) and the compound (113) are plotted as cell populations having different fluorescent characteristics, and hence, these macrophages can be identified.

TABLE 7

| Example | Compound | Channel | Peak position of M1 macrophage | Peak position of M2 macrophage | Resolution ratio R | Evaluation of macrophage subtype identification | Selectivity |
|---|---|---|---|---|---|---|---|
| Example 65 | (86) | APC-Cy7 | 2.27 | 6.37 | 0.602 | A | M2 |
| Example 66 | (88) | APC-Cy7 | 0.95 | 1.48 | 0.241 | B | M2 |
| Example 67 | (90) | APC-Cy7 | 0.86 | 1.31 | 0.321 | B | M2 |
| Example 68 | (91) | APC-Cy7 | 2.96 | 13.89 | 0.476 | B | M2 |
| Example 69 | (92) | PE-Cy7 | 2.27 | 3.9 | 0.534 | A | M2 |
| Example 70 | (95) | PE | 71.57 | 133.45 | 0.421 | B | M2 |
| Example 71 | (98) | FITC | 21.95 | 61.59 | 0.507 | A | M2 |
| Example 72 | (99) | PE | 191.14 | 331.51 | 0.673 | A | M2 |
| Example 73 | (100) | PE | 16.41 | 32.87 | 0.372 | B | M2 |
| Example 74 | (103) | PE-Cy7 | 2.97 | 8.23 | 0.597 | A | M2 |
| Example 75 | (104) | PE-Cy7 | 95.26 | 197.19 | 0.698 | A | M2 |
| Example 76 | (113) | APC-Cy-7 | 9.05 | 21.39 | 0.857 | A | M2 |
| Comparative Example 1 | Comparative compound (1) | PE-Cy7 | 1.70 | 1.86 | 0.006 | C | No selectivity |
| Comparative Example 6 | Comparative compound (3) | FITC | 0.86 | 0.97 | 0.079 | C | No selectivity |

As is obvious from Table 7, FIG. 1 and FIGS. 11 and 12, although there is no difference in the staining intensity between the M1 macrophages and the M2 macrophages stained by using the comparative compound (1) or (3) and hence these macrophages cannot be identified, if the macrophage identification agent containing the dye compound represented by general formula (6) of the present invention is used, the M1 macrophages and the M2 macrophages can be identified from each other based on a difference in the fluorescence intensity.

Example 77

Two×$10^5$ each of M1 macrophages and M2 macrophages cultured in the same manner as in Example 1 were dispensed into a 1.5 mL tube, and the compound (103) and the compound (113) were added thereto each to a concentration of 1 µM.

A fluorescent signal derived from the compound (103) was measured in the PE-Cy7 channel (excited at 488 nm, 780/60 nm: center wavelength/wavelength width) and a fluorescent signal derived from the compound (113) was measured in the APC-Cy7 channel (excited at 633 nm, 780/60 nm: center wavelength/wavelength width). A cytogram developed by plotting the intensity of the fluorescent signal derived from the compound (103) and obtained in the PE-Cy7 channel on the ordinate and plotting the intensity of the fluorescent signal derived from the compound (113) and obtained in the APC-Cy7 channel on the abscissa was prepared.

The operation was performed in the same manner as in Example 1 except for the above.

This example reveals that a subtype can be identified even when two or more types of compounds for the macrophage identification agent represented by general formula (6) of the present invention are used in combination.

Examples 65 to 77 and Comparative Examples 1 and 6 described above reveal that a subtype contained in a biological sample can be identified by using one or more macrophage identification agents represented by general formula (6) of the present invention.

Sorting of Subtype by Using Macrophage Identification Agent Represented by General Formula (6)

Example 78

One×$10^5$ each of M1 macrophages and M2 macrophages cultured in the same manner as in Example 1 were mixed in a 1.5 mL tube, and the compound (86) was added thereto to a concentration of 1 µM.

The operation was performed in the same manner as in Example 1 except for the above.

Figure 13A:
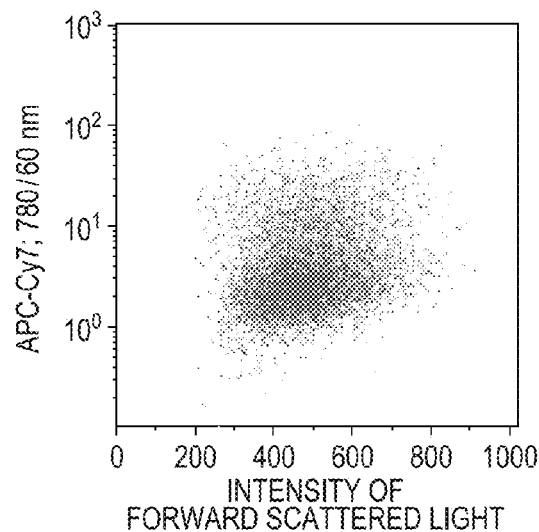
FIGS. 13A, 13B and 13C illustrate cytograms observed in Example 78. The cytogram illustrated in FIG. 13A is obtained from M1 macrophages stained with a compound (86), the cytogram illustrated in FIG. 13B is obtained from M2 macrophages stained with the compound (86), and the cytogram illustrated in FIG. 13C is obtained from a sample of a mixture of the M1 macrophages and the M2 macrophages stained with the compound (86).
Figure 13B:
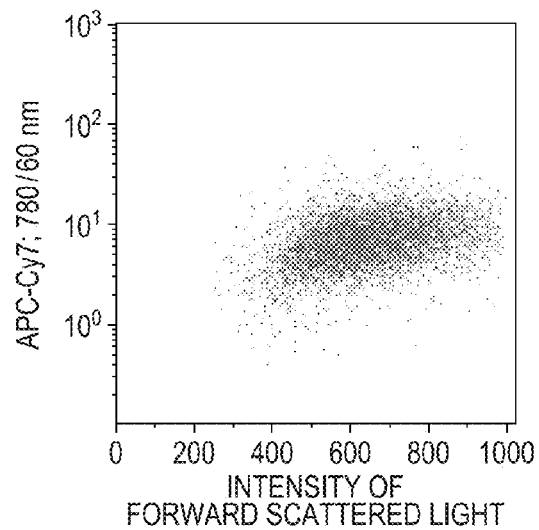
Figure 13C:
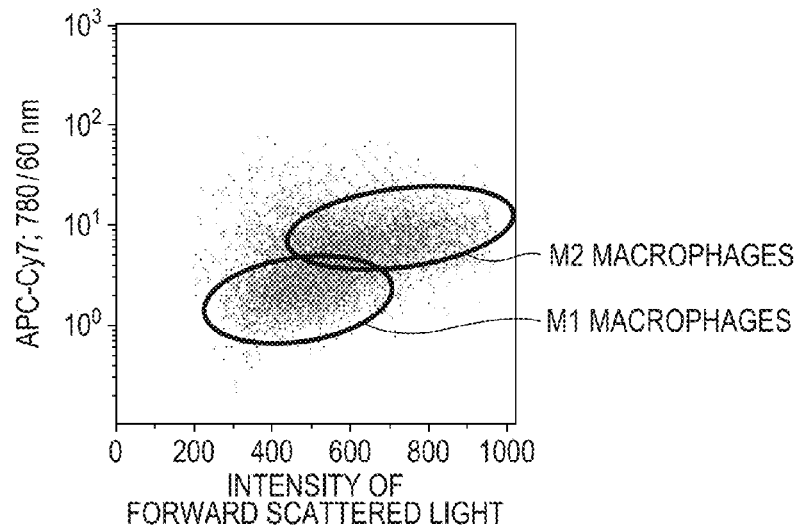

As a result, as illustrated in FIGS. 13A to 13C, the M1 macrophages and the M2 macrophages stained with the compound (86) were plotted, on a cytogram developed with respect to the intensity of forward scattered light affected by the size of cells and the intensity of a fluorescent signal derived from the compound (86), as cell populations having different fluorescence intensity distributions. Since the compound (86) having a characteristic to stain the M2 macrophages more strongly than the M1 macrophages was used for staining, the M2 macrophages can be identified as a cell population having a high fluorescence intensity derived from the compound (86), and on the other hand, the M1 macrophages can be identified as a cell population having a low fluorescence intensity derived from the compound (86). Besides, the M1 macrophages and the M2 macrophages identified by using the compound (86) could be each sorted with an FACS apparatus. The sorted subtypes were confirmed by the fluorescent antibody method and the gene expression analysis.

It was found through Examples 65 to 78 described above that a subtype can be identified and sorted by using the macrophage identification agent represented by general formula (6) of the present invention.

Analysis and Screening of Subtype by Using Macrophage Identification Agent Represented by General Formula (6)

Example 79

Two×10$^5$ each of M1 macrophages and M2 macrophages cultured in the same manner as in Example 1 were dispensed into a 1.5 mL tube, and the compound (113) was added thereto to a concentration of 1 µM, and furthermore, MK-571 (manufactured by Sigma-Aldrich) was added thereto, as a substance for inhibiting export of the compound (113) having been imported into cells, to a concentration of 10 uM, and the resultant was incubated at 37° C. for 30 minutes. Thereafter, the tube was centrifuged at 180 G for 10 minutes to remove the supernatant, and then, 1 mL of a HBSS buffer containing the MK-571 in a concentration of 10 µM was added thereto to suspend the cells, and the resultant was further incubated at 37° C. for 30 minutes.

The operation was performed in the same manner as in Example 57 except for the above.

Comparative Example 7

Figure 14A:
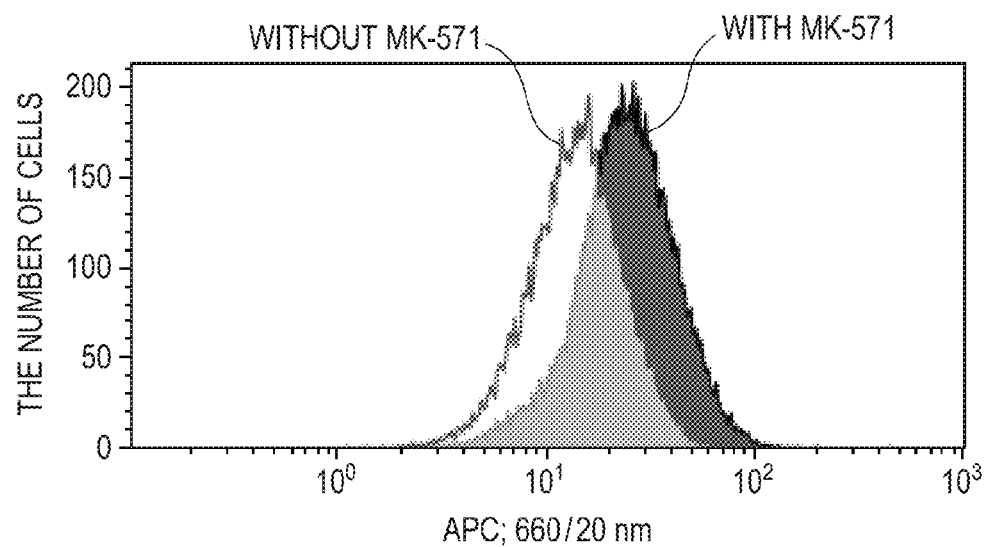
FIGS. 14A and 14B illustrate histograms observed in Example 79 and Comparative Example 5. The cytogram illustrated in FIG. 14A is obtained from M1 macrophages stained with a compound (113), and the cytogram illustrated in FIG. 14B is obtained from M2 macrophages stained with the compound (113).
Figure 14B:
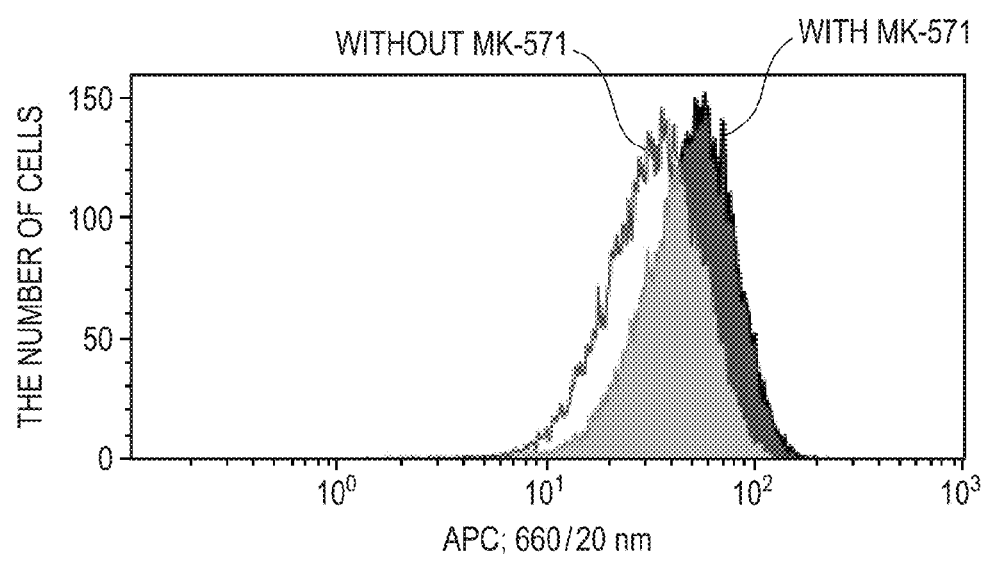

The analysis was performed in the same manner as in Example 79 except that the MK-571 was not added. As a result, as is obvious from FIGS. 14A and 14B, in a histogram in which the fluorescence intensity obtained in the FITC channel for measuring a fluorescent signal derived from the compound (113) was plotted on the abscissa and the number of cells at each fluorescence intensity was plotted on the ordinate, the enhancement of the fluorescence intensity caused by the inhibition by the MK-571 of the export of the compound (113) from the cells was observed in both the M1 macrophages and the M2 macrophages. The degree of the enhancement of the peak intensity caused by adding the MK-571 was evaluated by calculating the resolution R described above by using peak intensities in histograms prepared with and without adding the MK-571. As a result, the degree was 0.406 in the M1 macrophages and 0.438 in the M2 macrophages. Thus, it was found that the influence on the export inhibition by the MK-571 is slightly different depending on the subtypes.

Example 80

Two×10$^5$ each of M1 macrophages and M2 macrophages cultured in the same manner as in Example 1 were dispensed into a 1.5 mL tube, the compound (86) was added thereto to a concentration of 1 uM, and the resultant was incubated at 37° C. for 30 minutes. Thereafter, the tube was centrifuged at 180 G for 10 minutes to remove the supernatant, and then, a blocking treatment for cell surfaces was performed by using 2.4G2 (anti-mouse CD16/32 antibody, manufactured by Biolegend). To the cells having been subjected to the blocking treatment, a FACS buffer containing 0.2 µg of Alexa Fluor647-labeled anti-CD40 antibody and 0.2 µg of PE-labeled anti-Dectin-1 antibody was added for performing the immunofluorescent staining. The fluorescent labeling with these antibodies was selected so that the fluorescence wavelengths of the antibodies could overlap neither with each other nor with the fluorescence wavelengths of the compound (86) and the aqua.

The operation was performed in the same manner as in Example 58 except for the above.

As a result, in the M2 macrophages identified based on the strong staining with the compound (86), a fluorescent signal derived from the PE-labeled anti-Dectin-1 antibody was observed in a PE channel (excited at 488 nm, 585/42 nm: center wavelength/wavelength width). On the contrary, in the M1 macrophages identified based on the weak staining with the compound (86), a fluorescent signal derived from the Alexa Fluor647-labeled anti-CD40 antibody was observed in the APC channel (excited at 633 nm, 660/20 nm: center wavelength/wavelength width). It was found based on this result that the anti-Dectin-1 antibody and the anti-CD40 antibody are antibodies respectively specifically binding to the M2 macrophages and the M1 macrophages.

It is understood from Examples 79 and 80 that the macrophage identification agent represented by general formula (6) of the present invention can be used for analyzing the correlation between a subtype and a substance.

It is understood from Examples 65 to 80 and Comparative Examples 1 and 6 described above that the macrophage identification agent of the present invention can be used for identifying, sorting, evaluating and analyzing a subtype.

Besides, by performing operations similar to those of Examples 79 and 80 on a plurality of substances, the correlation between a subtype and the substances can be screened by using the macrophage identification agent of the present invention.

Synthetic Example 4

As an example of the macrophage identification agent represented by general formula (10) of the present invention, a synthetic example of the compound (116) will be described.

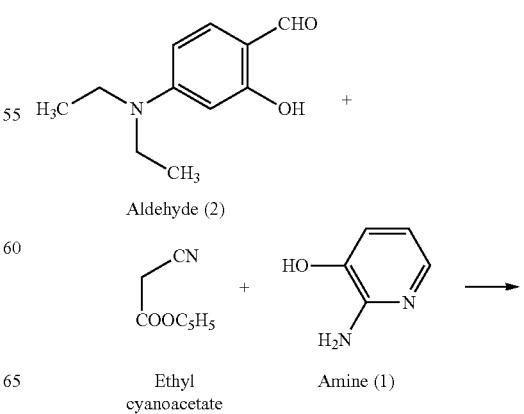

Aldehyde (2)

Ethyl cyanoacetate

Amine (1)

-continued

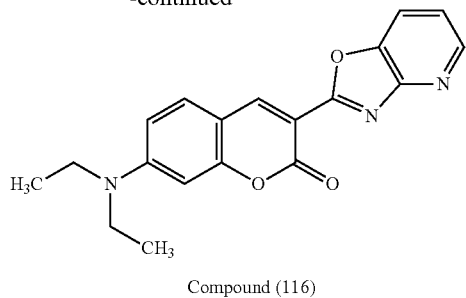

Compound (116)

To a 200 mL n-butyl alcohol solution of 5.5 g (50 mmol) of amine (1), 12.1 g (62.5 mmol) of aldehyde (2), 6.7 mL (62.5 mmol) of ethyl cyanoacetate and 1.4 g (12.5 mmol) of benzoic acid were added, and the resulting solution was heated to reflux at 150° C. for 11 hours. After completing the reaction, the resulting solution was cooled to room temperature, and the solvent was distilled off under reduced pressure. To the residue, 100 mL of isopropyl alcohol and 15 mL of a 1 mol/L sodium hydroxide aqueous solution were added, followed by stirring. The thus obtained solid was filtered out and washed with 100 mL of isopropyl alcohol and 66 mL of DMSO, thereby obtaining 7.8 g (23 mmol, yield: 47%) of the compound (116) of interest.

Synthetic Example 5

As an example of the macrophage identification agent represented by general formula (10) of the present invention, a synthetic example of the compound (135) will be described.

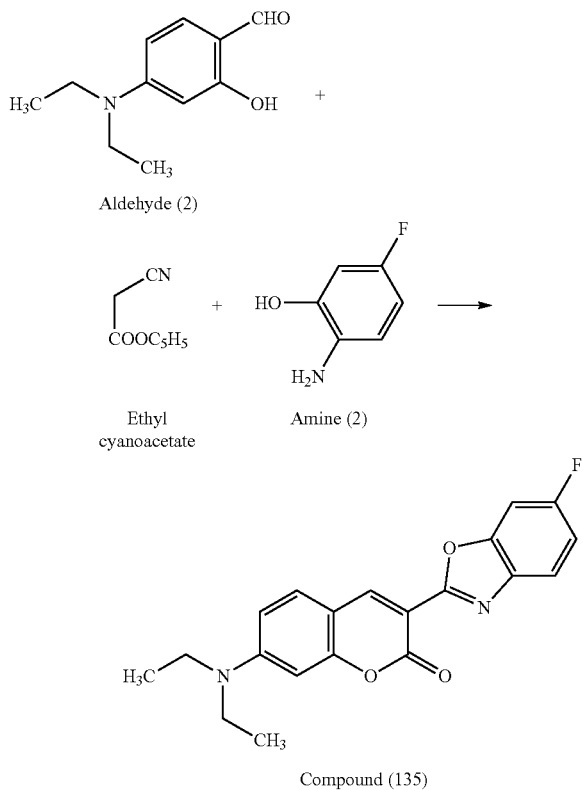

The operation was performed in the same manner as in Synthetic Example 4 except that amine (2) was used in Synthetic Example 5 instead of the amine (1), thereby obtaining 8.46 g (24 mmol, yield: 48%) of the compound (135) of interest.

Subtype Identification by Using Macrophage Identification Agent Represented by General Formula (10)

Example 81

Figure 15:
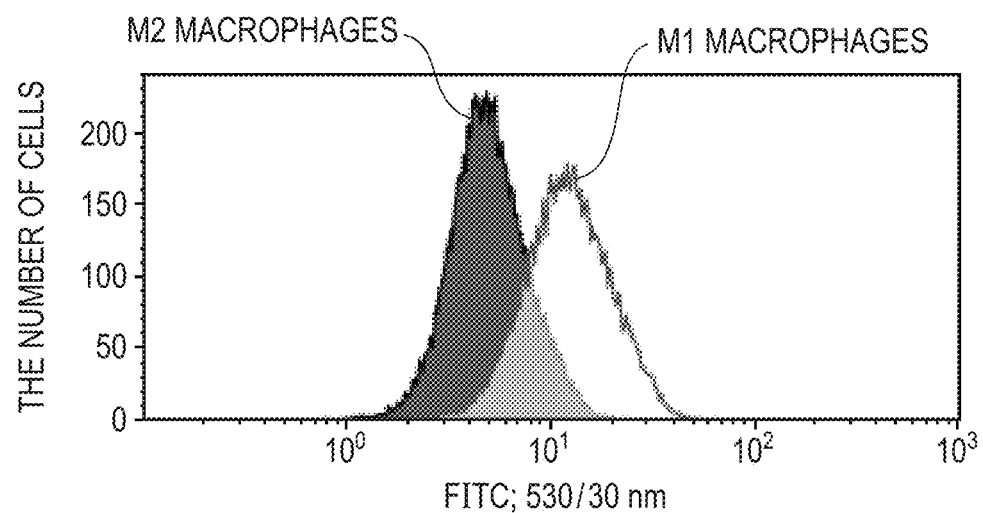
FIG. 15 illustrates a histogram observed in Example 81.

A fluorescent signal derived from the compound (116) was analyzed in the same manner as in Example 1 except that the compound (1) used in Example 1 was replaced with the compound (116) and the TO-PRO-3 was used for identifying dead cells. A histogram was prepared by plotting fluorescence intensity obtained in the FITC channel on the abscissa and plotting the number of cells at each fluorescence intensity on the ordinate, which is shown in FIG. 15.

Examples 82 to 90

Fluorescent signals derived from the compounds (117), (119), (120), (122), (127), (129), (131), (132) and (138) were analyzed in the same manner as in Example 1 except that the compound (1) used in Example 1 was replaced with the compounds (117), (119), (120), (122), (127), (129), (131), (132) and (138).

Comparative Example 8

Figure 16:
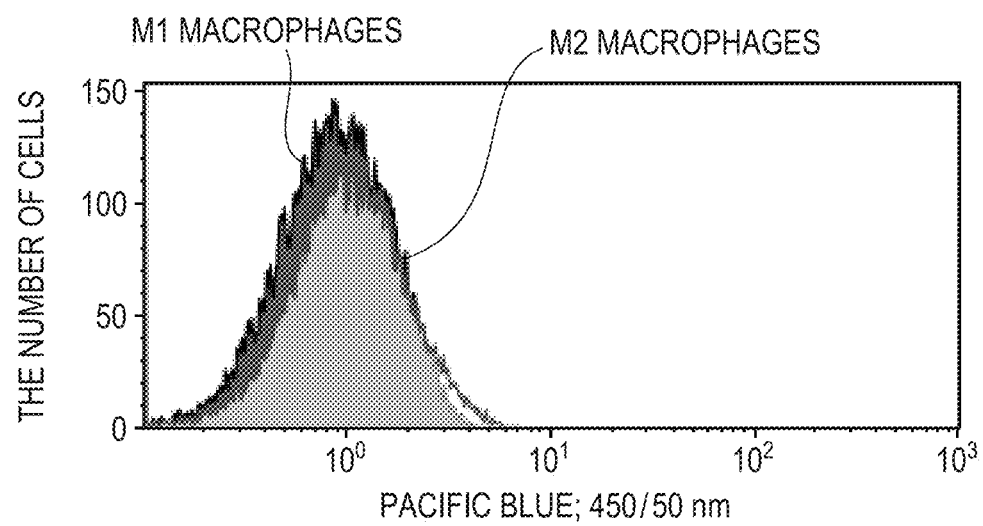
FIG. 16 illustrates a histogram observed in Comparative Example 8.
Figure 17A:
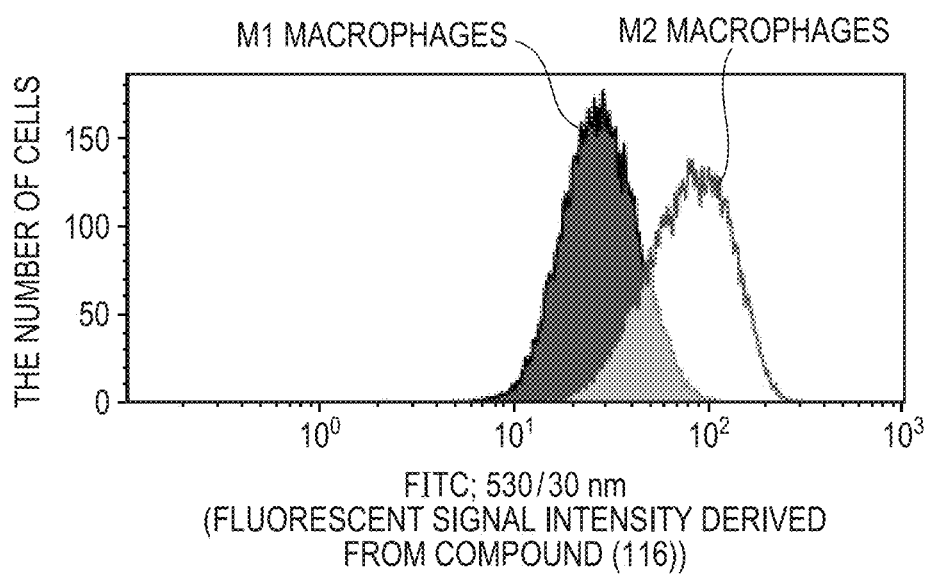
FIGS. 17A, 17B, 17C, 17D and 17E illustrate histograms (FIGS. 17A and 17B) and cytograms (FIGS. 17C, 17D and 17E) observed in Example 91. The cytogram illustrated in FIG. 17C is obtained from M1 macrophages stained with a compound (116) and a compound (120). The cytogram illustrated in FIG. 17D is obtained from M2 macrophages stained with the compound (116) and the compound (120). The cytogram illustrated in FIG. 17E is obtained by overlapping the cytograms illustrated in FIGS. 17C and 17D.
Figure 17B:
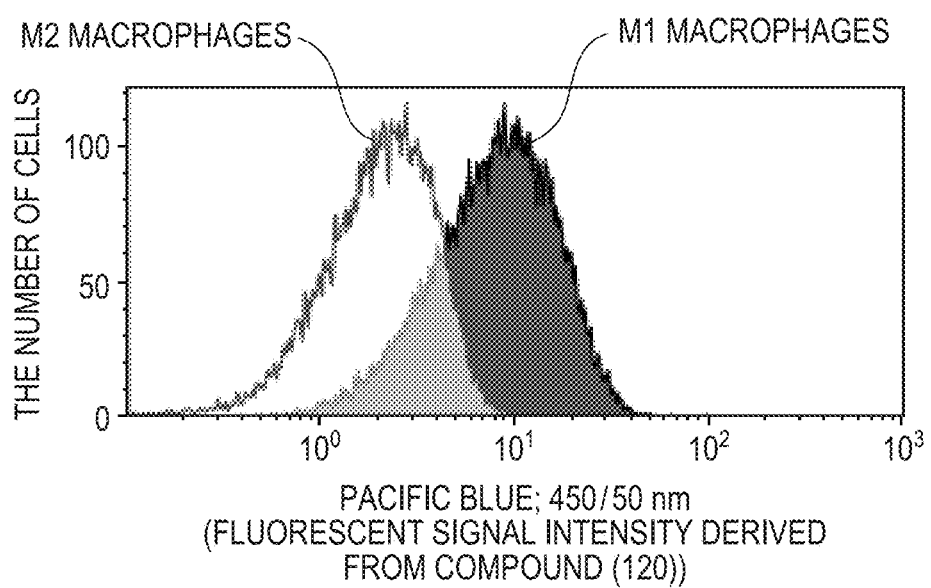
Figure 17C:
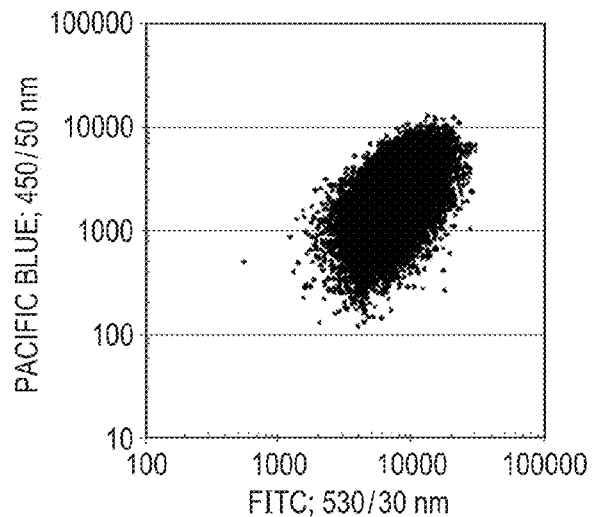
Figure 17D:
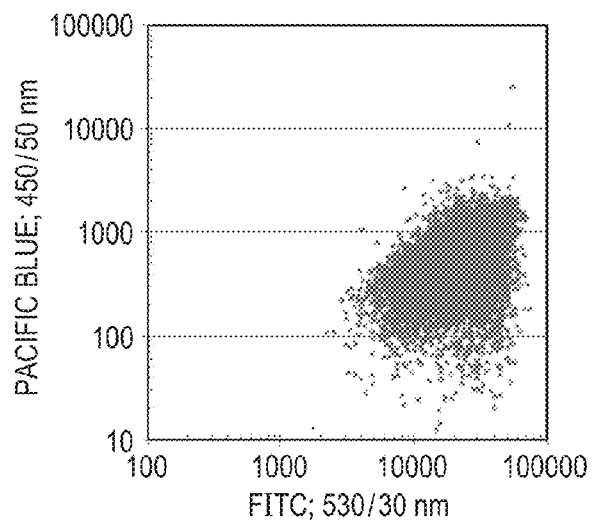
Figure 17E:
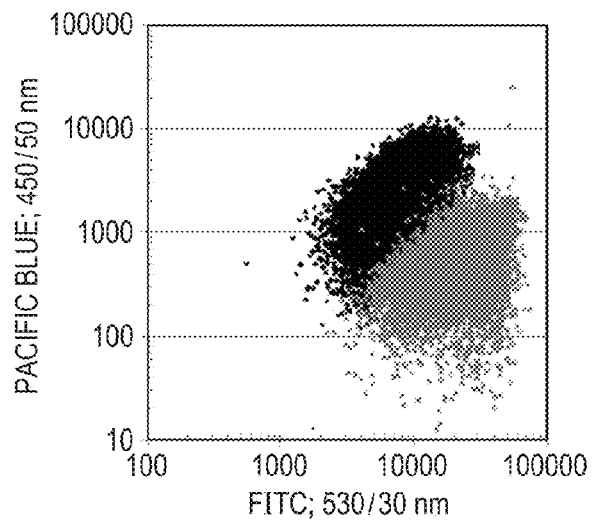

A fluorescent signal derived from a comparative compound (4) was analyzed in the same manner as in Example 1 except that the compound (1) used in Example 1 was replaced with the comparative compound (4). A histogram was prepared by plotting fluorescence intensity obtained in the Pacific Blue channel on the abscissa and plotting the number of cells at each fluorescence intensity on the ordinate, which is shown in FIG. 16.

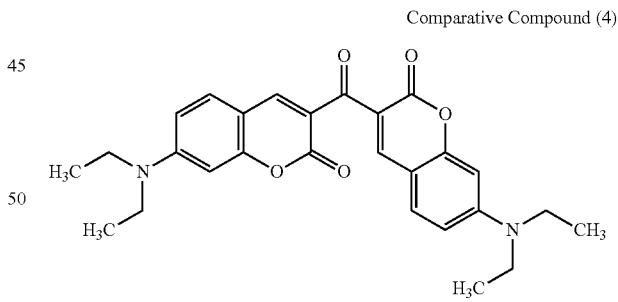

Comparative Compound (4)

The results obtained in Examples 81 to 90 and Comparative Examples 1 and 8 described above are shown in Table 8.

<Evaluation Method for Identification Ability of Macrophage Identification Agent Represented by General Formula (10)>

Fluorescent signals derived from the compounds (117), (119), (120), (122), (127), (129), (131), (132) and (138) and the comparative compound (4) were measured in channels suitable to the respective compounds in the same manner as in the evaluation method for the identification ability of the macrophage identification agent represented by general formula (1) except that the compounds (3), (4), (6), (7), (9), (11) to (13), (15), (17), (19) to (26), (28), (30) to (33), (35), (36), (38), (42) to (45), (48) to (62), (65), (67), (74) to (76), (82), (83) and (85) and the comparative compounds (1) and (2) used in the evaluation method for the identification ability of the macrophage identification agent represented by general formula (1) were replaced with the compounds (117), (119), (120), (122), (127), (129), (131), (132) and (138) and the comparative compound (4). By using a resolution R thus obtained as an index, the identification ability for a subtype of each compound was evaluated.

The evaluation results are shown in Table 8. The details of channels shown in Table 8 are shown in Table 3.

TABLE 8

| Example | Compound | Channel | Peak position of M1 macrophage | Peak position of M2 macrophage | Resolution ratio R | Evaluation of macrophage subtype identification | Selectivity |
|---|---|---|---|---|---|---|---|
| Example 81 | (116) | FITC | 4.91 | 12.1 | 0.772 | A | M2 |
| Example 82 | (117) | FITC | 7.35 | 9.73 | 0.318 | B | M2 |
| Example 83 | (119) | AmCyan | 2.60 | 3.94 | 0.273 | B | M2 |
| Example 84 | (120) | Pacific Blue | 10.1 | 5.60 | 0.676 | A | M1 |
| Example 85 | (122) | FITC | 142 | 211 | 0.377 | B | M2 |
| Example 86 | (127) | FITC | 3.99 | 6.00 | 0.381 | B | M2 |
| Example 87 | (129) | Pacific Blue | 31.0 | 13.0 | 0.709 | A | M1 |
| Example 88 | (131) | FITC | 8.06 | 13.5 | 0.480 | B | M2 |
| Example 89 | (132) | FITC | 30.3 | 53.8 | 0.624 | A | M2 |
| Example 90 | (138) | AmCyan | 20.6 | 28.0 | 0.312 | B | M2 |
| Comparative Example 1 | Comparative compound (1) | PE-Cy7 | 1.70 | 1.86 | 0.006 | C | No selectivity |
| Comparative Example 8 | Comparative compound (4) | Pacific Blue | 0.88 | 1.05 | 0.053 | C | No selectivity |

As is obvious from Table 8 and FIG. 1 and FIGS. 15 and 16, although there is no difference in the staining intensity between the M1 macrophages and the M2 macrophages stained by using the comparative compound (1) or (4) and hence these macrophages cannot be identified, if the macrophage identification agent containing the dye compound represented by general formula (10) of the present invention is used, the M1 macrophages and the M2 macrophages can be identified from each other based on a difference in the fluorescence intensity.

Example 91

Two×10$^5$ each of M1 macrophages and M2 macrophages cultured in the same manner as in Example 1 were dispensed into a 1.5 mL tube, and the compound (116) and the compound (120) were added thereto each to a concentration of 1 μM.

A fluorescent signal derived from the compound (116) was measured in the FITC channel (excited at 488 nm, 530/30 nm: center wavelength/wavelength width) and a fluorescent signal derived from the compound (120) was measured in the Pacific Blue channel (excited at 405 nm, 450/50 nm: center wavelength/wavelength width). A cytogram developed by plotting the intensity of the fluorescent signal derived from the compound (1) and obtained in the FITC channel on the ordinate and plotting the intensity of the fluorescent signal derived from the compound (5) and obtained in the Pacific Blue channel on the abscissa was prepared. The operation was performed in the same manner as in Example 1 except for the above.

As a result, as is obvious from FIGS. 17A to 17E, the compound (116) has a characteristic to more strongly stain the M2 macrophages than the M1 macrophages, and on the contrary, the compound (120) has a characteristic to more strongly stain the M1 macrophages than the M2 macrophages. Therefore, on the cytogram developed with respect to the intensity of the fluorescent signal derived from the compound (116) and the intensity of the fluorescent signal derived from the compound (120), the M1 macrophages and the M2 macrophages stained with the compound (116) and the compound (120) are plotted as cell populations having different fluorescent characteristics, and hence, these macrophages can be identified.

This example reveals that a subtype can be identified even when two or more types of compounds for the macrophage identification agent represented by general formula (10) of the present invention are used in combination.

Examples 81 to 91 and Comparative Examples 1 and 8 described above reveal that a subtype contained in a biological sample can be identified by using one or more macrophage identification agents represented by general formula (10) of the present invention.

Sorting of Subtype by Using Macrophage Identification Agent Represented by General Formula (10)

Example 92

One×10$^5$ each of M1 macrophages and M2 macrophages cultured in the same manner as in Example 1 were mixed in a 1.5 mL tube, and the compound (120) was added thereto to a concentration of 1 uM.

The operation was performed in the same manner as in Example 1 except for the above.

Figure 18A:
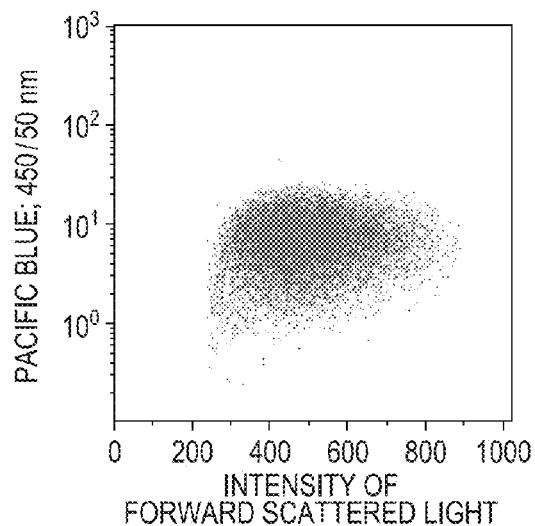
FIGS. 18A, 18B and 18C illustrate cytograms observed in Example 92. The cytogram illustrated in FIG. 18A is obtained from M1 macrophages stained with the compound (120), the cytogram illustrated in FIG. 18B is obtained from M2 macrophages stained with the compound (120), and the cytogram illustrated in FIG. 18C is obtained from a sample of a mixture of the M1 macrophages and the M2 macrophages stained with the compound (120).
Figure 18B:
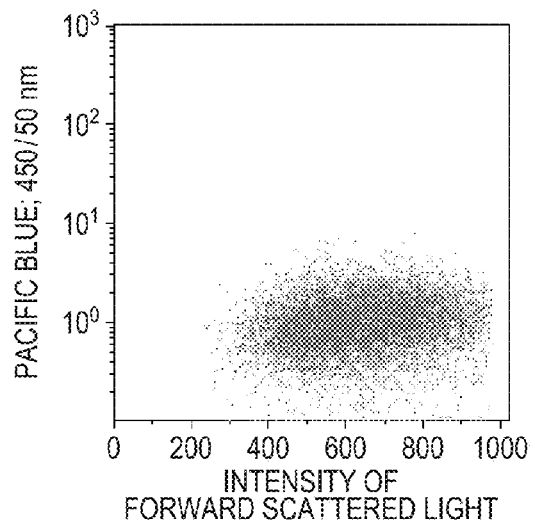
Figure 18C:
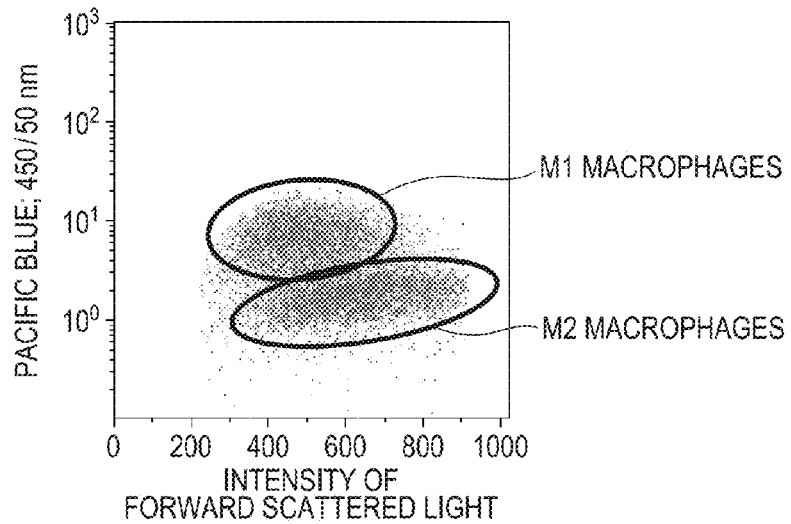

As a result, as is obvious from FIGS. 18A to 18C, the M1 macrophages and the M2 macrophages stained with the compound (120) were plotted, on a cytogram developed with respect to the intensity of forward scattered light affected by the size of cells and the intensity of a fluorescent signal derived from the compound (120), as cell populations having different fluorescence intensity distributions. Since the compound (120) having the characteristic to stain the M1 macrophages more strongly than the M2 macrophages was used for staining, the M1 macrophages can be identified as a cell population having a high fluorescence intensity derived from the compound (120), and on the other hand, the M2 macrophages can be identified as a cell population having a low fluorescence intensity derived from the compound (120). Besides, the M1 macrophages and the M2 macrophages identified by using the compound (120) could be each sorted with an FACS apparatus. The sorted subtypes were confirmed by the fluorescent antibody method and the gene expression analysis.

It was found through Examples 81 to 92 described above that a subtype can be identified and sorted by using the macrophage identification agent represented by general formula (10) of the present invention.

Analysis and Screening of Subtype by Using Macrophage Identification Agent

Example 93

Two×$10^5$ each of M1 macrophages and M2 macrophages cultured in the same manner as in Example 1 were dispensed into a 1.5 mL tube, and the compound (120) was added thereto to a concentration of 1 µM, and furthermore, MK-571 (manufactured by Sigma-Aldrich) was added thereto, as a substance for inhibiting export of the compound (120) having been imported into cells, to a concentration of 10 µM, and the resultant was incubated at 37° C. for 30 minutes. Thereafter, the tube was centrifuged at 180 G for 10 minutes to remove the supernatant, and then, 1 mL of a HBSS buffer containing the MK-571 in a concentration of 10 µM was added thereto to suspend the cells, and the resultant was further incubated at 37° C. for 30 minutes.

The operation was performed in the same manner as in Example 58 except for the above.

Comparative Example 9

Figure 19A:
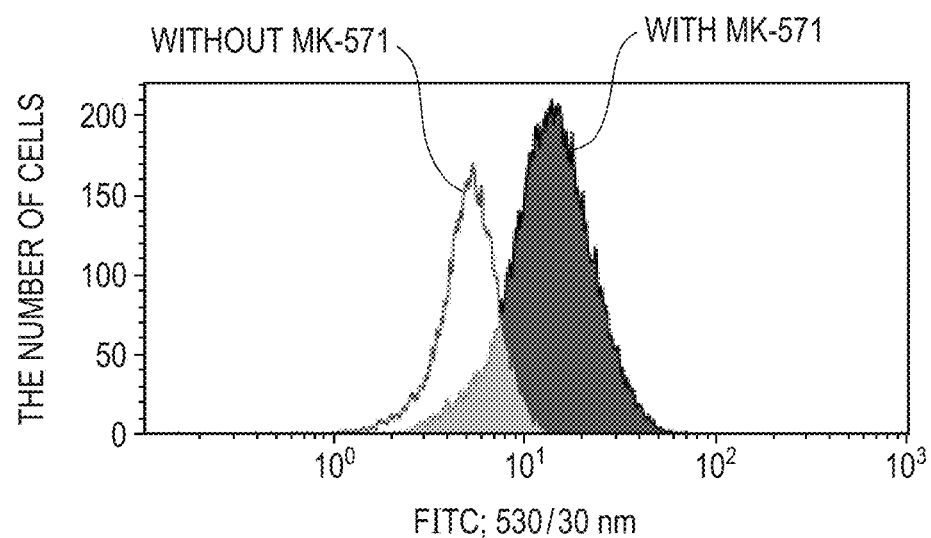
FIGS. 19A and 19B illustrate histograms observed in Example 93 and Comparative Example 9. The histogram illustrated in FIG. 19A is obtained from M1 macrophages stained with the compound (120), and the histogram illustrated in FIG. 19B is obtained from M2 macrophages stained with the compound (120).
Figure 19B:
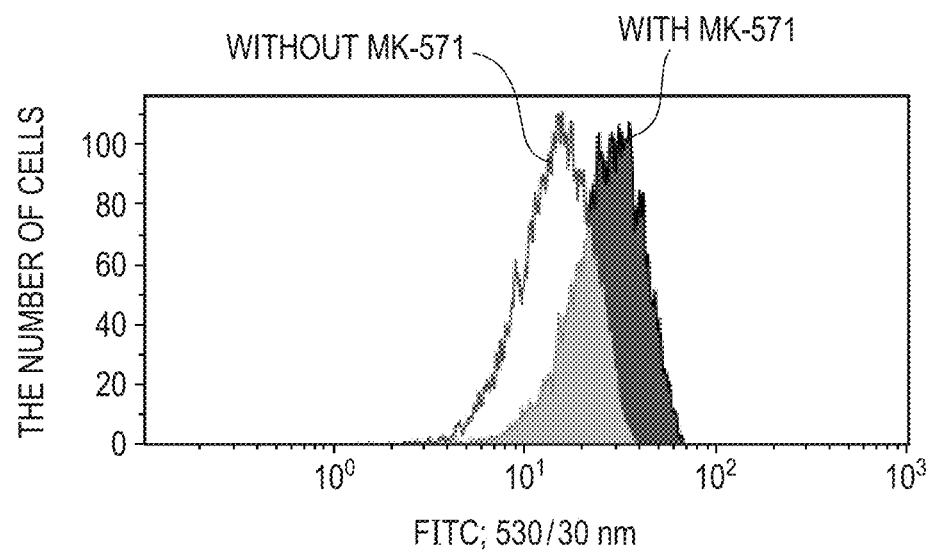

The analysis was performed in the same manner as in Example 93 except that the MK-571 was not added. As a result, as is obvious from FIGS. 19A and 19B, in a histogram in which the fluorescence intensity obtained in the FITC channel for measuring a fluorescent signal derived from the compound (120) was plotted on the abscissa and the number of cells at each fluorescence intensity was plotted on the ordinate, the enhancement of the fluorescence intensity caused by the inhibition by the MK-571 of the export of the compound (120) from the cells was observed in both the M1 macrophages and the M2 macrophages. The degree of the enhancement of the peak intensity caused by adding the MK-571 was evaluated by calculating the resolution R described above by using peak intensities in histograms prepared with and without adding the MK-571. As a result, the degrees were substantially the same, and were 0.739 in the M1 macrophages and 0.730 in the M2 macrophages. Thus, it was found that the influence on the export inhibition by the MK-571 does not depend on the subtypes.

Example 94

Two×$10^5$ each of M1 macrophages and M2 macrophages cultured in the same manner as in Example 1 were dispensed into a 1.5 mL tube, the compound (116) was added thereto to a concentration of 1 uM, and the resultant was incubated at 37° C. for 30 minutes. Thereafter, the tube was centrifuged at 180 G for 10 minutes to remove the supernatant, and then, a blocking treatment for cell surfaces was performed by using 2.4G2 (anti-mouse CD16/32 antibody, manufactured by Biolegend). To the cells having been subjected to the blocking treatment, a FACS buffer containing 0.2 µg of Pacific Blue-labeled anti-CD40 antibody and 0.05 µg of PerCP-labeled anti-Dectin-1 antibody was added for performing the immunofluorescent staining. The fluorescent labeling with these antibodies was selected so that the fluorescence wavelengths of the antibodies could overlap neither with each other nor with the fluorescence wavelengths of the compound (116) and the TO-PRO-3.

The operation was performed in the same manner as in Example 58 except for the above.

As a result, in the M1 macrophages identified based on the strong staining with the compound (116), a fluorescent signal derived from the Pacific Blue-labeled anti-CD40 antibody was observed in the Pacific Blue channel (excited at 405 nm, 450/50 nm: center wavelength/wavelength width). On the contrary, in the M2 macrophages identified based on the weak staining with the compound (116), a fluorescent signal derived from the PerCP-labeled anti-Dectin-1 antibody was observed in a PerCP channel (excited at 488 nm, in a fluorescence wavelength measurement region of 670 to 735 nm). It was found based on this result that the anti-CD40 antibody and the anti-Dectin-1 antibody are antibodies respectively specifically binding to the M1 macrophages and the M2 macrophages.

Identification of Macrophage Subtypes Differentiated from Mouse Cell Line by Using Macrophage Identification Agent Represented by General Formula (10)

Example 95

A fluorescent signal derived from the compound (129) was measured in the Pacific Blue channel (excited at 405 nm, 450/50 nm: center wavelength/wavelength width) in the same manner as in Example 1 except that the compound (1) used in Example 59 was replaced with the compound (129). A histogram was prepared by plotting the fluorescence intensity obtained in the FITC channel on the abscissa and plotting the number of cells at each fluorescence intensity on the ordinate, which is shown in FIG. 20.

Figure 20:
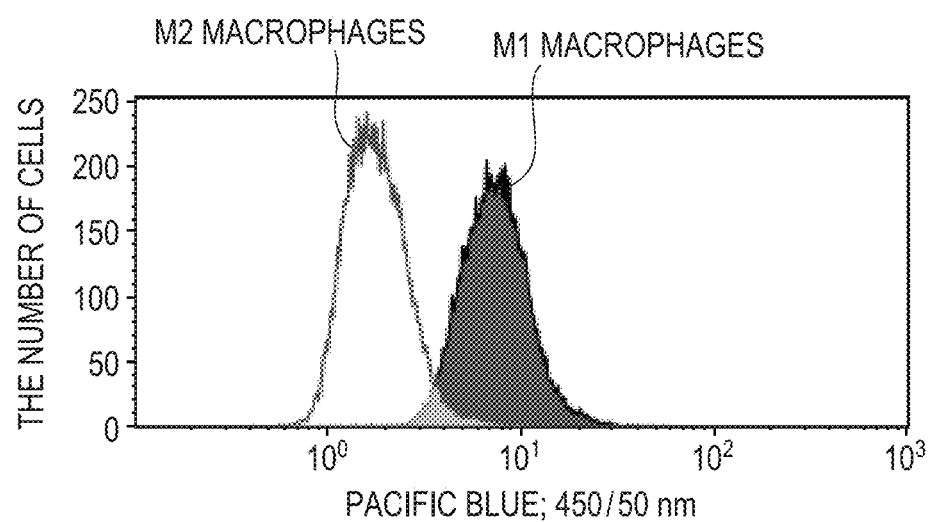
FIG. 20 illustrates a histogram observed in Example 95.

As a result, as is obvious from FIG. 20, the M1 macrophages were stained more strongly by the compound (129) than the M2 macrophages, and hence, it was found that these macrophages can be identified based on a difference in the fluorescence intensity.

Identification of Macrophage Subtypes Differentiated from Human Cell Line by Using Macrophage Identification Agent Represented by General Formula (10)

Example 96

A fluorescent signal derived from the compound (120) was measured in the Pacific Blue channel (excited at 405 nm, 450/50 nm: center wavelength/wavelength width) in the same manner as in Example 1 except that the compound (1) used in Example 60 was replaced with the compound (120). A histogram was prepared by plotting the fluorescence intensity obtained in the Pacific Blue channel on the abscissa and plotting the number of cells at each fluorescence intensity on the ordinate, which is shown in FIG. 21.

Figure 21:
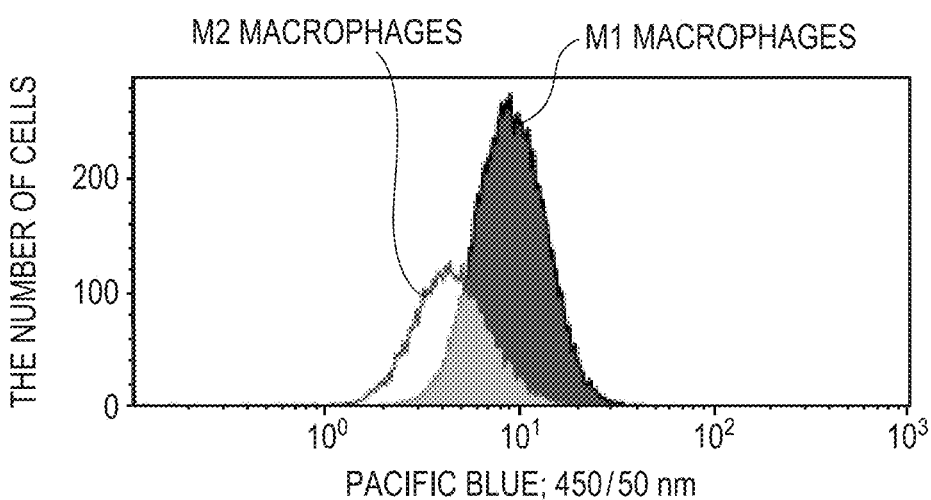
FIG. 21 illustrates a histogram observed in Example 96.

As a result, as is obvious from FIG. 21, the M1 macrophages were stained more strongly by the compound (120) than the M2 macrophages, and hence, it was found that these macrophages can be identified based on a difference in the fluorescence intensity.

Example 97

A fluorescent signal derived from the compound (129) was measured in the Pacific Blue channel (excited at 405 nm, 450/50 nm: center wavelength/wavelength width) in the same manner as in Example 1 except that the compound (1) used in Example 60 was replaced with the compound (129). A histogram was prepared by plotting the fluorescence intensity obtained in the Pacific Blue channel on the abscissa and plotting the number of cells at each fluorescence intensity on the ordinate, which is shown in FIG. 22.

Figure 22:
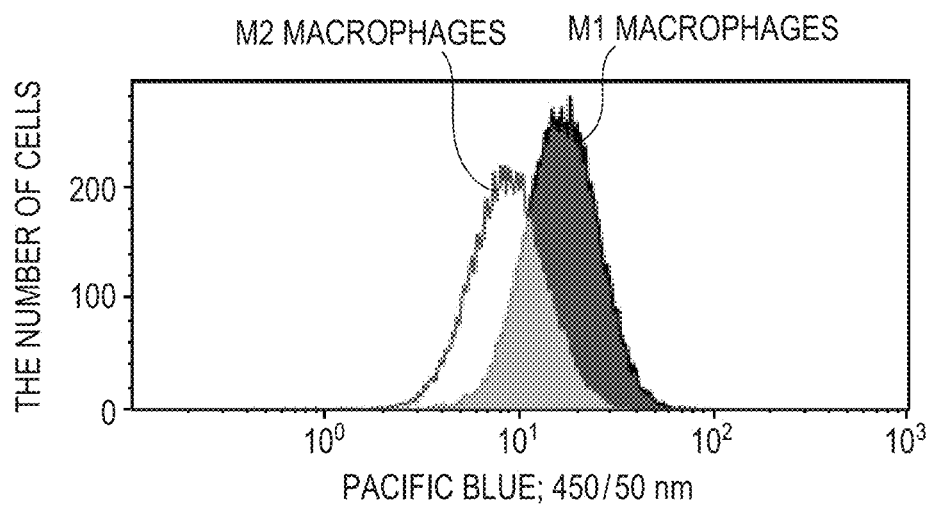
FIG. 22 illustrates a histogram observed in Example 97.

As a result, as is obvious from FIG. 22, the M1 macrophages were stained more strongly by the compound (129) than the M2 macrophages, and hence, it was found that these macrophages can be identified based on a difference in the fluorescence intensity.

It is understood from Examples 93 and 94 that the macrophage identification agent represented by general formula (10) of the present invention can be used for analyzing the correlation between a subtype and a substance.

It is understood from Examples 81 to 94 and Comparative Examples 1 and 8 described above that the macrophage identification agent of the present invention can be used for identifying, sorting, evaluating and analyzing a subtype.

Besides, by performing operations similar to those of Examples 93 and 94 on a plurality of substances, the correlation between a subtype and the substances can be screened by using the macrophage identification agent of the present invention.

Besides, it was revealed based on Example 95 that not only the subtypes differentiated from bone marrow cells but also the subtypes differentiated from a mouse cell line can be identified by using the macrophage identification agent represented by general formula (10) of the present invention.

This result supports that subtypes can be identified by using the macrophage identification agent represented by general formula (10) of the present invention even if the cell type is different.

Besides, it was revealed based on Examples 96 and 97 that not only the subtypes differentiated from bone marrow cells but also the subtypes differentiated from a human cell line can be identified by using the macrophage identification agent represented by general formula (10) of the present invention.

This result further supports that subtypes can be identified by using the macrophage identification agent represented by general formula (10) of the present invention even if human-derived cells are used, and probably suggests that the present invention is applicable to pathologic tissues like human tissues or even a human individual.

Synthetic Example 6

As an example of the macrophage identification agent represented by general formula (11) of the present invention, a synthetic example of the compound (139) will be described.

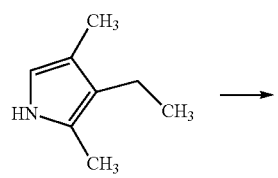

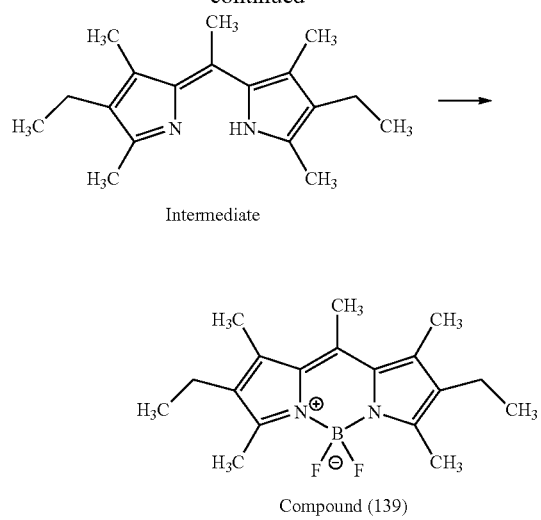

Compound (139)

Under a nitrogen atmosphere, a 50 mL dichloromethane solution of 10 g (81 mmol) of 3-ethyl-2,4-dimethyl pyrrole was cooled to 0° C., and 13.3 mL of acetyl chloride was slowly added dropwise thereto. After completing the dropwise addition, the resulting solution was slowly heated to room temperature and diluted with 200 ml of petroleum ether, and the solvent was distilled off under reduced pressure. To the residue, 5 mL of ethyl acetate and 70 mL of hexane were added, and the thus obtained solid was filtered out. Furthermore, the solid was washed with 28 mL of hexane and 2 mL of ethyl acetate, thereby obtaining 11.1 g of an intermediate.

Under a nitrogen atmosphere, to a 500 mL dichloromethane suspension of the intermediate, 45 mL of triethyl amine was slowly added dropwise, and subsequently, 61 mL of a boron trifluoride ethyl ether complex was added dropwise thereto over 30 minutes or more. After stirring the resulting solution at 25° C. for 2 hours, the solution was cooled to 5° C. or lower and then extracted by adding 300 mL of water and 1000 mL of diethyl ether. After the extraction, an organic layer was washed with 300 mL of water twice and further with 300 mL of a saturated sodium hydrogencarbonate aqueous solution. After drying over anhydrous sodium sulfate, the resultant was filtered out, and the solvent was distilled off under reduced pressure. The resultant was purified by the silica gel column chromatography and then washed with methanol, thereby obtaining 9.3 g (29.2 mmol, yield: 36%) of the compound (139) of interest.

The obtained substance was confirmed to be the compound (139) of interest by the $^1$H nuclear magnetic resonance spectrometric analysis (ECA-400, manufactured by JEOL Ltd.) and the LC/TOF MS (LC/MSD TOF, manufactured by Agilent Technologies, Inc.).

Synthetic Example 7

As an example of the macrophage identification agent represented by general formula (11) of the present invention, a synthetic example of the compound (154) will be described.

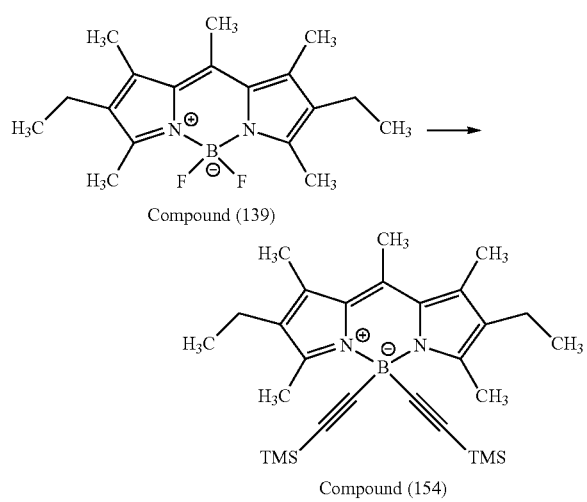

Compound (139)

Compound (154)

Under a nitrogen atmosphere, a 250 mL anhydrous tetrahydrofuran solution of 6.9 mL (50 mmol) of trimethylsilyl acetylene was cooled to −78° C., and 30 mL (50 mmol) of a 1.65 mol/L n-butyllithium hexane solution was added dropwise thereto over 8 minutes. After stirring the resulting solution at −78° C. for 1 hour, the solution was slowly heated to room temperature and stirred for 30 minutes to prepare trimethylsilyl acetylene lithium.

Under a nitrogen atmosphere, a 750 mL anhydrous tetrahydrofuran solution of 6.4 g (20 mmol) of the compound (139) was cooled to 0° C. or lower, and the trimethylsilyl acetylene lithium prepared as described above was added dropwise thereto over 20 minutes or more. After stirring the resulting solution at 0° C. for 20 minutes, the solution was diluted with 500 mL of water to stop the reaction. The resultant was extracted with 250 mL of ethyl acetate three times, and the combined organic layers were washed with 250 mL of a saturated saline. After drying over anhydrous sodium sulfate, the resultant was filtered out, and the solvent was distilled off under reduced pressure. The resultant was purified by the silica gel column chromatography and then washed with hexane, thereby obtaining 6.6 g (13.9 mmol, yield: 70%) of the compound (154) of interest.

The obtained substance was confirmed to be the compound (154) of interest by the $^1$H nuclear magnetic resonance spectrometric analysis and the LC/TOF MS.

Synthetic Examples 8 and 9

The compounds (141) and (148) were obtained in the same manner as in Synthetic Example 6 except that the 3-ethyl-2,4-dimethyl pyrrole used in Synthetic Example 6 was replaced with a corresponding pyrrole derivative. The obtained substances were confirmed to be the compounds (141) and (148) of interest by the $^1$H nuclear magnetic resonance spectrometric analysis and the LC/TOF MS.

Besides, commercially available products were used as the compounds (157), (161), (165), (166), (167) and (169).

Subtype Identification by Using Macrophage Identification Agent Represented by General Formula (11)

Example 98

Figure 23:
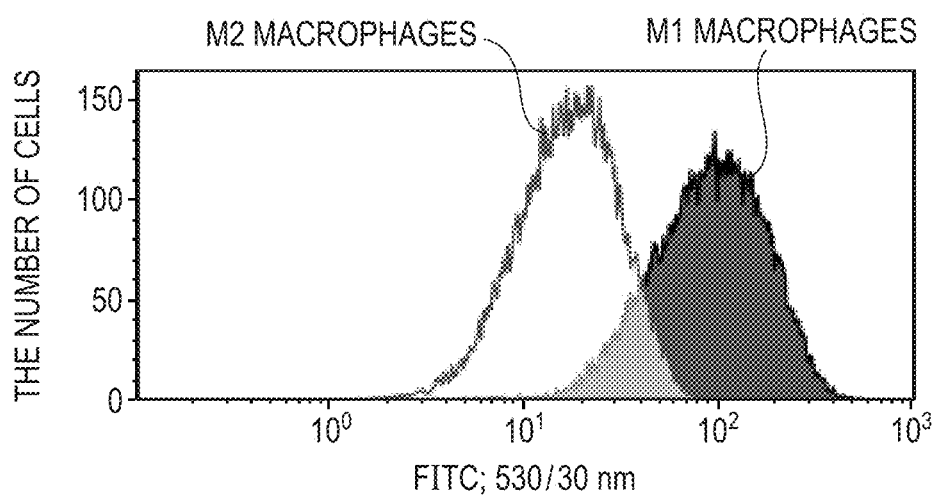
FIG. 23 illustrates a histogram observed in Example 98.
Figure 24A:
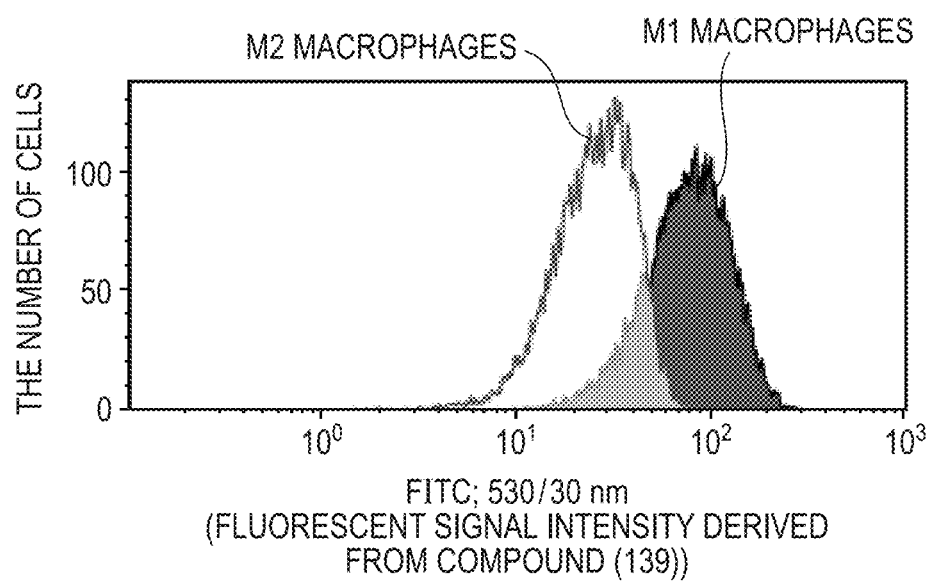
FIGS. 24A, 24B, 24C, 24D and 24E illustrate histograms (FIGS. 24A and 24B) and cytograms (FIGS. 24C, 24D and 24E) observed in Example 108. The cytogram illustrated in FIG. 24C is obtained from M1 macrophages stained with a compound (139) and a compound (161). The cytogram illustrated in FIG. 24D is obtained from M2 macrophages stained with the compound (139) and the compound (161). The cytogram illustrated in FIG. 24E is obtained by overlapping the cytograms illustrated in FIGS. 24C and 24D.
Figure 24B:
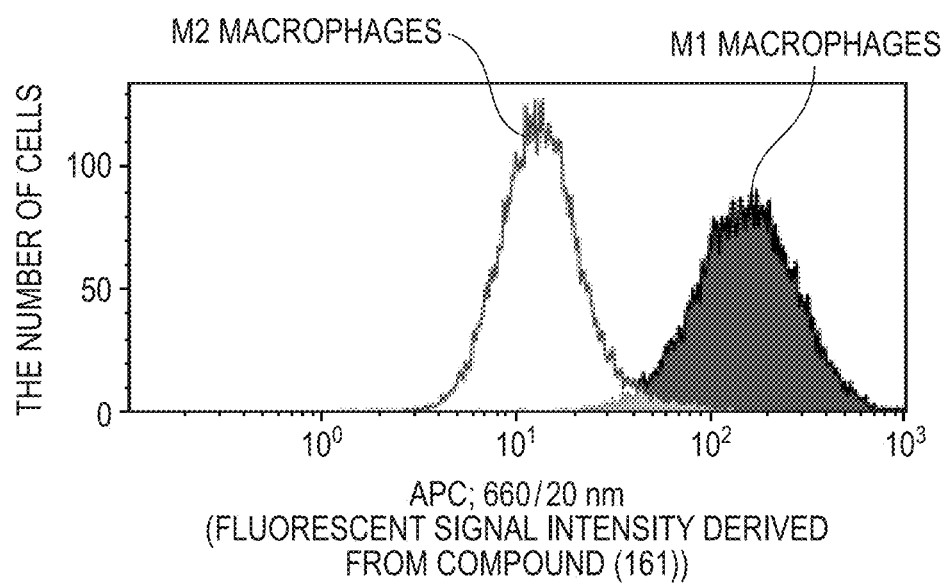
Figure 24C:
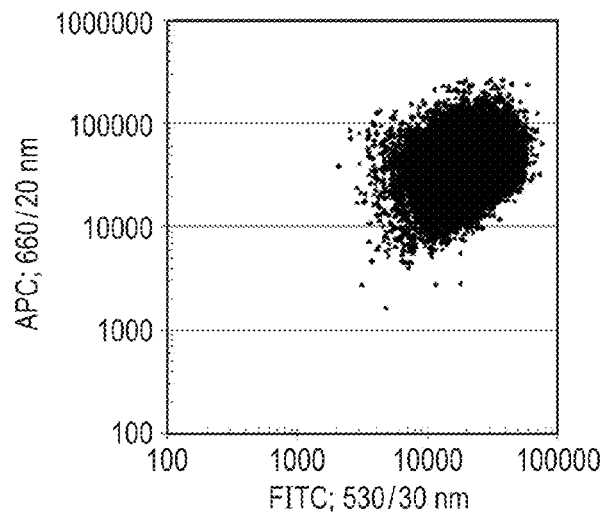
Figure 24D:
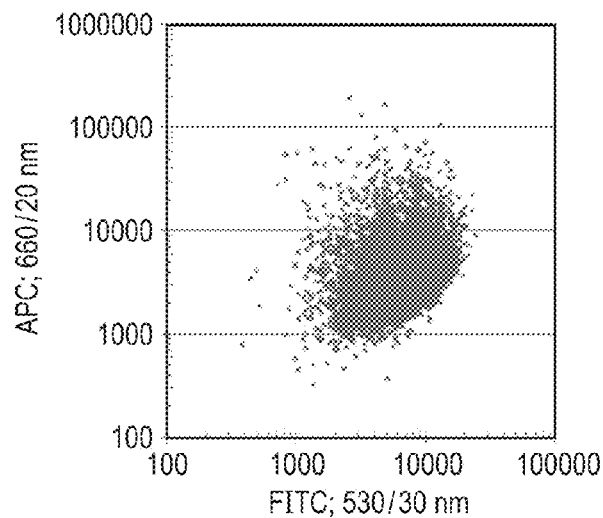
Figure 24E:
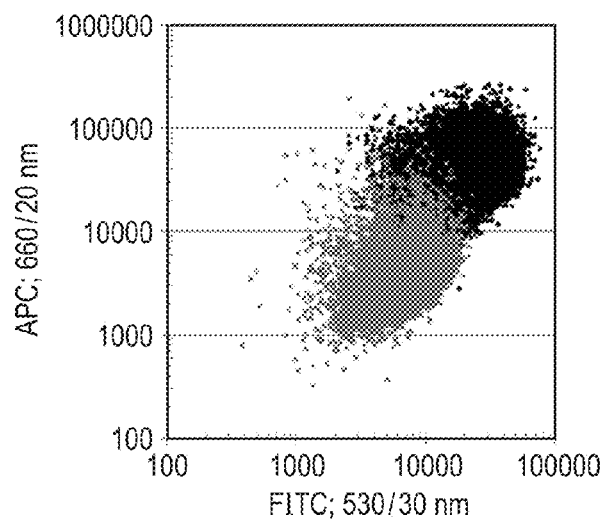

A fluorescent signal derived from the compound (139) was analyzed in the same manner as in Example 1 except that the compound (1) used in Example 1 was replaced with the compound (139) and the TO-PRO-3 was used for identifying dead cells. A histogram was prepared by plotting fluorescence intensity obtained in the FITC channel on the abscissa and plotting the number of cells at each fluorescence intensity on the ordinate, which is shown in FIG. 23.

Examples 99 to 107

Fluorescent signals derived from the compounds (141), (148), (154), (157), (161), (165), (166), (167) and (169) were analyzed in the same manner as in Example 1 except that the compound (1) used in Example 1 was replaced with the compounds (141), (148), (154), (157), (161), (165), (166), (167) and (169).

The results obtained in Examples 98 to 107 described above are shown in Table 9.

<Evaluation Method for Identification Ability of Macrophage Identification Agent Represented by General Formula (11)>

Fluorescent signals derived from the compounds (141), (148), (154), (157), (161), (165), (166), (167) and (169) were measured in channels suitable to the respective compounds in the same manner as in the evaluation method for the identification ability of the macrophage identification agent represented by general formula (1) except that the compounds (3), (4), (6), (7), (9), (11) to (13), (15), (17), (19) to (26), (28), (30) to (33), (35), (36), (38), (42) to (45), (48) to (62), (65), (67), (74) to (76), (82), (83) and (85) and the comparative compounds (1) and (2) used in the evaluation method for the identification ability of the macrophage identification agent represented by general formula (1) were replaced with the compounds (141), (148), (154), (157), (161), (165), (166), (167) and (169). By using a resolution R thus obtained as an index, the identification ability for a subtype of each compound was evaluated.

The evaluation results are shown in Table 9. The details of channels shown in Table 9 are shown in Table 3.

TABLE 9

| Example | Compound | Channel | Peak position of M1 macrophage | Peak position of M2 macrophage | Resolution ratio R | Evaluation of macrophage subtype identification | Selectivity |
|---|---|---|---|---|---|---|---|
| Example 98 | (139) | FITC | 220 | 47.8 | 1.023 | A | M1 |
| Example 99 | (141) | FITC | 16.6 | 9.77 | 0.650 | A | M1 |
| Example 100 | (148) | FITC | 109 | 151 | 0.193 | B | M2 |
| Example 101 | (154) | FITC | 1.25 | 1.63 | 0.160 | B | M2 |
| Example 102 | (157) | FITC | 2.57 | 5.62 | 0.637 | A | M2 |
| Example 103 | (161) | APC | 38.4 | 9.02 | 0.582 | A | M1 |
| Example 104 | (165) | FITC | 1.25 | 2.00 | 0.183 | B | M2 |
| Example 105 | (166) | FITC | 127 | 56.3 | 0.722 | A | M1 |

TABLE 9-continued

| Example | Compound | Channel | Peak position of M1 macrophage | Peak position of M2 macrophage | Resolution ratio R | Evaluation of macrophage subtype identification | Selectivity |
|---|---|---|---|---|---|---|---|
| Example 106 | (167) | FITC | 14.5 | 7.82 | 0.525 | A | M1 |
| Example 107 | (169) | FITC | 10.1 | 8.35 | 0.247 | B | M1 |
| Comparative Example 1 | Comparative compound (1) | PE-Cy7 | 1.70 | 1.86 | 0.006 | C | — |

As is obvious from Table 9 and FIGS. 1 and 23, although there is no difference in the staining intensity between the M1 macrophages and the M2 macrophages stained by using the comparative compound (1) and hence these macrophages cannot be identified, if the macrophage identification agent containing the dye compound represented by general formula (11) of the present invention is used, the M1 macrophages and the M2 macrophages can be identified from each other based on a difference in the fluorescence intensity.

Example 108

Two×$10^5$ each of M1 macrophages and M2 macrophages cultured in the same manner as in Example 1 were dispensed into a 1.5 mL tube, and the compound (139) and the compound (161) were added thereto each to a concentration of 1 uM.

A fluorescent signal derived from the compound (139) was measured in the FITC channel (excitation wavelength: 488 nm, center wavelength: 530 nm, wavelength width: 30 nm) and a fluorescent signal derived from the compound (161) was measured in the APC channel (excitation wavelength: 633 nm, center wavelength: 660 nm, wavelength width: 20 nm). A cytogram developed by plotting the intensity of the fluorescent signal derived from the compound (139) and obtained in the FITC channel on the abscissa and plotting the intensity of the fluorescent signal derived from the compound (161) and obtained in the APC channel on the ordinate was prepared.

The operation was performed in the same manner as in Example 1 except for the above.

As a result, if the compound (139) is used for staining, the M1 macrophages show higher fluorescence intensity in the FITC channel than the M2 macrophages, and on the contrary, if the compound (161) is used for staining, the M1 macrophages show higher fluorescence intensity in the APC channel than the M2 macrophages. Therefore, as is obvious from FIGS. 24A to 24E, on the cytogram developed with respect to the intensity of the fluorescent signal obtained in the FITC channel and the intensity of the fluorescent signal obtained in the APC channel, the M1 macrophages and the M2 macrophages stained with the compound (139) and the compound (161) are plotted as cell populations having different fluorescent characteristics, and hence, these macrophages can be identified.

This example reveals that a subtype can be identified even when two or more types of compounds for the macrophage identification agent represented by general formula (11) of the present invention are used in combination.

Examples 98 to 108 and Comparative Example 1 described above reveal that a subtype contained in a biological sample can be identified by using one or more macrophage identification agents represented by general formula (11) of the present invention.

Sorting of Subtype by Using Macrophage Identification Agent Represented by General Formula (11)

Example 109

One×$10^5$ each of M1 macrophages and M2 macrophages cultured in the same manner as in Example 1 were mixed in a 1.5 mL tube, and the compound (139) was added thereto to a concentration of 1 µM.

The operation was performed in the same manner as in Example 1 except for the above.

Figure 25A:
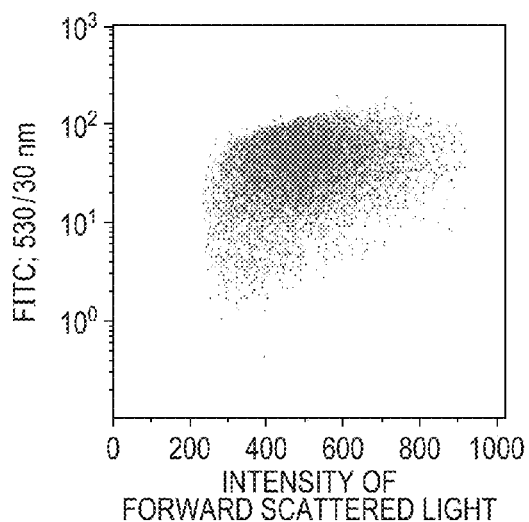
FIGS. 25A, 25B and 25C illustrate cytograms observed in Example 109. The cytogram illustrated in FIG. 25A is obtained from M1 macrophages stained with the compound (139), the cytogram illustrated in FIG. 25B is obtained from M2 macrophages stained with the compound (139), and the cytogram illustrated in FIG. 25C is obtained from a sample of a mixture of the M1 macrophages and the M2 macrophages stained with the compound (139).
Figure 25B:
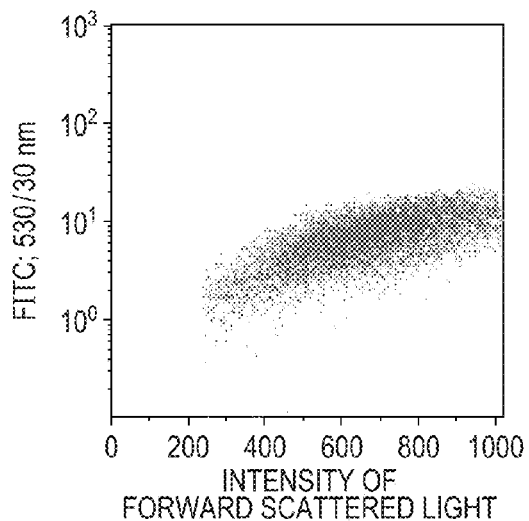
Figure 25C:
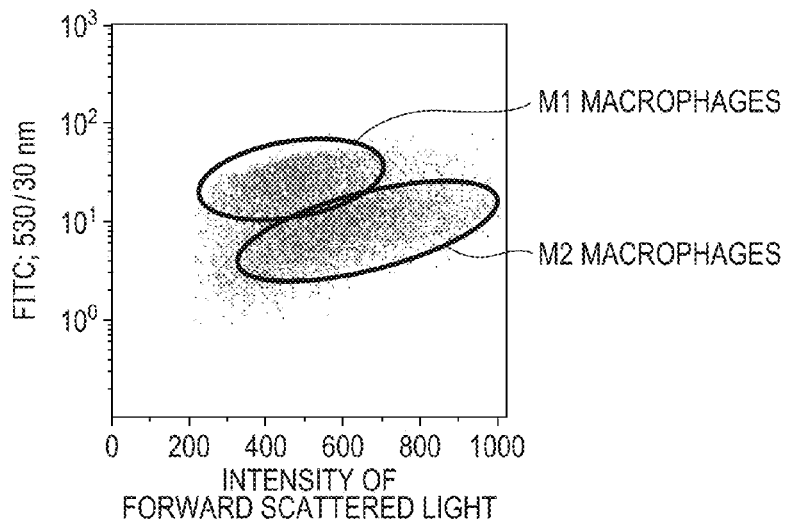

As a result, as is obvious from FIGS. 25A to 25C, the M1 macrophages and the M2 macrophages stained with the compound (139) were plotted, on a cytogram developed with respect to the intensity of forward scattered light affected by the size of cells and the intensity of a fluorescent signal derived from the compound (139), as cell populations having different fluorescence intensity distributions. Since the compound (139) staining the M1 macrophages more strongly than the M2 macrophages was used for staining, the M1 macrophages can be identified as a cell population having a high fluorescence intensity derived from the compound (139), and on the other hand, the M2 macrophages can be identified as a cell population having a low fluorescence intensity derived from the compound (139). Besides, the M1 macrophages and the M2 macrophages identified by using the compound (139) could be each sorted with an FACS apparatus. The sorted subtypes were confirmed by the fluorescent antibody method and the gene expression analysis.

It was found through Examples 98 to 109 described above that a subtype can be identified and sorted by using the macrophage identification agent represented by general formula (11) of the present invention.

Analysis and Screening of Subtype by Using Macrophage Identification Agent Represented by General Formula (11)

Example 110

Two×$10^5$ each of M1 macrophages and M2 macrophages cultured in the same manner as in Example 1 were dispensed into a 1.5 mL tube, and the compound (139) was added thereto to a concentration of 1 µM, and furthermore, 4,4'-diisothiocyanatostilbene-2,2'-disulfonic acid (manufactured by Sigma-Aldrich, hereinafter referred to as DIDS) was added thereto, as a substance for inhibiting export of the compound (139) having been imported into cells, to a concentration of 10 µM, and the resultant was incubated at 37° C. for 30 minutes. Thereafter, the tube was centrifuged at 180 G for 10 minutes to remove the supernatant, and then, 1 mL of a HBSS buffer containing the DIDS in a concentration of 10 µM was added thereto to suspend the cells, and the resultant was further incubated at 37° C. for 30 minutes.

The operation was performed in the same manner as in Example 57 except for the above.

Comparative Example 10

The analysis was performed in the same manner as in Example 110 except that the DIDS used in Example 110 was not added.

Figure 26A:
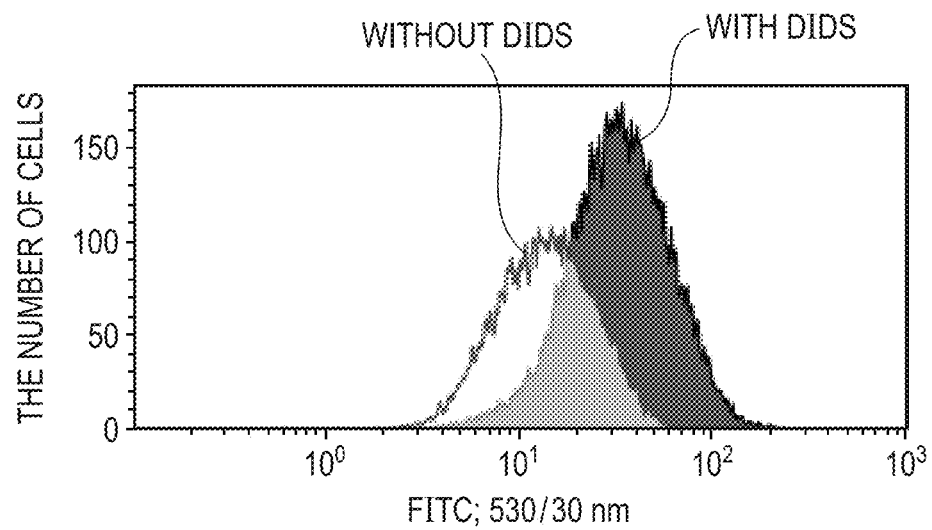
FIGS. 26A and 26B illustrate histograms observed in Example 110 and Comparative Example 10. The histogram illustrated in FIG. 26A is obtained from M1 macrophages stained with the compound (139), and the histogram illustrated in FIG. 26B is obtained from M2 macrophages stained with the compound (139).
Figure 26B:
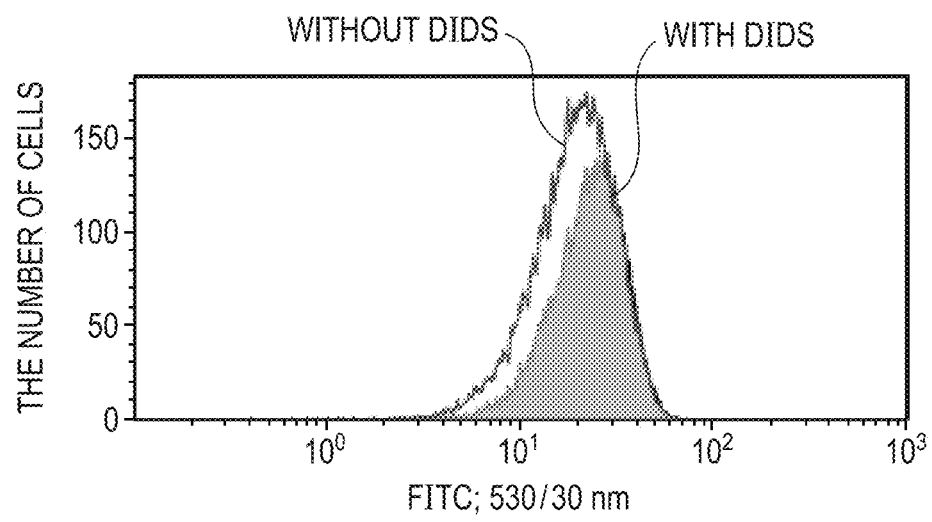

As a result, as is illustrated in FIGS. 26A and 26B, in a histogram in which the fluorescence intensity obtained in the FITC channel for measuring a fluorescent signal derived from the compound (139) was plotted on the abscissa and the number of cells at each fluorescence intensity was plotted on the ordinate, the enhancement of the fluorescence intensity caused by the inhibition by the DIDS of the export of the compound (139) from the cells was observed merely in the M1 macrophages, and thus, it was found that the influence on the export inhibition by the DIDS is different depending on the subtypes.

Example 111

Two×$10^5$ each of M1 macrophages and M2 macrophages cultured in the same manner as in Example 1 were dispensed into a 1.5 mL tube, the compound (161) was added thereto to a concentration of 1 µM, and the resultant was incubated at 37° C. for 30 minutes. Thereafter, the tube was centrifuged at 180 G for 10 minutes to remove the supernatant, and then, a blocking treatment for cell surfaces was performed by using 2.4G2 (anti-mouse CD16/32 antibody, manufactured by Biolegend). To the cells having been subjected to the blocking treatment, a FACS buffer containing 0.2 µg of Pacific Blue-labeled anti-CD40 antibody and 0.1 µg of Alexa Fluor647-labeled anti-Dectin-1 antibody was added for performing the immunofluorescent staining. The fluorescent labeling with these antibodies was selected so that the fluorescence wavelengths of the antibodies could overlap neither with each other nor with the fluorescence wavelengths of the compound (161) and the aqua.

The operation was performed in the same manner as in Example 59 except for the above.

As a result, in the M1 macrophages identified based on the strong staining with the compound (161), a fluorescent signal derived from the Pacific Blue-labeled anti-CD40 antibody was observed in the Pacific Blue channel (excited at 405 nm, 450/50 nm: center wavelength/wavelength width). On the contrary, in the M2 macrophages identified based on the weak staining with the compound (161), a fluorescent signal derived from the Alexa Fluor647-labeled anti-Dectin-1 antibody was observed in the APC channel (excited at 633 nm, 660/20 nm: center wavelength/wavelength width). It was found based on this result that the anti-CD40 antibody and the anti-Dectin-1 antibody are antibodies respectively specifically binding to the M1 macrophages and the M2 macrophages.

Identification of Macrophage Subtypes
Differentiated from Mouse Cell Line by Using
Macrophage Identification Agent Represented by
General Formula (11)

Example 112

A fluorescent signal derived from the compound (141) was measured in the FITC channel (excited at 488 nm, 530/30 nm: center wavelength/wavelength width) in the same manner as in Example 1 except that the compound (1) used in Example 59 was replaced with the compound (141). A histogram was prepared by plotting the fluorescence intensity obtained in the FITC channel on the abscissa and plotting the number of cells at each fluorescence intensity on the ordinate, which is shown in FIG. 27.

Figure 27:
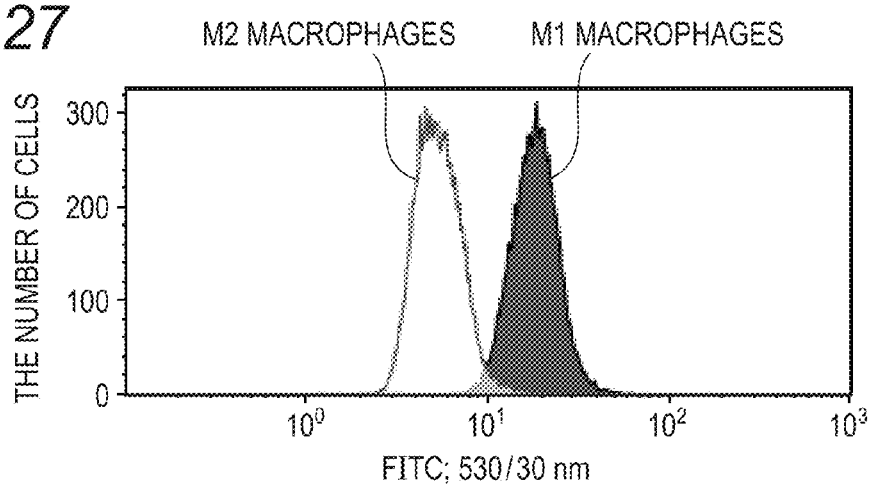
FIG. 27 illustrates a histogram observed in Example 112.

As a result, as is obvious from FIG. 27, the M1 macrophages were stained more strongly by the compound (141) than the M2 macrophages, and hence, it was found that these macrophages can be identified based on a difference in the fluorescence intensity.

Identification of Macrophage Subtypes
Differentiated from Human Cell Line by Using
Macrophage Identification Agent Represented by
General Formula (11)

Example 113

A fluorescent signal derived from the compound (139) was measured in the FITC channel (excited at 488 nm, 530/30 nm: center wavelength/wavelength width) in the same manner as in Example 1 except that the compound (1) used in Example 60 was replaced with the compound (139). A histogram was prepared by plotting the fluorescence intensity obtained in the FITC channel on the abscissa and plotting the number of cells at each fluorescence intensity on the ordinate, which is shown in FIG. 28.

Figure 28:
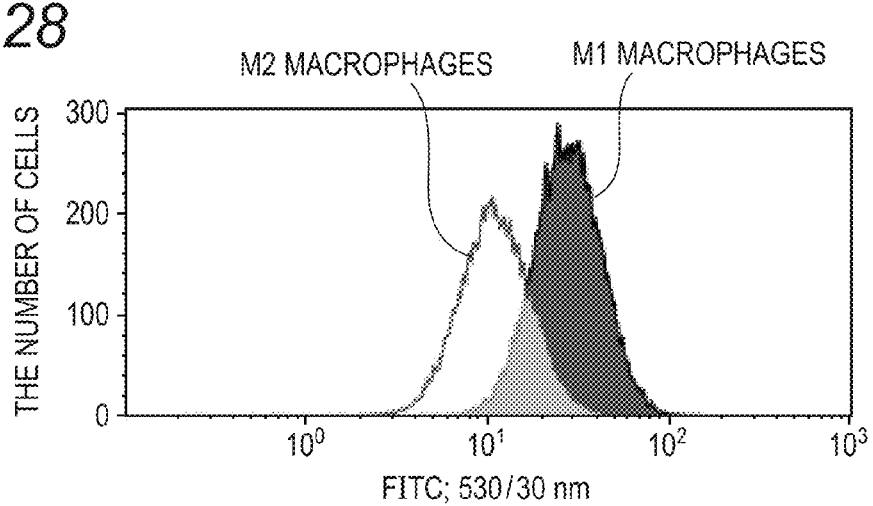
FIG. 28 illustrates a histogram observed in Example 113.

As a result, as is obvious from FIG. 28, the M1 macrophages were stained more strongly by the compound (139) than the M2 macrophages, and hence, it was found that these macrophages can be identified based on a difference in the fluorescence intensity.

Example 114

A fluorescent signal derived from the compound (141) was measured in the FITC channel (excited at 488 nm, 530/30 nm: center wavelength/wavelength width) in the same manner as in Example 1 except that the compound (1) used in Example 60 was replaced with the compound (141). A histogram was prepared by plotting the fluorescence intensity obtained in the FITC channel on the abscissa and plotting the number of cells at each fluorescence intensity on the ordinate, which is shown in FIG. 29.

Figure 29:
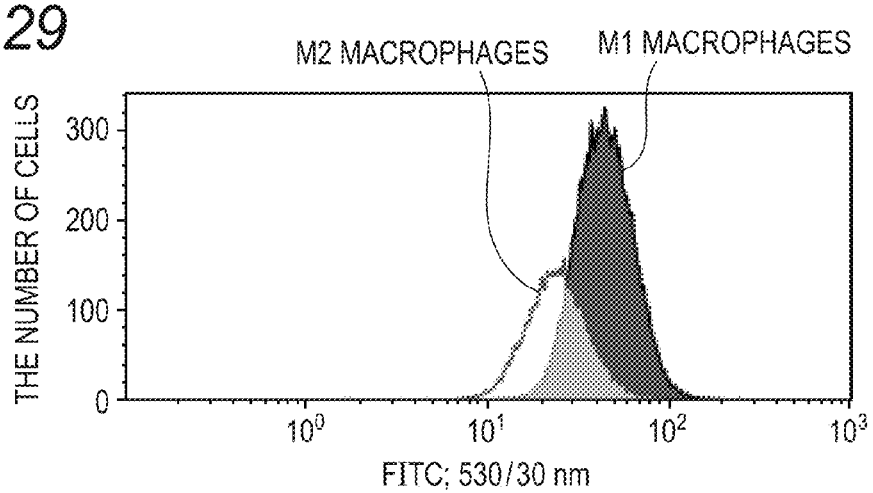
FIG. 29 illustrates a histogram observed in Example 114.
Figure 30A:
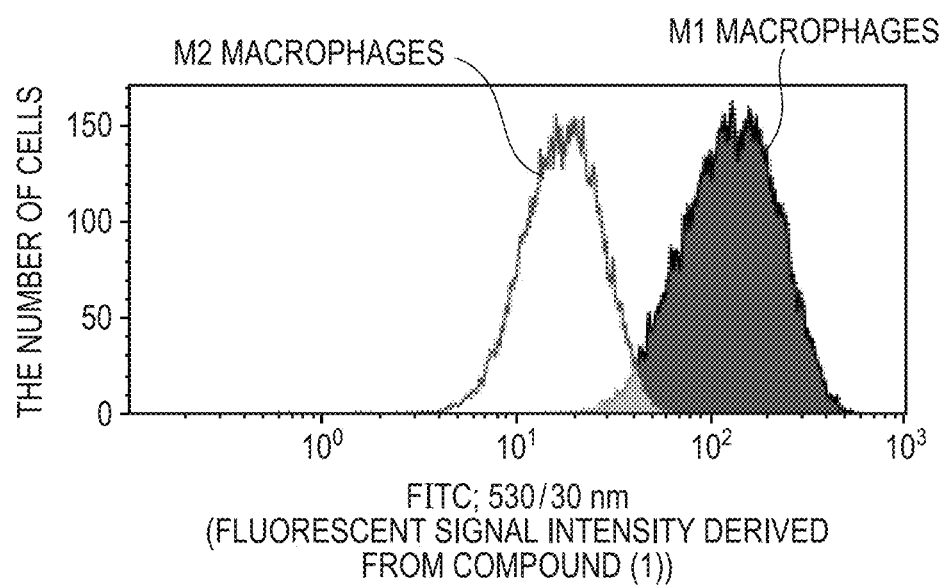
FIGS. 30A, 30B, 30C, 30D and 30E illustrate histograms (FIGS. 30A and 30B) and cytograms (FIGS. 30C, 30D and 30E) observed in Example 115. The cytogram illustrated in FIG. 30C is obtained from M1 macrophages stained with the compound (1) and the compound (113). The cytogram illustrated in FIG. 30D is obtained from M2 macrophages stained with the compound (1) and the compound (113). The cytogram illustrated in FIG. 30E is obtained by overlapping the cytograms illustrated in FIGS. 30C and 30D.
Figure 30B:
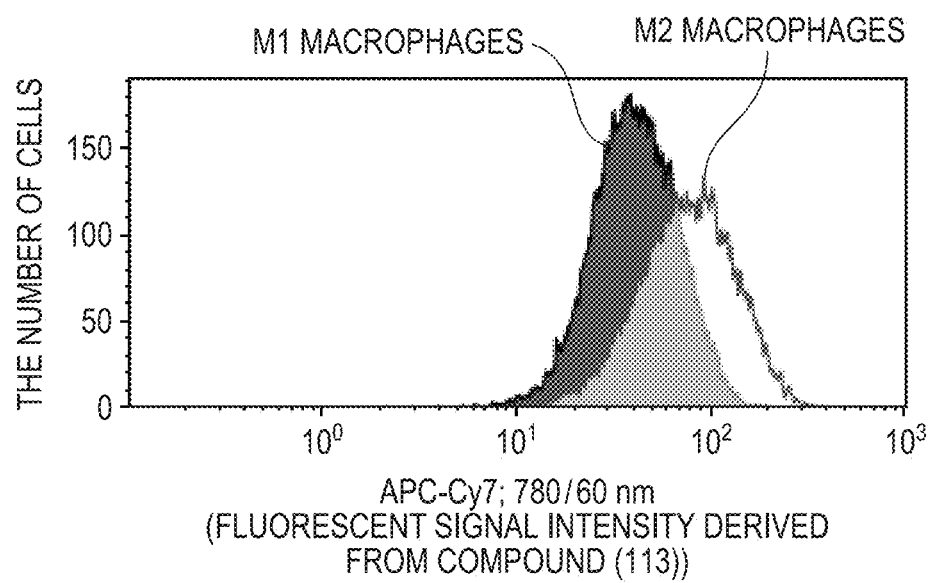
Figure 30C:
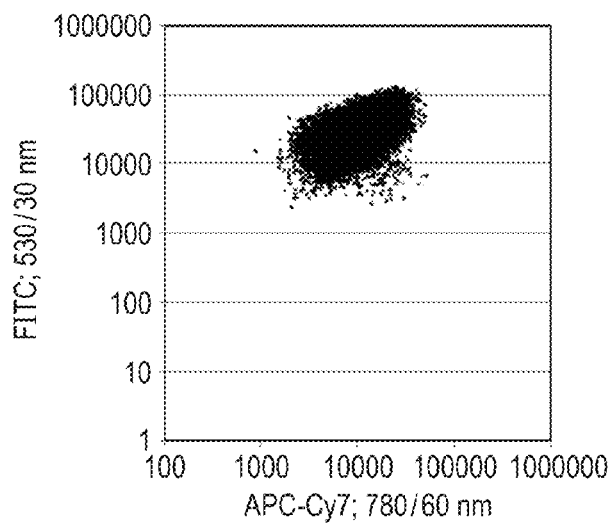
Figure 30D:
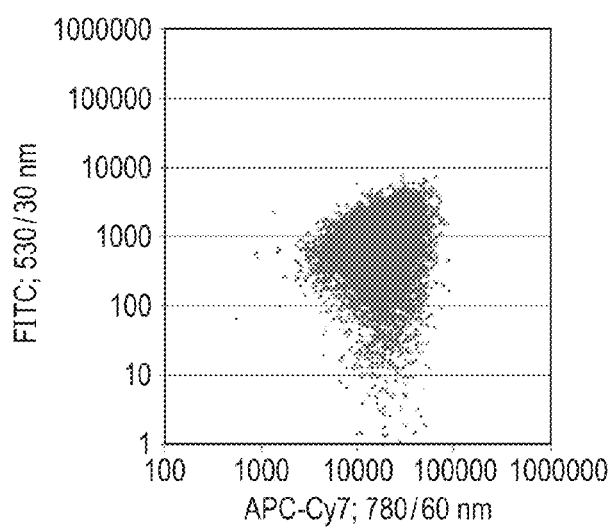
Figure 30E:
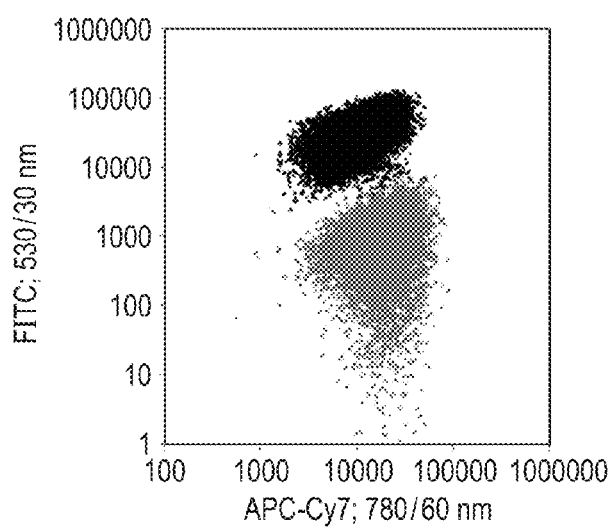

As a result, as is obvious from FIG. 29, the M1 macrophages were stained more strongly by the compound (141) than the M2 macrophages, and hence, it was found that these macrophages can be identified based on a difference in the fluorescence intensity.

It is understood from Examples 110 and 111 that the macrophage identification agent represented by general formula (11) of the present invention can be used for analyzing the correlation between a subtype and a substance.

It is understood from Examples 98 to 111 and Comparative Example 1 described above that the macrophage identification agent represented by general formula (11) of the present invention can be used for identifying, sorting, evaluating and analyzing a subtype.

Besides, by performing operations similar to those of Examples 110 and 111 on a plurality of substances, the correlation between a subtype and the substances can be screened by using the macrophage identification agent represented by general formula (11) of the present invention.

Besides, it was revealed based on Example 112 that not only the subtypes differentiated from bone marrow cells but also the subtypes differentiated from a mouse cell line can be identified by using the macrophage identification agent represented by general formula (11) of the present invention.

This result supports that subtypes can be identified by using the macrophage identification agent represented by general formula (11) of the present invention even if the cell type is different.

Besides, it was revealed based on Examples 113 and 114 that not only the subtypes differentiated from bone marrow cells but also the subtypes differentiated from a human cell line can be identified by using the macrophage identification agent represented by general formula (11) of the present invention.

This result further supports that subtypes can be identified by using the macrophage identification agent represented by general formula (11) of the present invention even if human-derived cells are used, and probably suggests that the present invention is applicable to pathologic tissues like human tissues or even a human individual.

Example 115

Two×$10^5$ each of M1 macrophages and M2 macrophages cultured in the same manner as in Example 1 were dispensed into a 1.5 mL tube, and the compound (1) and the compound (113) were added thereto each to a concentration of 1 µM. Dead cells were identified by using the TO-PRO-3.

A fluorescent signal derived from the compound (1) was measured in the FITC channel (excitation wavelength: 488 nm, center wavelength: 530 nm, wavelength width: 30 nm) and a fluorescent signal derived from the compound (113) was measured in the APC-Cy7 channel (excitation wavelength: 633 nm, center wavelength: 780 nm, wavelength width: 60 nm). A cytogram developed by plotting the intensity of the fluorescent signal derived from the compound (1) and obtained in the FITC channel on the ordinate and plotting the intensity of the fluorescent signal derived from the compound (113) and obtained in the APC-Cy7 channel on the abscissa was prepared.

The analysis was performed on a cell population showing a low signal for the TO-PRO-3, so as to analyze a cell population from which dead cells were eliminated. The operation was performed in the same manner as in Example 1 except for the above.

As a result, as is obvious from FIGS. 30A to 30E, when the compound (1) is used, the M1 macrophages are more strongly stained than the M2 macrophages. On the contrary, when the compound (113) is used, the M2 macrophages are more strongly stained than the M1 macrophages. Therefore, the M1 macrophages and the M2 macrophages stained with the compound (1) and the compound (113) are plotted, on the cytogram developed with respect to the intensities of the fluorescent signals derived from these compounds, as cell populations having different fluorescent characteristics, and hence, these macrophages can be easily identified.

This example reveals that a subtype can be identified even when two or more types of compounds for the macrophage identification agent represented by general formulas (1), (6), (10), and (11) are used in combination.

INDUSTRIAL APPLICABILITY

The macrophage identification agent containing any of the organic compounds represented by general formulas (1), (6), (10) and (11) provided by the present invention is a useful material for realizing subtype identification simply, highly safely and inexpensively. Besides, also in evaluation of a substance affecting a subtype, the macrophage identification agent of the present invention can be used for performing high throughput screening at low cost. Use of the macrophage identification agent of the present invention can remarkably develop the research for clarifying the role of a subtype in an inflammatory disease, and can contribute to development of an effective diagnosis or treatment method for an inflammatory disease, and thus, an extremely useful basic technology industrially and practically can be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-114578, filed May 30, 2013, which is hereby incorporated by reference herein in its entirety.

The invention claimed is:

1. A method for identifying macrophage subtype M1 and macrophage subtype M2, wherein the subtype M1 and the subtype M2 are identified based on a spectral characteristic obtained with a dye compound having a molecular weight of 2000 or less added, wherein the dye compound is at least one compound represented by general formula (1):

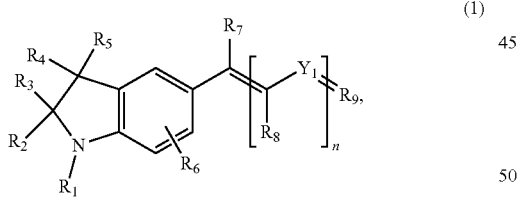
(1)

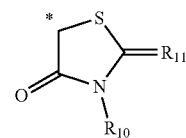
(2)

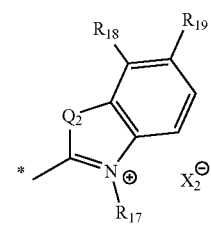
(3)

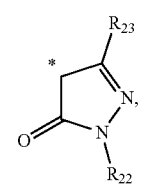
(4)

wherein, in the general formula (1), $R_1$ represents a hydrogen atom, an alkyl group, an aralkyl group, an alkenyl group, or an aryl group; $R_2$ to $R_5$ each independently represents a hydrogen atom, an alkyl group, an aryl group, a carboxyl group, a carboxylalkyl group, or an alkylcarbonyl group, wherein $R_2$ and $R_4$ may be bound to each other to form an aliphatic ring; $R_6$ represents a hydrogen atom, an alkyl group, an alkoxy group, or a halogen atom; $R_7$ and $R_8$ each independently represents a hydrogen atom, an alkyl group, or an aryl group; $R_9$ represents a dicyanomethylene group, a cyanocarboxymethylene group, or any one of general formulas (2) to (4); $Y_1$ represents a carbon atom having aryl group, a cyclopentene ring, a cyclohexene ring or a carbon atom; and n represents 0 or 1, wherein, in the general formula (2), $R_{10}$ represents an alkyl group, a carboxylalkyl group, an alkoxycarbonylalkyl group, or an alkylcarbonyloxyalkyl group; $R_{11}$ represents a sulfur atom, a 2-thioxothiazolidin-4-one group, a thiazoline-2,4-one group, or general formula (5); and "*" represents a binding site,

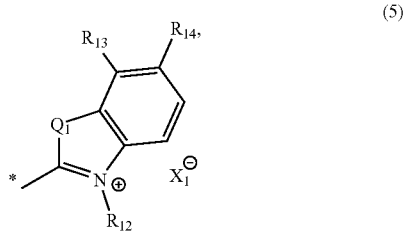

(5)

wherein, in the general formula (5), $R_{12}$ represents an alkyl group, a carboxylalkyl group, an alkoxycarbonylalkyl group, or an alkylcarbonyloxyalkyl group; $R_{13}$ and $R_{14}$ each represent a hydrogen atom and may be bound to each other to form a benzene ring; $Q_1$ represents an oxygen atom, a sulfur atom, a N-alkyl nitrogen atom, or —C($R_{15}$)($R_{16}$)—, wherein $R_{15}$ and $R_{16}$ each independently represent an alkyl group and may be bound to each other to form a ring; $X_1^-$ represents an anionic group; and "*" represents a binding site, wherein, in the general formula (3), $R_{17}$ represents an alkyl group, a carboxylalkyl group, an alkoxycarbonylalkyl group, or an alkylcarbonyloxyalkyl group; $R_{18}$ and $R_{19}$ each represents a hydrogen atom and may be bound to each other to form a benzene ring; $Q_2$ represents an oxygen atom, a sulfur atom, a N-alkyl nitrogen atom, or —C($R_{20}$)($R_{21}$)—, wherein $R_{20}$ and $R_{21}$ each independently represents an alkyl group and may be bound to each other to form a ring; $X_2^-$ represents an anionic group; and "*" represents a binding site, and wherein, in the general formula (4), $R_{22}$ represents an alkyl group or an aryl group; $R_{23}$ represents an alkyl group or a carboxyl group; and "*" represents a binding site.

2. The method according to claim 1, wherein the ring formed when $R_2$ and $R_4$ of the general formula (1) are bound to each other is a cyclopentane ring.

3. The method according to claim 1, wherein $R_9$ is a compound represented by the general formula (2).

4. The method according to claim 1, wherein $R_9$ is a compound represented by the general formula (3).

5. The method according to claim 1, wherein $R_9$ is a compound represented by the general formula (4).

6. A method for identifying macrophage subtype M1 and macrophage subtype M2, wherein the subtype M1 and the subtype M2 are identified based on a spectral characteristic obtained with a dye compound having a molecular weight of 2000 or less added, wherein the dye compound is at least one compound represented by general formula (6):

(6)

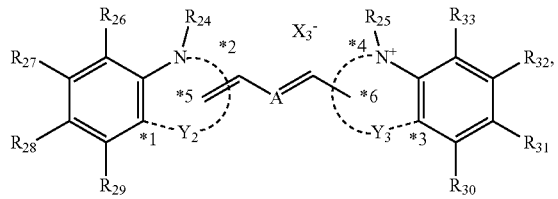

wherein, in the general formula (6), $R_{24}$ and $R_{25}$ each independently represents an alkyl group, a carboxylalkyl group, an alkoxycarbonylalkyl group, or an alkyl-carbonyloxyalkyl group; $R_{26}$ to $R_{33}$ each independently represents a hydrogen atom, an alkyl group, an aryl group, an alkoxy group, a halogen atom, an alkoxysulfonyl group, a N-alkylsulfamoyl group, an alkyloxycarbonyl group, a carbamoyl group, or a N-alkylcarbamoyl group, wherein $R_{26}$ and $R_{27}$, $R_{28}$ and $R_{29}$, $R_{30}$ and $R_{31}$, and $R_{32}$ and $R_{33}$ may be independently cyclized to form a benzene ring; $X_3^-$ represents an anionic group; $Y_2$ represents a group containing *1, *2, and *5 and containing an oxygen atom, a sulfur atom, a N-alkyl nitrogen atom or —C($R_{34}$)($R_{35}$)—, or a group containing *1, *2, and *5 and represented by *1-C*5-CH═CH-*2 or *1-CH═CH-*5-*2; $Y_3$ represents a group containing *3, *4, and *6 and containing an oxygen atom, a sulfur atom, a N-alkyl nitrogen atom, or —C($R_{34}$)($R_{35}$)—, or a group containing *3, *4, and *6 and represented by *3-$Y_3$-*6-*4, *3-C*6-CH═CH-*4, or *3-CH═CH-*6-*4, wherein $R_{34}$ and $R_{35}$ each independently represents an alkyl group and may be bound to each other to form a ring; and A represents a 3-oxocyclobutenolate ring or is represented by general formula (7) or (8):

(7)

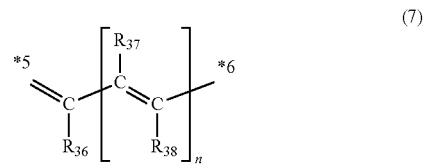

(8)

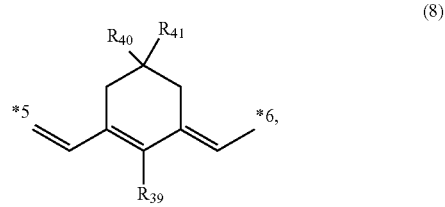

wherein, in the general formula (7), $R_{36}$ to $R_{38}$ each independently represents a hydrogen atom, an alkyl group or an aryl group, and n represents a value of 0 to 2, wherein, in the general formula (8), $R_{39}$ represents a hydrogen atom, a phenyl group, a thiol group, an alkoxy group, an aryloxy group, or a halogen atom; and $R_{40}$ and $R_{41}$ each independently represents a hydrogen atom, an alkyl group, or an alkyloxycarbonyl group.

7. The method according to claim 6, wherein the compound represented by the general formula (6) is represented by general formula (9):

(9)

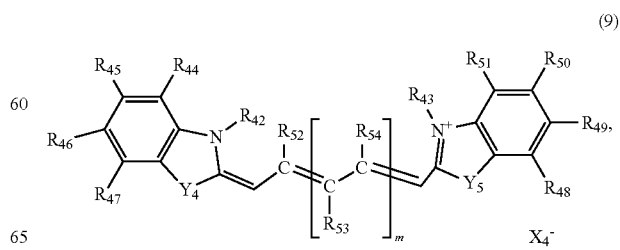

wherein, in the general formula (9), $R_{42}$ and $R_{43}$ each independently represents an alkyl group, a carboxylalkyl group, an alkylcarbonyloxyalkyl group, or an alkoxycarbonyl alkyl group; $R_{44}$ to $R_{51}$ each independently represents a hydrogen atom, an alkyl group, an aryl group, an alkoxy group, a halogen atom, an alkoxysulfonyl group, a N-alkylsulfamoyl group, an alkyloxycarbonyl group, or a N-alkylcarbamoyl group, wherein $R_{44}$ and $R_{45}$, $R_{46}$ and $R_{47}$, $R_{48}$ and $R_{49}$, and $R_{50}$ and $R_{51}$ may be independently cyclized to form a benzene ring; $R_{49}$ to $R_{51}$ each independently represents a hydrogen atom, an alkyl group or an aryl group; m represents a value of 0 to 2; $X_4^-$ represents an anionic group; and $Y_4$ and $Y_5$ each represents an oxygen atom, a sulfur atom, or an alkylene group, wherein the alkylene group may have a substituent, the substituent used in this case is an alkyl group, and the substituents may be bound to each other to form an aliphatic ring.

8. The method according to claim 6, wherein A of the general formula (6) is a 3-oxocyclobutenolate ring.

9. A method for identifying macrophage subtype M1 and macrophage subtype M2, wherein the subtype M1 and the subtype M2 are identified based on a spectral characteristic obtained with a dye compound having a molecular weight of 2000 or less added,
wherein the dye compound is at least one compound represented by general formula (10):

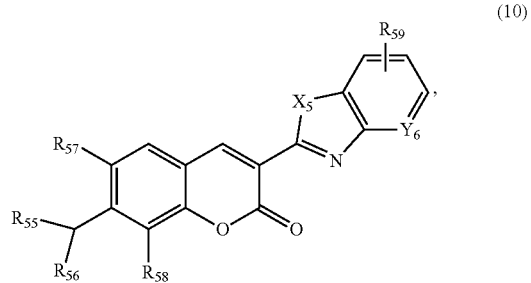

(10)

wherein, in the general formula (10), $R_{55}$ and $R_{56}$ each independently represents an alkyl group; $R_{57}$ and $R_{58}$ each independently represents a hydrogen atom or an alkyl group, wherein $R_{55}$ and $R_{57}$, and $R_{56}$ and $R_{58}$ may be independently bound to each other to form a ring; $R_{59}$ represents a hydrogen atom, an alkyl group, an aryl group, an alkoxy group, or a halogen atom; $X_5$ represents a sulfur atom, an oxygen atom, or $-NR_6-$; and $Y_6$ represents a carbon atom or a nitrogen atom.

10. A method for identifying macrophage subtype M1 and macrophage subtype M2, wherein the subtype M1 and the subtype M2 are identified based on a spectral characteristic obtained with a dye compound having a molecular weight of 2000 or less added,
wherein the dye compound is at least one compound represented by general formula (11):

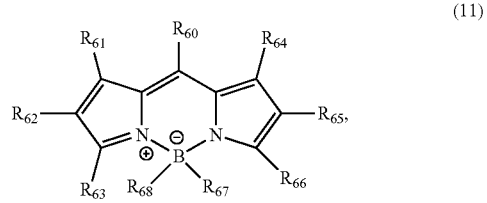

(11)

wherein, in the general formula (11), $R_{60}$ represents a hydrogen atom, an alkyl group, an aryl group, a thioalkyl group, an amino group, a hetero ring group, an alkenyl group, a hydroxyl group, a halogen atom, or an alkoxy group; $R_{61}$ to $R_{66}$ each independently represents a hydrogen atom, an alkyl group, an aryl group, a hetero ring group, an aralkyl group, or a sulfonyl group, wherein $R_{62}$ and $R_{63}$, and $R_{65}$ and $R_{66}$ may be bound to each other to form a hetero ring; and $R_{67}$ and $R_{68}$ each independently represents a fluorine atom or an alkynyl group.

11. The method according to claim 1, wherein the subtype M1 contained in a biological sample is identified by utilizing that the subtype M1 has different staining properties from the subtype M2.

12. The method according to claim 1, wherein the subtype M2 contained in a biological sample is identified by utilizing that the subtype M1 has different staining properties from the subtype M2.

13. The method according to claim 1, wherein the subtype M1 and the subtype M2 contained in a biological sample are identified by utilizing that the subtype M1 has different staining properties from the subtype M2.

14. The method according to claim 1, wherein the dye compound is exposed to a biological sample.

15. The method according to claim 6, wherein the subtype M1 contained in a biological sample is identified by utilizing that the subtype M1 has different staining properties from the subtype M2.

16. The method according to claim 6, wherein the subtype M2 contained in a biological sample is identified by utilizing that the subtype M1 has different staining properties from the subtype M2.

17. The method according to claim 6, wherein the subtype M1 and the subtype M2 contained in a biological sample are identified by utilizing that the subtype M1 has different staining properties from the subtype M2.

18. The method according to claim 6, wherein the dye compound is exposed to a biological sample.

19. The method according to claim 9, wherein the subtype M1 contained in a biological sample is identified by utilizing that the subtype M1 has different staining properties from the subtype M2.

20. The method according to claim 9, wherein the subtype M2 contained in a biological sample is identified by utilizing that the subtype M1 has different staining properties from the subtype M2.

21. The method according to claim 9, wherein the subtype M1 and the subtype M2 contained in a biological sample are identified by utilizing that the subtype M1 has different staining properties from the subtype M2.

22. The method according to claim 9, wherein the dye compound is exposed to a biological sample.

23. The method according to claim 10, wherein the subtype M1 contained in a biological sample is identified by utilizing that the subtype M1 has different staining properties from the subtype M2.

24. The method according to claim 10, wherein the subtype M2 contained in a biological sample is identified by utilizing that the subtype M1 has different staining properties from the subtype M2.

25. The method according to claim 10, wherein the subtype M1 and the subtype M2 contained in a biological sample are identified by utilizing that the subtype M1 has different staining properties from the subtype M2.

26. The method according to claim 10, wherein the dye compound is exposed to a biological sample.

27. A method for staining macrophage subtype M1 and macrophage subtype M2, wherein the subtype M1 and the subtype M2 can be identified based on a spectral characteristic obtained with a dye compound having a molecular weight of 2000 or less added, the method comprising exposing a biological sample to the dye compound, wherein the dye compound is at least one compound represented by general formula (1):

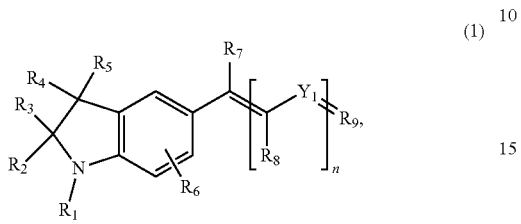
(1)

wherein, in the general formula (1), $R_1$ represents a hydrogen atom, an alkyl group, an aralkyl group, an alkenyl group, or an aryl group; $R_2$ to $R_5$ each independently represents a hydrogen atom, an alkyl group, an aryl group, a carboxyl group, a carboxylalkyl group, or an alkylcarbonyl group, wherein $R_2$ and $R_4$ may be bound to each other to form an aliphatic ring; $R_6$ represents a hydrogen atom, an alkyl group, an alkoxy group, or a halogen atom; $R_7$ and $R_8$ each independently represents a hydrogen atom, an alkyl group, or an aryl group; $R_9$ represents a dicyanomethylene group, a cyanocarboxymethylene group, or any one of general formulas (2) to (4); $Y_1$ represents a carbon atom having aryl group, a cyclopentene ring, a cyclohexene ring or a carbon atom; and n represents 0 or 1,

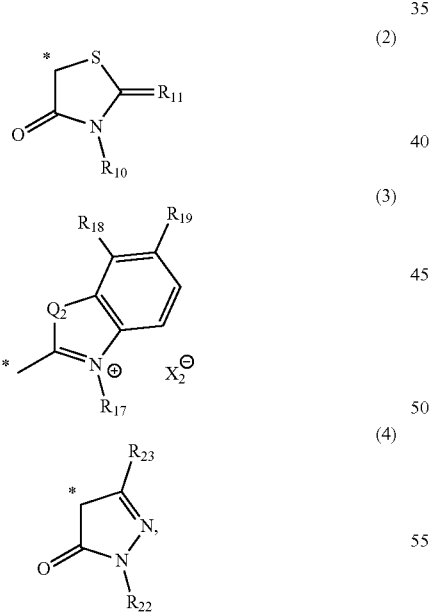

wherein, in the general formula (2), $R_{10}$ represents an alkyl group, a carboxylalkyl group, an alkoxycarbonylalkyl group, or an alkylcarbonyloxyalkyl group; $R_{11}$ represents a sulfur atom, a 2-thioxothiazolidin-4-one group, a thiazoline-2,4-one group, or general formula (5); and "*" represents a binding site,

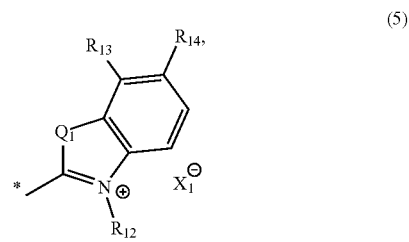
(5)

wherein, in the general formula (5), $R_{12}$ represents an alkyl group, a carboxylalkyl group, an alkoxycarbonylalkyl group, or an alkylcarbonyloxyalkyl group; $R_{13}$ and $R_{14}$ each represent a hydrogen atom and may be bound to each other to form a benzene ring; $Q_1$ represents an oxygen atom, a sulfur atom, a N-alkyl nitrogen atom, or —C($R_{15}$)($R_{16}$)—, wherein $R_{15}$ and $R_{16}$ each independently represent an alkyl group and may be bound to each other to form a ring; $X_1^-$ represents an anionic group; and "*" represents a binding site, wherein, in the general formula (3), $R_{17}$ represents an alkyl group, a carboxylalkyl group, an alkoxycarbonylalkyl group, or an alkylcarbonyloxyalkyl group; $R_{18}$ and $R_{19}$ each represents a hydrogen atom and may be bound to each other to form a benzene ring; $Q_2$ represents an oxygen atom, a sulfur atom, a N-alkyl nitrogen atom, or —C($R_{20}$)($R_{21}$)—, wherein $R_{20}$ and $R_{21}$ each independently represents an alkyl group and may be bound to each other to form a ring; $X_2^-$ represents an anionic group; and "*" represents a binding site, and wherein, in the general formula (4), $R_{22}$ represents an alkyl group or an aryl group; $R_{23}$ represents an alkyl group or a carboxyl group; and "*" represents a binding site.

28. The method according to claim 27, wherein the ring formed when $R_2$ and $R_4$ of the general formula (1) are bound to each other is a cyclopentane ring.

29. The method according to claim 27, wherein $R_9$ is a compound represented by the general formula (2).

30. The method according to claim 27, wherein $R_9$ is a compound represented by the general formula (3).

31. The method according to claim 27, wherein $R_9$ is a compound represented by the general formula (4).

* * * * *

SEQUENCE LISTING

<160> NUMBER OF SEQ ID NOS: 18

<210> SEQ ID NO 1
<211> LENGTH: 19
<212> TYPE: DNA
<213> ORGANISM: Artificial Sequence
<220> FEATURE:
<223> OTHER INFORMATION: Primer

<400> SEQUENCE: 1
tgaagcaggc atctgaggg                    19

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2

```
cgaaggtgga agagtgggag                                          20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
agacctcaac agagccctca                                          20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
tcgaaggtga gctgaacgag                                          20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
acggcatgga tctcaaagac                                          20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
agatagcaaa tcggctgacg                                          20

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
ctccaagcca aagtccttag ag                                       22

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
aggagctgtc attagggaca tc                                       22

<210> SEQ ID NO 9
<211> LENGTH: 25
<212> TYPE: DNA
<213> ORGANISM: Artificial Sequence
```

```
<220> FEATURE:
<223> OTHER INFORMATION: Primer

<400> SEQUENCE: 9
cggtgaacca ataattacc aaaat                                          25

<210> SEQ ID NO 10
<211> LENGTH: 18
<212> TYPE: DNA
<213> ORGANISM: Artificial Sequence
<220> FEATURE:
<223> OTHER INFORMATION: Primer

<400> SEQUENCE: 10
gtggagcagg tgtgggct                                                 18

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
caacagcgac acccactcct                                               20

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
caccctgttg ctgtagccaa a                                             21

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
tgcactttgg agtgatcggc                                               20

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
ctcagcttga gggtttgcta c                                             21

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
agccactcac ctcttcagaa c                                             21
```

```
<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
gcctctttgc tgctttcaca c                                            21

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
ccctcagaaa gtgatgtgcc ta                                           22

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
tacttgtgag gtcaccgcct                                              20
```